United States Patent
Shaw

(10) Patent No.: US 11,845,055 B2
(45) Date of Patent: Dec. 19, 2023

(54) SWELLABLE ORGANICALLY MODIFIED SILICA AS NANOREACTORS

(71) Applicant: Appalachian State University, Boone, NC (US)

(72) Inventor: Nicholas N. Shaw, Boone, NC (US)

(73) Assignee: Appalachian State University, Boone, NC (US)

( * ) Notice: Subject to any disclaimer, the term of this patent is extended or adjusted under 35 U.S.C. 154(b) by 168 days.

(21) Appl. No.: 17/280,690

(22) PCT Filed: Apr. 1, 2020

(86) PCT No.: PCT/US2020/026234
§ 371 (c)(1),
(2) Date: Mar. 26, 2021

(87) PCT Pub. No.: WO2020/206010
PCT Pub. Date: Oct. 8, 2020

(65) Prior Publication Data
US 2022/0008887 A1    Jan. 13, 2022

Related U.S. Application Data

(60) Provisional application No. 62/827,728, filed on Apr. 1, 2019.

(51) Int. Cl.
*B01J 19/00* (2006.01)
*B01J 20/22* (2006.01)
*B01J 20/28* (2006.01)
*B01J 20/30* (2006.01)
*B01J 20/34* (2006.01)
*C01B 33/18* (2006.01)
*C07C 67/48* (2006.01)

(52) U.S. Cl.
CPC ......... *B01J 19/0093* (2013.01); *B01J 20/226* (2013.01); *B01J 20/28007* (2013.01); *B01J 20/3085* (2013.01); *B01J 20/3433* (2013.01); *C01B 33/18* (2013.01); *B01J 2219/00819* (2013.01); *B01J 2219/00864* (2013.01); *B01J 2220/4806* (2013.01); *C01P 2006/90* (2013.01); *C07C 67/48* (2013.01)

(58) Field of Classification Search
CPC ....... C01B 33/00; C01B 33/113; C01B 33/12; C01B 33/18; C01P 2006/00; C01P 2006/90; C07C 67/00; C07C 67/475; C07C 67/48; C07K 1/00; C07K 1/02; C10L 1/00; C10L 1/02; C10L 1/026
See application file for complete search history.

(56) References Cited

PUBLICATIONS

Edmiston et al., Absorption of dissolved organic species from water using organically modified silica that swells, 2009, Separation and Purification Technology 66, 532-540. (Year: 2009).*

(Continued)

*Primary Examiner* — Natasha E Young
(74) *Attorney, Agent, or Firm* — McDonnell Boehnen Hulbert & Berghoff LLP

(57) ABSTRACT

The present disclosure provides methods for conducting chemical reactions and for conducting a multi-step chemical reactions using swellable organically modified silica (SOMS) as nanoreactors.

21 Claims, 8 Drawing Sheets

(56) References Cited

PUBLICATIONS

Hayes, "Peptide Bond Formation in Nano-Reactors", Biology Departmental Honors Thesis, Appalachian State University, Apr. 20, 2018, 50 pages.

Vaughan, "Esterification of carboxylic acids for analysis via gas chromatography using swellable organically modified silica as a nano-reactor", Department of Chemistry and Fermentation Sciences Honors Thesis, Aug. 2019, 73 pages.

* cited by examiner

SWELLABLE ORGANICALLY MODIFIED SILICA AS NANOREACTORS

CROSS-REFERENCE TO RELATED APPLICATIONS

This application is the US national phase under 35 U.S.C. § 371 of International Application No. PCT/US2020/026234, now WO 2020/206010, filed Apr. 1, 2020, which claims priority to U.S. Provisional Application No. 62/827,728 filed Apr. 1, 2019, the contents of each of which are hereby incorporated by reference in their entirety.

BACKGROUND OF THE INVENTION

Field of the Invention

The present disclosure relates to the use of swellable organically modified silica (SOMS) as nanoreactors. More particularly, the present disclosure relates to the use of SOMS to facilitate synthetic organic chemistry reactions, including to prepare biofuels.

Description of the Related Art

Synthetic organic chemistry is the design, construction, and analysis of new molecules for practical purposes. Traditional methods of synthesizing compounds involve suspending reactants in a solvent and allowing the solution to stir in a reactor. On a fundamental level, the reactants need to collide with sufficient velocity and in the correct three-dimensional orientation in order for a reaction to take place and for the compound to be synthesized.

There are certain inherent limitations to these traditional methods. In particular, the suspended reactant molecules must come into physical proximity for the reaction to proceed, which can be a challenge a larger reactor, but less of a challenge in a smaller reactor where the physical distance for two molecules to traverse in order to be in physical proximity is less. Decreasing reactor size has been explored using, e.g., nano-droplets (the dispersion of reactants on a nano-sized droplet of solvent), as well as microfluidic devices. For example, Britton et al. has performed reactions using continuous flow processing with a vortex fluidic device (VFD), and using a thin film microfluidic platform. (See, e.g. Britton et al., *Chem. Eur. J.* 23: 13270-78 (2017)). Others have utilized nanoreactors made of activated carbon, meso-porous carbon, or activated alumina to produce materials that could not be prepared in a macro-reactor (Miura et al., *Chem. Eng. Sci.* 62: 5655-60 (2007)), mesoporous materials as a catalyst support for nanostructured catalysts to synthesize acridine derivatives (Amani et al, *Intl. J. Adv. Biotech. and Res.* 7(4): 1785-94 (2016)), and molecular nanoreactors (e.g. micelles, polymers, etc.) (Karnali, R., Intl. J. Adv. Biotech. and Res. 8(3): 1766-74 (2017)).

And while an enhancement of reactivity is observed, none of these methods are capable of producing commercially viable amounts of desired products.

SUMMARY OF THE INVENTION

In one aspect, the present disclosure provides a method for conducting a chemical reaction comprising (i) combining reactants, solvent, and swellable organically modified silica (SOMS) to create a reaction mixture; (ii) conducting a first reaction cycle by evaporating the solvent from the SOMS; (iii) optionally conducting an additional reaction cycle by (a) reintroducing solvent to the SOMS; and then (b) evaporating the solvent from the SOMS; (iv) optionally repeating step (iii) one or more times; (v) washing the SOMS with solvent to recover the product in solution; and (vi) evaporating the solvent from the product solution of step (v) to isolate the product. In certain embodiments of this aspect of the invention, steps (ii) through (iv) are performed simultaneously.

In another aspect, the present disclosure provides a method for conducting a multi-step chemical reaction comprising (i) conducting a first reaction by (a) combining reactants, solvent, and swellable organically modified silica (SOMS) to create a reaction mixture; (b) conducting a first reaction cycle for the first reaction by evaporating the solvent from the SOMS; (c) optionally conducting an additional reaction cycle for the first reaction by (I) reintroducing solvent to the SOMS; and then (II) evaporating the solvent from the SOMS; (d) optionally repeating step (c) one or more times; (ii) conducting a subsequent reaction by (a) introducing solvent and one or more additional reactants to the SOMS; (b) conducting a first reaction cycle for the subsequent reaction by evaporating the solvent from the SOMS; (c) optionally conducting an additional reaction cycle for the subsequent reaction by (I) reintroducing solvent to the SOMS; and then (II) evaporating the solvent from the SOMS; (d) optionally repeating step (c) one or more times; (iii) optionally repeating step (ii) one or more times; (iv) washing the SOMS with solvent to recover the final product in solution; and (v) evaporating the solvent from the final product solution of step (iv) to isolate the final product.

BRIEF DESCRIPTION OF THE DRAWINGS

(FIG. 3A) Dependence of reaction progress on the number of closes for the conversion of canola oil into biodiesel fuel. (FIG. 3B) Comparison between a traditionally conducted imine condensation reaction (right bar) and the same imine condensation reaction conducted in SOMS nanoreactors (left bar).

DETAILED DESCRIPTION OF THE INVENTION

Figure 1:
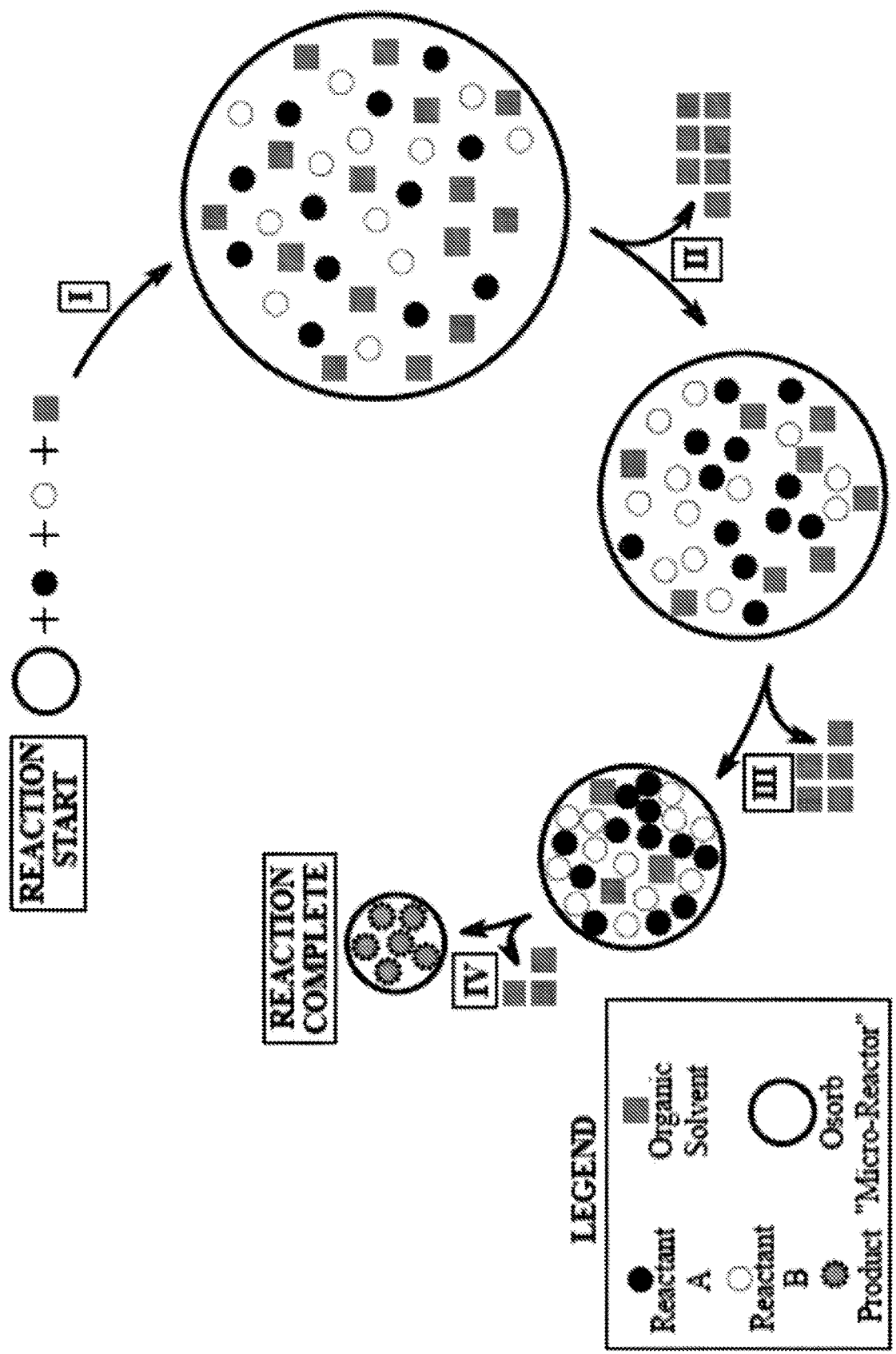
FIG. 1. General schematic of a reaction conducted using SOMS. SOMS behaves as a "nanoreactor" when organic reactants are diluted with solvent and introduced to SOMS, which causes the SOMS to swell (I). SOMS contracts upon the removal of solvent (II-III), which drives the reactants closer together in the SOMS nanoreactor. Upon complete removal of solvent (IV), the reactants are encapsulated in the SOMS nanoreactor, sufficiently close in physical proximity to ensure molecular reactivity. The desired product is easily recovered when the product laden SOMS is washed with organic solvent.

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

It is also to be understood that unless clearly indicated otherwise by the context, embodiments disclosed for one aspect or embodiment of the invention can be used in other aspects or embodiments of the invention as well, and/or in combination with embodiments disclosed in the same or other aspects of the invention. Thus, the disclosure is intended to include, and the invention includes, such combinations, even where such combinations have not been explicitly delineated.

Recitation of ranges of values herein are merely intended to serve as a shorthand method of referring individually to each possible range falling within the range, unless otherwise indicated herein, and each range is incorporated into the specification as if it were individually recited herein. For example, if a temperature is stated as 40°–50° C., it is intended that values such as 40°-45°, 45°-50°, 42°-48°, etc. are expressly enumerated in this specification. These are only examples of what is specifically intended, and all possible combinations of numerical values between and including the lowest value and the highest value enumerated are to be considered to be expressly stated in this disclosure. Additionally, the recitation of ranges is meant to include individual values within the range as if they were individually recited herein, for example if a temperature range is stated as 40°–50° C., it is intended that values such as 40°, 45°, 48°, etc. are expressly enumerated in this specification.

Unless otherwise defined, all technical terms used herein have the same meaning as commonly understood by one of ordinary skill in the art to which this disclosure belongs.

The inventors have discovered that swellable organically modified silica (SOMS, commercially available as Osorb®), a commercially available product used in water remediation, agriculture, and personal care products, is capable of restricting reactants to nanosized environments (i.e. nanoreactors) and can facilitate synthetic organic chemistry reactions.

Accordingly, the present disclosure provides a method for conducting a chemical reaction comprising: (i) combining reactants, solvent, and swellable organically modified silica (SOMS) to create a reaction mixture; (ii) conducting a first reaction cycle by evaporating the solvent from the SOMS; (iii) optionally conducting an additional reaction cycle by (a) reintroducing solvent to the SOMS; and then (b) evaporating the solvent from the SOMS; (iv) optionally repeating step (iii) one or more times; (v) washing the SOMS with solvent to recover the product in solution; and (vi) evaporating the solvent from the product solution of step (v) to isolate the product.

As used herein, "reactant" refers to any starting material for the desired chemical reaction. Any number of reactants may be used. In certain embodiments, 2, 3 or 4 reactants are used with the methods disclosed herein.

As used herein, "solvent" refers to any non-aqueous substance capable of dissolving a solute in order to form a solution. Exemplary solvents that may be used with the methods disclosed herein include, but are not limited to, acetic acid, acetone, acetonitrile, benzene, n-butanol, sec-butanol, t-butanol, butanone, carbon tetrachloride, chlorobenzene, chloroform, cyclohexane, cyclopentane, 1,2-dichloroethane, dichloromethane, diethylene glycol, diethyl ether, diglyme (diethylene glycol dimethyl ether), 1,2-dimethoxy-ethane (glyme, DME), dimethyl-formamide (DMF), dimethyl sulfoxide (DMSO), 1,4-dioxane, ethanol, ethyl acetate, ethylene glycol, formic acid, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroine), propylene carbonate, n-propanol, isopropanol, pyridine, tetrahydrofuran (THF), toluene, triethyl amine, o-xylene, m-xylene, and p-xylene, and any combination thereof. The term "solvent" as used herein is meant to including not only individual solvents, but also to encompass any mixture of one or more solvents.

Swellable organically modified silica (SOMS) is a porous silica-based adsorbent material. See, e.g. U.S. Pat. No. 7,790,830, the contents of which are hereby incorporated by reference. The nanopores within SOMS serve as nanoreactors in the methods disclosed herein.

The reactants, solvent, and SOMS are combined to create a reaction mixture. In this context, use of the term "combined" or "combining" or the like is not intended to limit in any way the order, steps, number of steps, or methods utilized to create the reaction mixture. Thus, in certain embodiments, the reactants may be dissolved (or suspended) in solvent to create a reaction solution, and the reaction solution then combined with the SOMS to create the reaction mixture. In a variation of this embodiment, additional solvent may be added once the reaction solution is combined with the SOMS to create the reaction mixture. In other embodiments, the SOMS may be combined with solvent, and that mixture combined with the reactants, which may be in solution. One of skill in the art will recognize that there are various way of creating the reaction mixture and select a suitable way for use in the methods disclosed herein.

The reaction mixture is held within in a vessel. The vessel may be any flask, reactor, etc. capable of containing the SOMS throughout the reaction process. Where elevated temperatures are utilized, the vessel should be capable of being uniformly heated. Additionally, the vessel should be configured, where appropriate, for use with additional equipment as needed for a particular reaction, for example configured to be attached to a reflux condensor or to a rotary evaporator. When combined with the reactants and solvent, the SOMS will swell. The solvent is then evaporated, causing the SOMS to collapse/close, leaving the reactants encapsulated within the collapsed nanoreactors to undergo reaction. (FIG. 1). Evaporation may be achieved by any method known in the art. In some embodiments, evaporation is achieved under reduced pressure and/or with elevated temperatures. As used herein, terms like "reduced pressure" and "elevated temperatures" are relative to standard conditions, i.e. atmospheric pressure and room temperature. One of skill in the art will be able to optimize evaporation conditions for rapid solvent evaporation, which allows for fast collapse of the SOMS nanoreactors, significant force on the reactants contained therein, and greater reaction efficiency.

The process of swelling the SOMS (by addition of a reactant solution or by addition of a solvent), followed by evaporation of the solvent and collapse of the SOMS, represents one reaction cycle. In some embodiments, e.g. where the reaction is not driven to completion following a single reaction cycle, solvent is added and evaporated for one or more additional cycles. This "flexes" the nanoreactor and allows the reaction to proceed to completion. Optionally, additional amounts of one or more of the reactants may be added with the solvent introduction in additional reaction cycles. In certain embodiments of the invention, the methods disclosed herein comprise 1, 2, 3, 4, 5, 6, 7, 8, 9, 10, 11, 12, 13, 14, 15, 16, 17, 18, 19, or 20 reaction cycles, or any range comprising these specific reaction cycles, for example 1-20 reaction cycles, 1-10 reaction cycles, 10-15 reaction cycles, 2-8 reaction cycles, and 5-15 reaction cycles, as well as ranges of reaction cycles not specifically exemplified herein. In some embodiments, more than 20 reaction cycles may be utilized, for example 25, 30, 35, 40, 45, 50, 55, 60, 65, 70, 75, 80, 85, 90, 95, or 100 reaction cycles, or, for example, a number of reaction cycles that is any integer number between 25-100. Similarly, the methods disclosed herein comprise any range of the number of reaction cycles recited herein, for example 1-100 reaction cycles, 25-50 reaction cycles, and 25-75 reaction cycles, as well as ranges of reaction cycles not specifically exemplified herein. In certain embodiments of the invention, the reaction proceeds, over the course of the completed reaction cycles, to at least about 60%, to at least about 65%, to at least about 70%, to at least about 75%, to at least about 80%, to at least about 82%, to at least about 84%, to at least about 86%, to at least about 88%, to at least about 90%, to at least about 91%, to at least about 92%, to at least about 93%, to at least about 94%, to at least about 95%, to at least about 96%, to at least about 97%, to at least about 98%, to at least about 99%, or to at least about 100% completion.

Product may be recovered by washing the SOMS with additional solvent. The SOMS will swell, and the product will be replaced by solvent within the nanoreactors. In some embodiments, washing may be combined with simultaneous filtration during recovery of the product. The product may be isolated by evaporation of the solvent, or by any standard method of product isolation (e.g. precipitation, extraction, etc.), following recovery from SOMS, and optionally purified.

Following recovery of the product, the SOMS can be washed and reused multiple times without loss of yield of product in later uses.

The same solvent may be used throughout all steps of the methods disclosed herein, or alternatively different solvents may be used in different steps, e.g. in the reaction mixture, when combining the SOMS with a reactant solution, in performing second or subsequent reaction cycles, and in the washing steps.

The present disclosure also provides a variation of the method disclosed above in which steps (ii) through (iv) (i.e.: (ii) conducting a first reaction cycle by evaporating the solvent from the SOMS; (iii) optionally conducting an additional reaction cycle by (a) reintroducing solvent to the SOMS; and then (b) evaporating the solvent from the SOMS; (iv) optionally repeating step (iii) one or more times) are performed simultaneously. With reference to this variation of the method disclosed above, "simultaneously" is used herein to mean that the steps are performed in an ongoing, concurrent cycle, where solvent is continuously evaporated from and returned to the SOMS. In this embodiment of the invention, the evaporation and return of solvent, i.e. the simultaneous performance of steps (ii) through (iv), can be conducted for any length of time, for example for 1 hour, for 6 hours, for 12 hours, for 18 hours, for 24 hours, or for 48 hours, or for any number of hours that is an integer value between 1 and 48, or for any range comprising these times, for example for 1-12 hours, for 12-24 hours, or for 1-48 hours.

In certain embodiments, the disclosure provides methods that encompass multi-step syntheses, i.e. syntheses where there is a first reaction followed by a second, third, fourth, etc. reaction. In such embodiments, the method as disclosed above comprises additional steps prior to washing the SOMS with solvent to recover the product in solution. In particular, such additional steps involve conducting a subsequent (i.e. second, third, fourth, etc.) reaction by (a) introducing solvent and one or more additional reactants to the SOMS; (b) conducting a first reaction cycle for the subsequent reaction by evaporating the solvent from the SOMS; (c) optionally conducting an additional reaction cycle for the subsequent reaction by (I) reintroducing solvent to the SOMS; and then (II) evaporating the solvent from the SOMS; and (d) optionally repeating step (c) one or more times. Steps (a) through (d) may be repeated one or more times for further subsequent reactions. Once the multi-step synthesis is complete, the final product may be isolated by washing the SOMS with solvent to recover the final product in solution and evaporating the solvent from the final product solution.

The methods disclosed herein may be used to conduct any chemical reaction, and more particularly any synthetic organic chemistry reaction. Exemplary reactions that may be utilized with the methods disclosed herein include, but are not limited to, a nucleophilic alkyl substitution reaction, a nucleophilic alkyl substitution reaction, an electrophilic aromatic substitution reaction, a nucleophilic aromatic addition reaction, a cycloaddition reaction, a direct amidation reaction, an elimination reaction, an electrophilic alkene or alkyne addition reaction, a nucleophilic alkene or alkyne addition reaction, a one-pot reaction, a wittig reaction, the synthesis of acetylsalicylic acid, the synthesis of acetaminophen, the synthesis of resveratrol, the synthesis of diazepam, the synthesis of amphetamine, the synthesis of kyotorphin, the synthesis of peptides, the synthesis of monastrol, or the synthesis of biodiesel fuel.

In those embodiments in which the chemical reaction is the synthesis of biodiesel fuel, the reactants may comprise a triglyceride and an alcohol. The alcohol may be any alcohol known in the art, including, but not limited to methanol, ethanol, n-propanol, isopropanol, n-butanol, sec-butanol, and t-butanol.

The SOMS-based reactions of the methods of the invention may be conducted at room temperature, or they may be conducted at a lower or at a higher temperature. In certain embodiments, the SOMS-based reactions are conducted at elevated temperatures of 30°-120° C. In certain embodiments, they are conducted at 40°-100° C., 40°-80° C., or 40°-60° C. In certain embodiments, they are conducted at 40° C., 45° C., 50° C., 55° C., or 60° C. Any heating source known in the art may be used to achieve the elevated temperatures, including but not limited to a heating mantle.

The SOMS-based reactions may be conducted at atmospheric pressure, or under negative or under positive pressure. Negative pressure may be 900 mbar to 1 mbar, or any value or range therein. The SOMS-based reactions may be conducted in an open or in a closed system, and may be under aerobic or anaerobic conditions.

The SOMS-based reactions of the methods of the invention may be used for small-scale laboratory production of products, or they may be used on a commercial scale. In non-limiting examples, the methods of the invention can be used to produce about 5-10 mg of product, or they may be used to produce about 100 g or more of product.

The methods disclosed herein have widespread applicability. In non-limiting examples, they may be used to synthesize life science chemicals (applications and products that include, but are not limited to, biological substances, pharmaceuticals, diagnostics, animal health products, vitamins, and pesticides), specialty chemicals (applications and products that include, but are not limited to, electronic chemicals, industrial gases, adhesives, paints, inks, chemical crop protection, sealants and coatings, industrial and institutional cleaning chemicals, and catalysts), polymers (applications and products that include, but are not limited to, plastics and man-made fibers), consumer products (applications and products that include, but are not limited to detergents, cosmetics, and personal care products), fine chemicals (applications and products that include, but are not limited to, small molecules for exacting specifications and large molecules for exacting specifications), and biodiesel fuels (applications and products that include, but are not limited to, fuel and/or lubrication).

The methods disclosed herein confer numerous advantages over traditional synthetic organic chemistry methods and other synthetic methods known in the art. These methods improve the process of conducting synthetic organic chemistry by decreasing reaction time and increasing reaction yield; this decreases the resource intensive nature of conducting organic synthesis traditionally and decreases extensive purification techniques which makes the reaction significantly 'greener' (i.e. environmentally friendly).

More specifically, first, the methods provide for shorter reaction times. Literature reported reaction times are incredibly diverse. There exist reports of reactions that require only minutes to reach completion and reactions that require weeks to reach completion, with the majority of reactions requiring hours to days to reach completion. Nanoreactors accelerate synthetic organic reactions and thus subsequent reaction times are reduced. The degree to which nanoreactors accelerate reactions varies by reaction, but in general, traditionally conducted reactions that require a few days to reach completion are able to reach completion in minutes when conducted in nanoreactors, and reactions that require multiple days to reach completion under traditional methods reach completion in hours when conducted in nanoreactors.

Second, the methods disclosed herein also provide for higher reaction yields. With traditional methods, a 60% yield is generally accepted as a "good yield." For a multistep syntheses, that yield diminishes with each step. Multi-step synthesis is the linear, sequential, combination of a series of reactions required to produce a desired product. For example, for a five step synthesis where each step has a 75% yield, the overall yield of the end product is only 23.7%, with a 76.3% overall loss. On the other hand, nanoreactors greatly enhance synthetic organic reaction yields. Optimized synthetic organic reactions conducted in nanoreactors are capable of affording the desired product in quantitative (100%) yield. Even for reactions that are not optimized, a drastic improvement over the yield obtained from traditional synthetic reactions is observed. This is especially key for multistep syntheses, as higher reaction yield has an incredibly profound impact on multi-step synthesis. If nanoreactors are used for a multistep synthesis and each step yields 98%, the overall loss is only 9.6%.

Third, the methods disclosed herein also provide the benefit of accommodating new reactions that have never been reported. In a non-limiting example, the methods disclosed herein can be used to facilitate direct amidation reactions. Prior to this discovery, it was necessary to utilize a low yielding two-step process to form.

Fourth, minimizing or eliminating purification is another benefit of the methods disclosed herein. With traditional synthetic methods, even when conditions are optimal, most reactions fail to yield 100% pure product. When reactions inevitably stall, isolation of the desired product requires tedious, time consuming purification. On the other hand, optimized, quantitative yielding, synthetic organic reactions conducted in nanoreactors typically require minimal purification. These reactions typically only require filtration and evaporation of solvent.

Fifth, the methods disclosed herein utilize fewer resources than from traditional synthetic methods. In traditional methods, effort must be expended to maintain optimal conditions for product synthesis. For example, it may be necessary to maintain the reactor at a temperature exceeding 100° C. for the duration of the synthesis; a substantial amount of energy is required to heat, e.g., 1000 gallons of reaction mixture to 100° and to hold it at that temperature for, e.g., 36 hours. However, given the acceleration of reactions conducted in nanoreactors, the amount of energy used to conduct the reactions is greatly reduced. A substantial amount of energy is saved conducting a reaction at, e.g., 40° C. for 30 minutes (reaction temperature is usually decreased), rather than, e.g., at 80° C. for 24 hours as in traditional methods. Time savings are afforded as well. With the present methods, a reaction may reach completion with 100% product yield in 30 minutes rather than a reaction under traditional methods, where it may take 24 hours to prepare a crude product that requires another two days of purification to obtain the desired product.

Sixth, the methods disclosed herein provide the benefit over traditional methods of "green chemistry" (characterized by the American Chemical Society's definition of green chemistry as "principles [that] enable scientists and engineers to protect and benefit the economy, people and the planet by finding creative and innovative ways to reduce waste, conserve energy, and discover replacements for hazardous substances."). Green chemistry, for example, promotes the use of water as a solvent for synthetic reactions, however most organic reactants are insoluble in water, making this approach impractical. However, with the use of nanoreactors, quantitative yielding reactions require far less purification, which saves the use of copious amounts organic (non-green) solvents. And energy is saved through the use of typically decreased reactions temperatures and times. Moreover, the nanoreactors themselves are reusable.

Seventh, the methods disclosed herein can be used for commercial scale synthesis, which, while generally feasible using traditional synthetic organic chemistry methods, is not feasible with other methods in the art utilizing decreased reactor size.

EXAMPLES

The examples disclosed herein use the following definitions and abbreviations:

| Term | Abbreviation | Definition |
| --- | --- | --- |
| residue | R | The carbon bearing portion of a molecule. |
| nucleophile | Nu | A negatively charged species that seeks to covalently bond with an electrophile (positively charged species). |
| electrophile | E | A positively charged species that seeks to covalently bond with a nucleophile (negatively charged species). |

-continued

| Term | Abbreviation | Definition |
|---|---|---|
| leaving group | Lg | A species that is capable of breaking its covalent bond to the carbon residue. |
| base | | A negatively charged species that seeks to covalently bond with hydrogen atom. |
| alkyl | | An arrangement of saturated carbon atoms. |
| acyl | | An arrangement of carbon atoms preceded by a carbon-oxygen double bond. |
| aromatic | Ar | An arrangement of unsaturated carbon atoms. |

Example 1: Use of SOMS as Nanoreactors in Synthetic Organic Chemistry

SOMS (swellable organically modified silica), a silica-based adsorbent and absorbent material, possesses a number of properties that, in combination, makes it well suited for use as a nanoreactor and for use with the methods disclosed herein. SOMS absorbs organic molecules into nanoporous cavities, i.e. the nanoreactors. Upon absorption of organic molecules, SOMS swells 3-5 times its dry volume. Upon removal of organic molecules, SOMS assumes its original dry volume. Finally, SOMS are hydrophobic; water does not enter the central cavity and water synthesized in the cavity migrates out of the cavity.

Figure 2A:
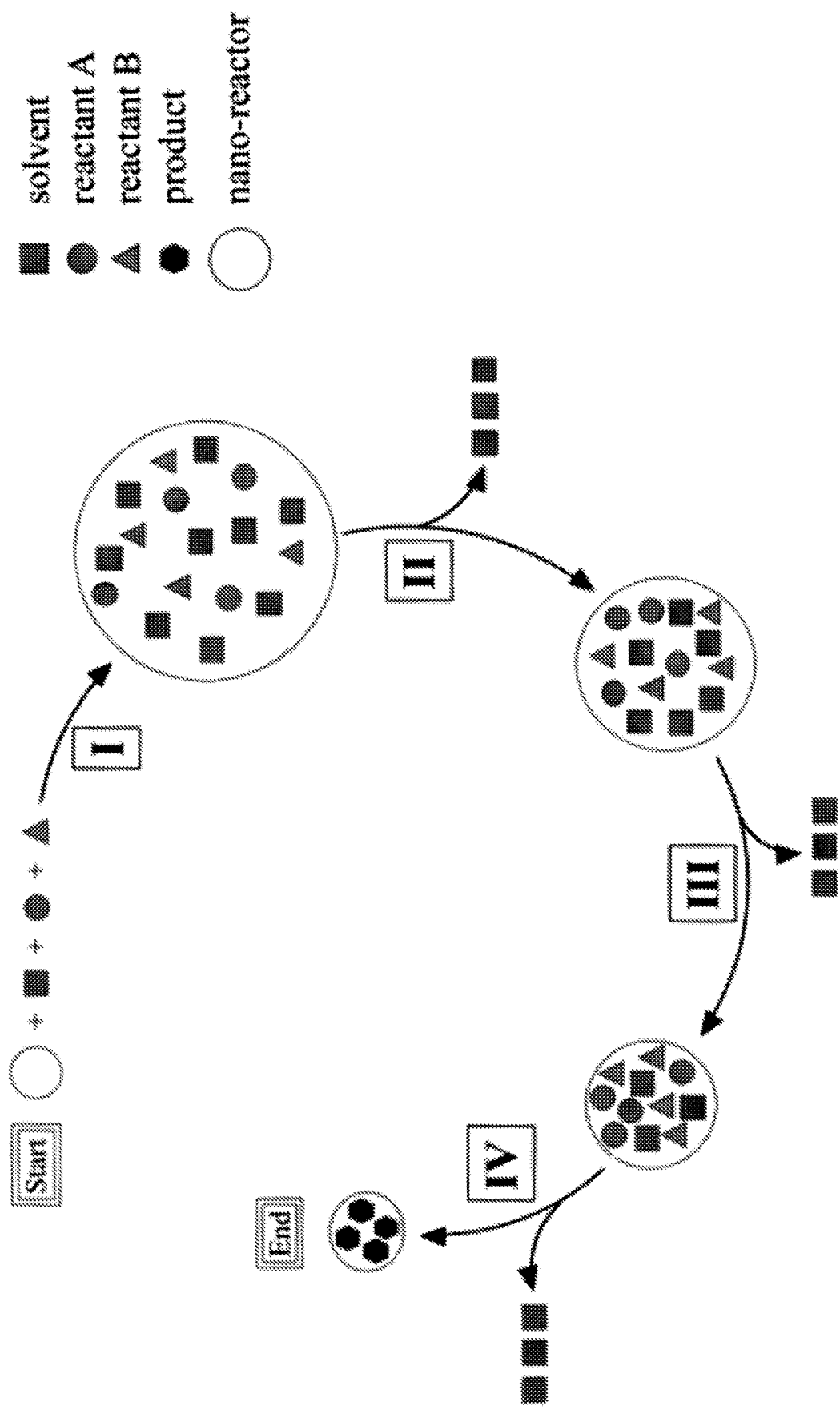
FIGS. 2A-2C. Schematic of a single close reaction (FIG. 2A) and multiple close reaction (FIG. 2B) conducted in nanoreactors. Schematic of post reaction product and nanoreactor recovery (FIG. 2C).

SOMS behaves as a nanoreactor when organic reactants are diluted with solvent and introduced to the SOMS, which causes the SOMS to swell (I), i.e. the nanoreactors to open, FIG. 2A. The nanoreactors collapses/contracts upon the selective evaporation of solvent (FIG. 2A, II-III), which drives the remaining reactants closer together. The nanoreactors are closed upon complete evaporation of solvent (FIG. 2A, IV) which leaves the reactants encapsulated in the collapsed nanoreactors, ensuring molecular reactivity. In this manner, SOMS nanoreactors can drive reactions to completion in mere minutes with reaction yields near 100%, which renders purification unnecessary, when used in place of traditional methods.

Figure 2B:
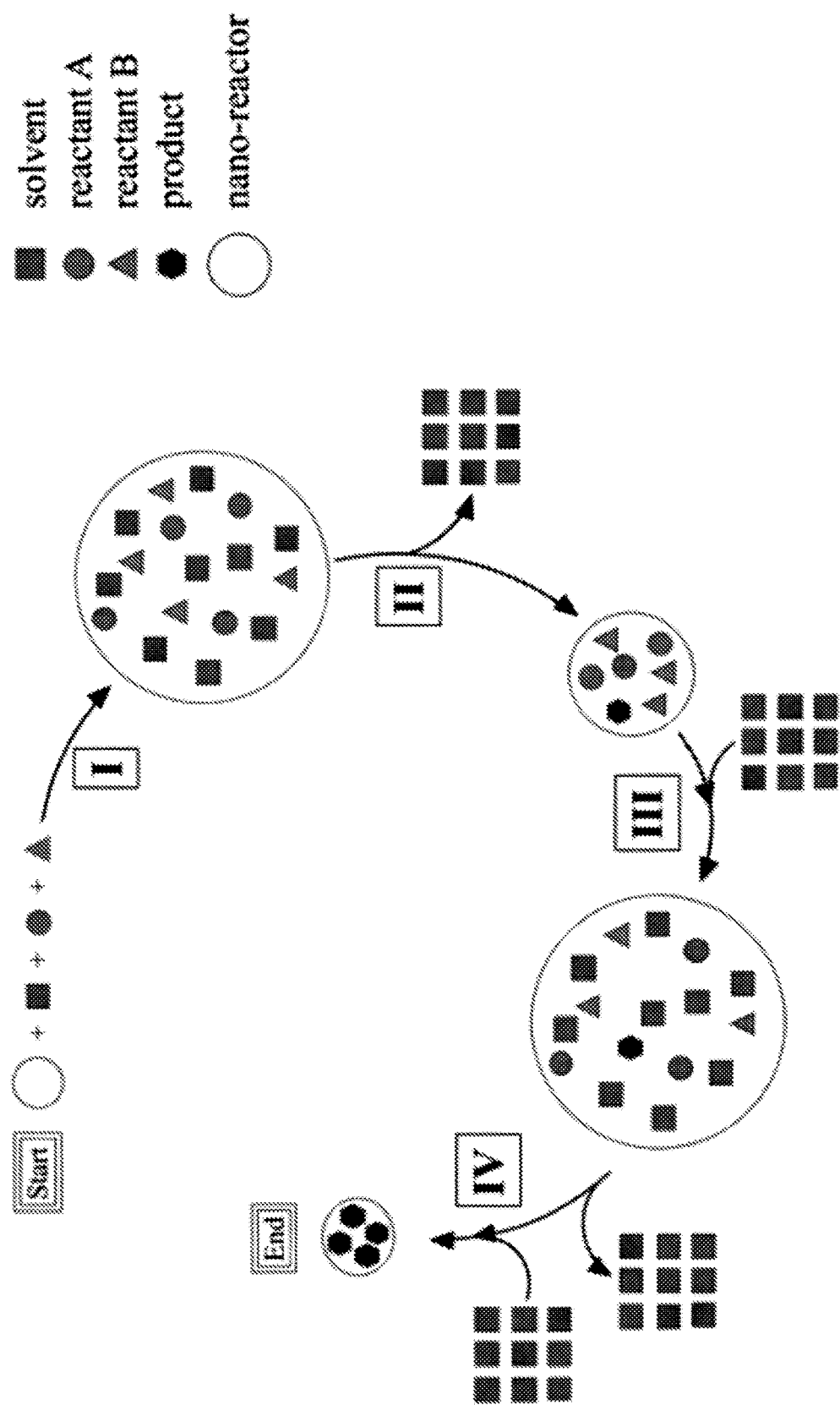

While some reactions are driven to completion in a single close of the nanoreactor, others are not. Reactions that are not driven to completion following a single close can be driven to completion upon the reintroduction of solvent to the nanoreactors, which causes the nanoreactors to swell/open (I), FIG. 2B. The nanoreactors collapse upon the selective evaporation of solvent (FIG. 2B II), which drives the reaction closer to completion. Repetitious addition and evaporation of solvent (FIG. 2B III-IV), 'flexes' the nanoreactors, effectively driving the reaction to completion.

Figure 3A:
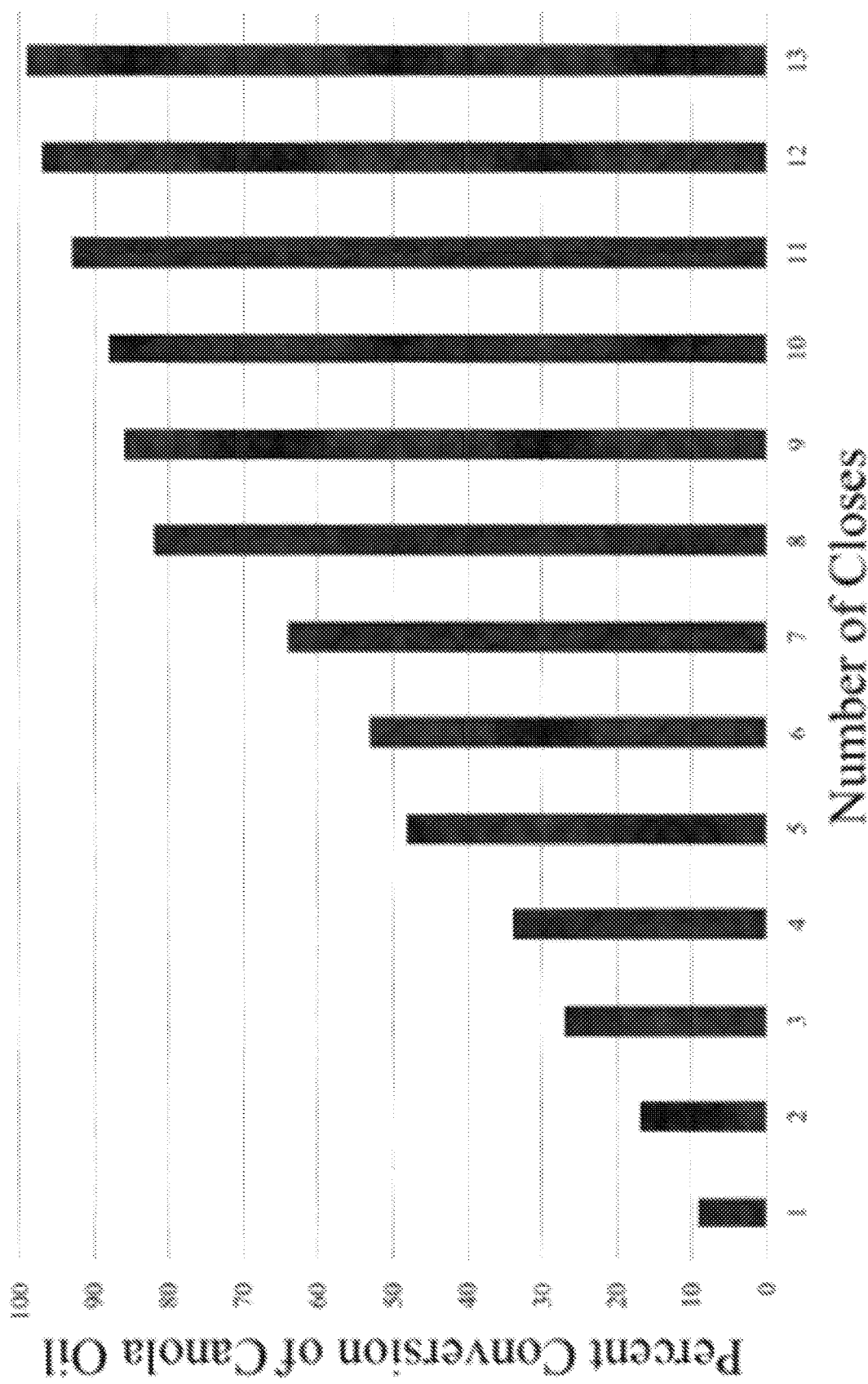
FIGS. 3A-3B.
Figure 3B:
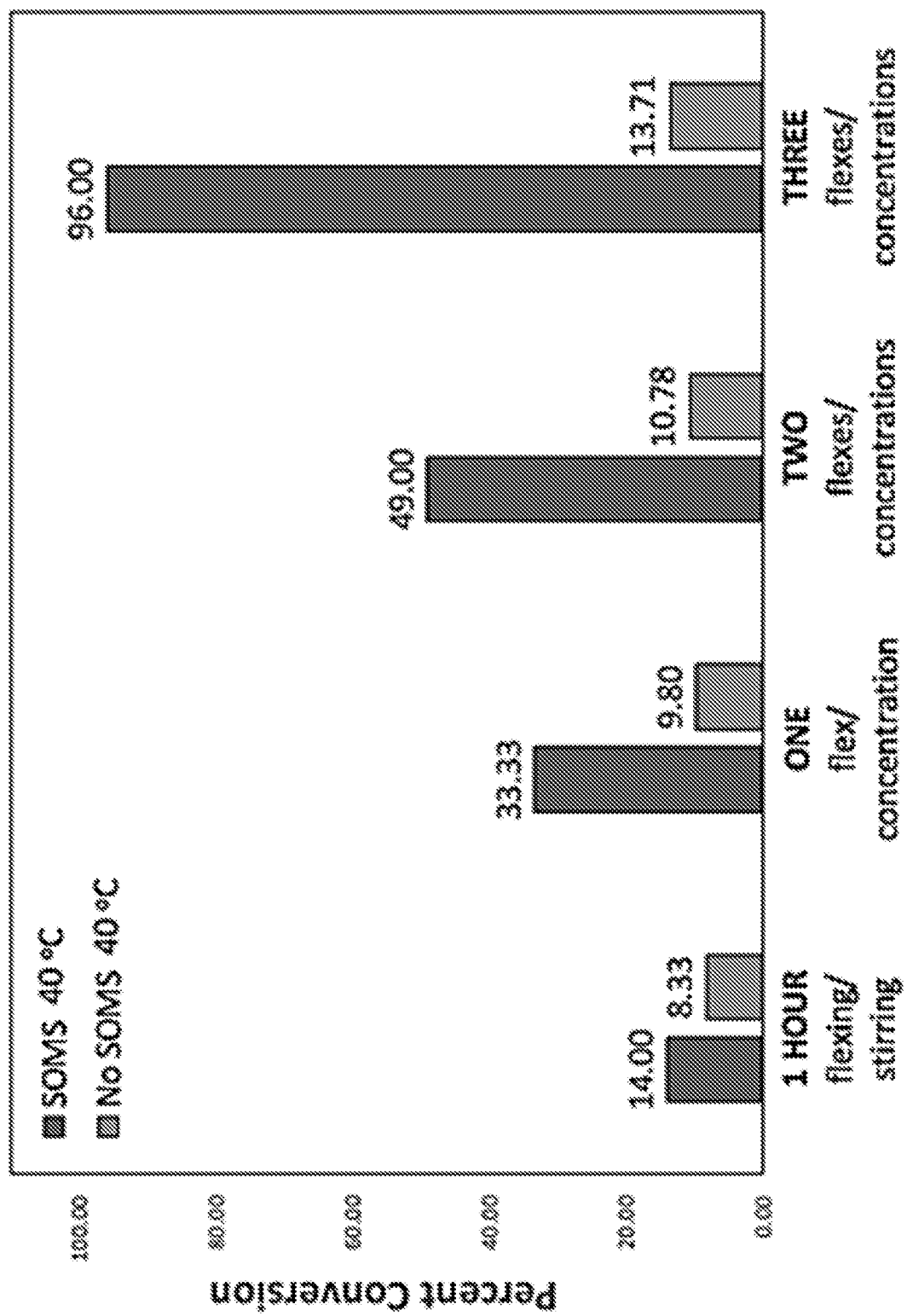

FIG. 3 provides exemplary results of reactions conducted using SOMS as a nanoreactor; FIG. 3A is a plot of the dependence on reaction progress with respect to the number of closes and FIG. 3B provides a plot comparing of the reaction progress in the presence and absence of nanoreactors.

Figure 2C:
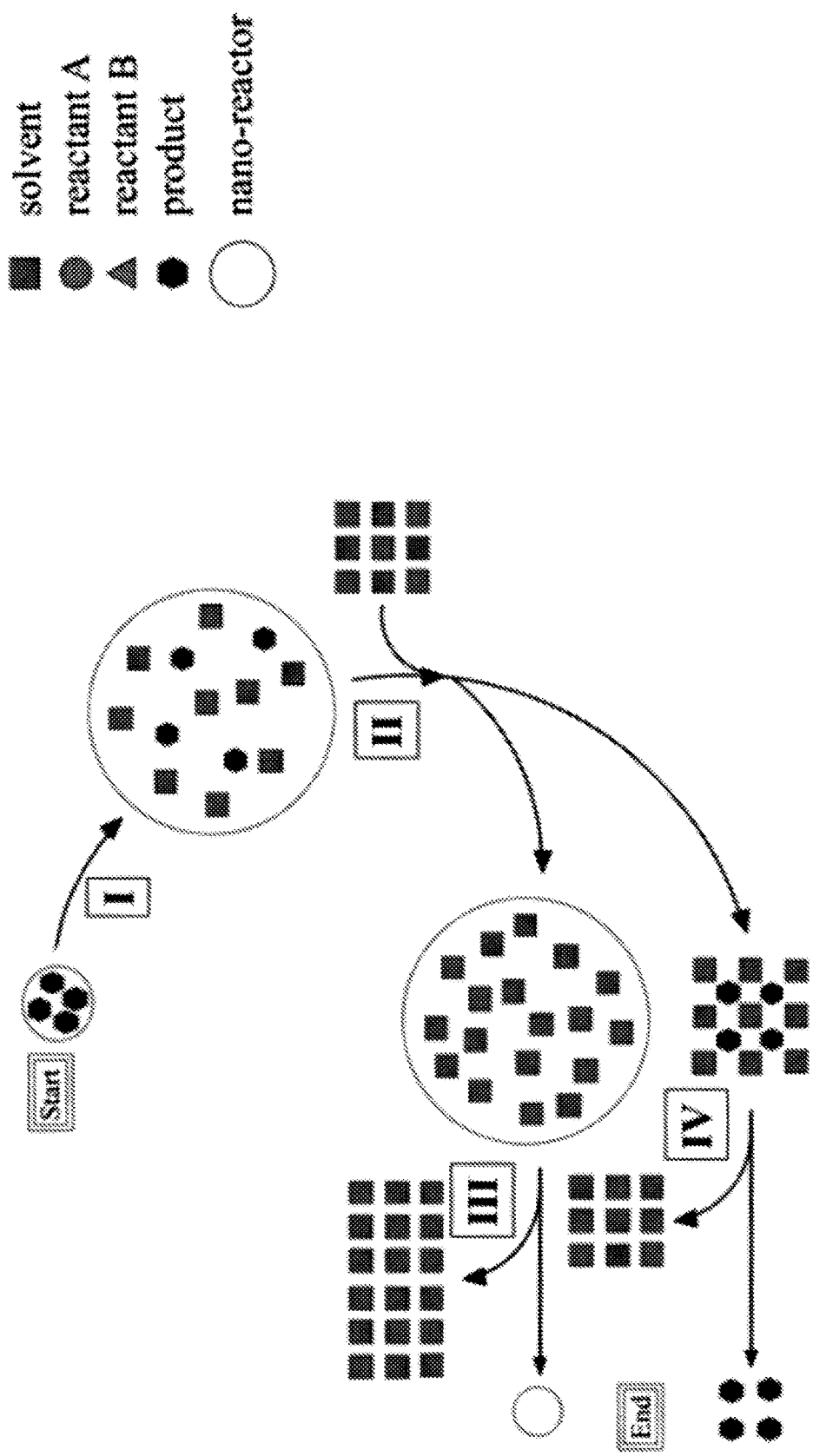
Figure 4:
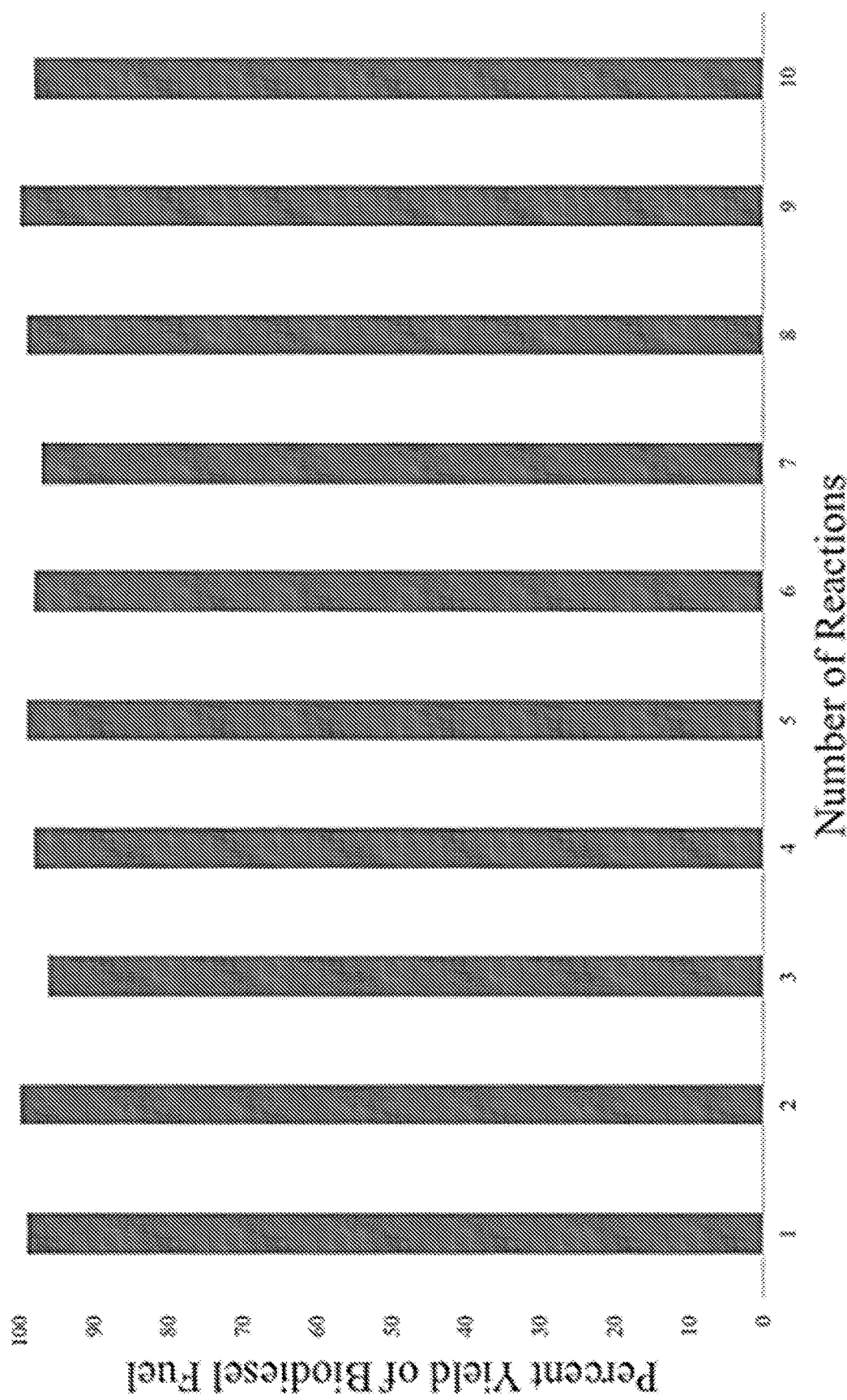
FIG. 4. Comparison of reaction yield (biodiesel fuel preparation) following sequential re-use of nanoreactors.

The desired product is easily recovered when the product laden nanoreactors are washed with solvent. Addition of solvent swells the product containing nanoreactors (I), FIG. 2C. Further addition of solvent with simultaneous filtration replaces product in the nanoreactors with solvent (FIG. 2C, II), effectively washing product from the nanoreactors. The SOMS is recovered following evaporation of solvent, sufficiently washed for re-use (FIG. 2C, III) while the desired product is recovered from the SOMS following evaporation (FIG. 2C, IV). The nanoreactors do not diminish reaction yield upon re-use, FIG. 4.

General Procedures:

Two methodologies may be used to achieve chemical reactivity inside SOMS nanoreactors, which produce two different reaction environments.

Heterogeneous conditions are achieved when the vessel containing SOMS nanoreactors, reactants, and solvent is, e.g., equipped with a reflux condenser and heated. Once system equilibrium is achieved, there is simultaneous evaporation and reintroduction of solvent. As such, at any given time, the physical state of the SOMS nanoreactors is not uniform. The SOMS nanoreactors could exist in a completely closed state, completely open state, or any variant between those two states.

Homogeneous conditions are achieved when the vessel containing SOMS nanoreactors, reactants, and solvent is, e.g., attached to a rotatory evaporator. The vessel is heated under reduced pressure, evaporating all of the solvent. Solvent is then reintroduced to the system, uniformly. As such, at any given time, the physical state of the SOMS nanoreactors is uniform. The SOMS nanoreactors begin in a completely open state and are driven uniformly to a completely closed state, and then completely opened, uniformly.

Experimentally, heterogeneous reaction conditions are capable of greatly enhancing reaction efficiency and completion when used in place of traditional synthetic methods. Homogeneous reaction conditions are capable of enhancing reaction efficiency and completion beyond that observed with heterogeneous methods.

Exemplary General Heterogeneous Synthesis Procedure: Dissolve reactant A and a minimal amount of solvent in a round bottom flask. Add reactant B, followed by (acid pre-treated or acetone washed) SOMS nanoreactors of any pore size, granular size, or swelling capacity. Add solvent until the SOMS nanoreactors are saturated, but not beyond saturation. Attach the round bottom flask to a reflux condenser. Heat the round bottom flask using a heating mantle. In instances where simultaneous evaporation of solvent and reactant may occur, the volatile reactant is reintroduced to the SOMS nanoreactors over the course of the reaction or water is used as a co-solvent. Following reaction completion, extract the contents from the SOMS nanoreactors using solid-liquid extraction and wash the SOMS nanoreactors with excess solvent. Recover the product following evaporation of solvent.

Exemplary General Homogeneous Synthesis Procedure: Dissolve reactant A and a minimal amount of solvent in a round bottom flask. Add reactant B, followed by (acid pre-treated or acetone washed) SOMS nanoreactors of any pore size, granular size, or swelling capacity. Add solvent until the SOMS nanoreactors are over saturated. Attach the round bottom flask to a rotatory evaporator. Heat the flask and evaporate the solvent in vacuo. Once solvent has been removed, over saturate the SOMS nanoreactors with solvent. Heat the flask and evaporate the solvent in vacuo, again— repeat these steps as necessary. In instances where simultaneous evaporation of solvent and reactant may occur, the volatile reactant is reintroduced to the SOMS nanoreactors with solvent during the over saturation step or water is used as a co-solvent. Following reaction completion, extract the contents from the SOMS nanoreactors using solid-liquid extraction and wash the SOMS nanoreactors with excess solvent. Recover the product following evaporation of solvent.

Exemplary General Flow Synthesis Procedure: Pre-load a column with solvent saturated (acid pre-treated or acetone washed) SOMS nanoreactors of any pore size, granular size, or swelling capacity. Dissolve reactant A and reactant B in a minimal amount of solvent, followed by SOMS nanoreactors. The reactant laden SOMS to the column end. Heat column to the desired temperature while simultaneously passing pre-heated solvent through the column. In instances where evaporation of a reactant may occur, the volatile reactant is introduced to the SOMS nanoreactors during pre-loading. Wait for product to elute the column. Recover the product following evaporation of solvent.

Example 2: Use of SOMS as Nanoreactors to Facilitate Nucleophilic Alkyl Substitution Reactions Scheme 2.0
Generic nucleophilic alkyl substitution reaction wherein R is a carbon bearing residue.

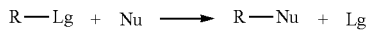

Nucleophilic alkyl substitution reactions are a sub-class of synthetic organic reactions, Scheme 2.0. These reactions feature the addition of a nucleophile (Nu) to a carbon residue (R) bearing an electrophilic alkyl leaving group (Lg). A new covalent bond between the nucleophile and electrophile is formed upon loss of the leaving group.

Specific Examples

Scheme 2.1 Synthesis of methoxymethylbenzene.

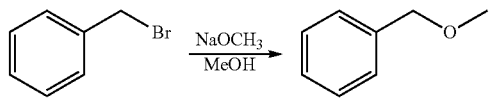

Synthesis of methoxymethylbenzene. Benzyl bromide (100.0 mg, 0.586 mmol) was dissolved in MeOH (10 mL) in a 50 mL round-bottom flask. SOMS (500.0 mg) were added followed by 80% NaOMe/MeOH (80%, v:v, 1 mL). The solvent was removed at 40° C. and 119 mbar. The SOMS were washed during filtration with MeOH (250 mL). The solution was suspended in 1M HCl (50 mL) and washed with $CH_2Cl_2$ (50 mL, 3×). The combined organic extracts were dried with $Na_2SO_4$ and concentrated in vacuo to afford methoxymethylbenzene as a clear oil (70.8 mg, 99%). $^1$H-NMR (400 MHz, CDCl$_3$) δ 7.44 (m, 2H), 7.35 (m, 2H), 7.30-7.40 (m, 3H), 4.50 (m, 2H), 3.22 (s, 3H).

Scheme 2.2
Synthesis of (prop-2-yn-1-yl)({6-[(prop-2-yn-1-yl)amino]hexyl})amine.

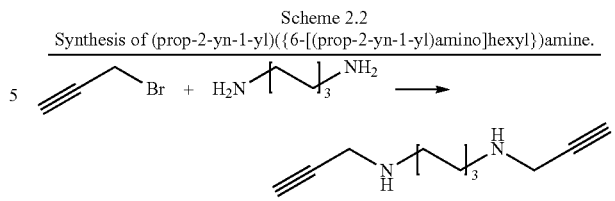

Synthesis of (prop-2-yn-1-yl)({6[(prop-2-yn-1-yl)amino]hexyl})amine. Hexanediamine (125.0 mg, 1.075 mmol) was dissolved in ethyl acetate (10 mL) in a 100 mL round-bottom flask. Propargyl bromide was added (255.9 mg, 2.150 mmol), followed by SOMS (1.0 g). The SOMS were saturated with ethyl acetate and heated at 60° C. for 24 hr. The SOMS were washed during filtration with ethyl acetate (300 mL). The solvent was removed in vacuo to afford (prop-2-yn-1-yl)({6-[(prop-2-yn-1-yl)amino]hexyl}amine as a clear oil (205.8 mg, 100%). $^1$H-NMR (400 MHz, CDCl$_3$) δ 3.06 (s, 4H), 2.80 (s, 2H), 2.56 (t, 4H), 1.32 (m, 1H), 1.39 (m, 1H), 1.28-1.43 (m, 8H).

Scheme 2.3 Synthesis of N-benzylaniline.

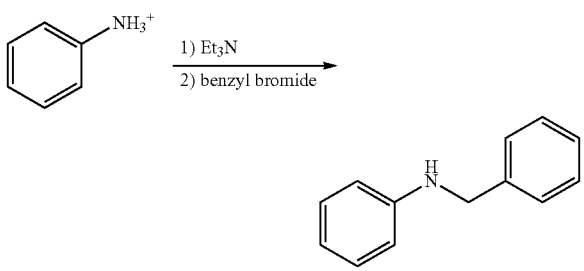

Synthesis of N-benzylaniline. Aniline hydrochloride (38.9 mg, 0.30 mmol) was dissolved in water (1.0 mL) in a 10 dram vial, followed by triethyl amine (30.4 mg, 0.30 mmol) was added. In a separate 100 mL round-bottom flask, benzyl bromide (50 mg, 0.30 mmol) and acetone (10 mL) was added, followed by SOMS (500 mg). The contents of the vial were added to the round-bottom flask. The acetone was removed using a rotary evaporator (325 mbar, 40° C.). Acetone (10 mL) was added and removed using a rotary evaporator (325 mbar, 40° C.). This step was repeated one additional time. The SOMS were washed during filtration with acetone (250 mL). The solvent was removed in vacuo to afford N-benzylaniline as an oil (54.9 mg, 100%). $^1$H-NMR (400 MHz, CDCl$_3$) δ 7.33 (m, 3H), 7.22 (m, 4H), 6.81 (t, 1H), 6.70 (t, 2H), 4.38 (s, 1H).

Scheme 2.4: Synthesis of (azidomethyl)benzene.

Synthesis of (azidomethyl)benzene. Benzyl bromide (100 mg, 0.58 mmol) was dissolved in dichloromethane ($CH_2Cl_2$, 3 mL) in a 100 mL round-bottom flask followed by SOMS (1.0 g). $CH_2Cl_2$ was removed in vacuo. In a separate flask, sodium azide (38.1 mg, 0.58 mmol) was dissolved in dimethyl formamide (DMF, 3.0 mL) and added to the round-bottom flask. $CH_2Cl_2$ (7.0 mL) was added to round-bottom flask and the flask was equipped with a reflux condenser and the solution was heated at 40° C. for 1 hour. The SOMS were washed during filtration with $CH_2Cl_2$ (150 mL) and the solvent was evaporated in vacuo to afford (azidomethyl) benzene as a off white solid (77.8 mg, 100%). $^1$H-NMR (400 MHz, $CDCl_3$) δ 7.38 (m, 5H), 5.87 (s, 2H).

Scheme 2.5: Synthesis of 1,8-diazidooctane.

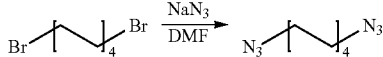

Synthesis of 1,8-diazidooctane. SOMS (1.0 g), was swelled with 1,8-dibromooctane (100.0 mg, 0.368 mmol) and acetone (5 mL). In a separate beaker, sodium azide (47.8 mg, 0.735 mmol) was dissolved in acetone (4 mL) and added to the round-bottom flask. Solvent was removed in vacuo. The SOMS were saturated, but not oversaturated with acetone (20 mL). The round-bottom flask was equipped with a reflux condenser and allowed to heat at 40° C. for 15 hrs. The SOMS were washed during filtration with acetone (150 mL) and the solvent was evaporated in vacuo to afford 1,8-diazidooctane as an off white solid (144.3 mg, 100%). $^1$H-NMR (400 MHz, $CDCl_3$) δ 4.01 (t, 4H), 1.98 (p, 4H), 1.37 (p, 4H), 1.28 (t, 2H).

Scheme 2.6: Synthesis of 1,4-diazidobutane.

Synthesis of 1,4-diazidobutane. SOMS (1.0 g), was swelled with 1,4-dibromobutane (100.0 mg, 0.435 mmol) and acetone (5 mL). In a separate beaker, sodium azide (56.5 mg, 0.865 mmol) was dissolved in acetone (4 mL) and added to the round-bottom flask. Solvent was removed in vacuo. The SOMS were saturated, but not oversaturated with acetone (20 mL). The round-bottom flask was equipped with a reflux condenser and allowed to heat at 40° C. for 15 hrs. The SOMS were washed during filtration with acetone (150 mL) and the solvent was evaporated in vacuo to afford 1,4-diazidobutane as an off white solid (93.4 mg, 100%). $^1$H-NMR (400 MHz, $CDCl_3$) δ 4.14 (t, 4H), 2.03 (t, 4H).

Scheme 2.7: Synthesis of 1,2-bis(2-azidoethoxy)ethane.

Synthesis of 1,2-bis(2-azidoethoxy)ethane. SOMS (1.0 g), was swelled with 1,2-bis(2-chloroethoxy)ethane (100.0 mg, 0.532 mmol) and acetone (5 mL). In a separate beaker, sodium azide (69.5 mg, 1.069 mmol) was dissolved in acetone (4 mL) and added to the round-bottom flask. Solvent was removed in vacuo. The SOMS were saturated, but not oversaturated with acetone (20 mL). The round-bottom flask was equipped with a reflux condenser and allowed to heat at 40° C. for 15 hrs. The SOMS were washed during filtration with acetone (150 mL) and the solvent was evaporated in vacuo to afford 1,2-bis(2-azidoethoxy)ethane as an off white solid (106.5 mg, 100%). $^1$H-NMR (400 MHz, $CDCl_3$) δ 4.14 (t, 4H), 3.99 (t, 4H), 3.71 (s, 2H).

Example 3: Use of SOMS as Nanoreactors to Facilitate Nucleophilic Acyl Substitution Reactions Scheme 3.0: Generic nucleophilic acyl substitution reaction wherein R is a carbon bearing residue.

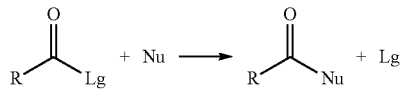

Nucleophilic acyl substitution reactions are a sub-class of synthetic organic reactions, Scheme 3.0. These reactions feature the addition of a nucleophile (Nu) to a carbon residue (R) bearing an electrophilic acyl leaving group (Lg). A new covalent bond between the nucleophile and electrophile is formed upon loss of the leaving group.

Specific Examples

Scheme 3.1: Synthesis of benzoyl chloride.

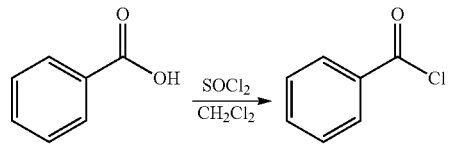

Synthesis of benzoyl chloride. Benzoic acid (100.0 mg, 0.819 mmol) was dissolved in $CH_2Cl_2$ (20 mL) in a 50 mL round-bottom flask. SOMS (1.0 g) were added and the solvent was removed in vacuo. A solution of thionyl chloride (974.2 mg, 8.190 mmol) in $CH_2Cl_2$ (10 mL) was added dropwise. The solvent was removed in vacuo. The SOMS were suspended in water (50 mL) for 20 min. The SOMS were filtered and allowed to dry overnight. The SOMS were washed during filtration with $CH_2Cl_2$ (200 mL) and the solvent removed in vacuo to afford as a clear liquid (115.1 mg, 100%). $^1$H-NMR (400 MHz, $CDCl_3$) δ 8.05 (m, 2H), 7.59 (m, 1H), 7.45 (m, 2H).

Scheme 3.2: Synthesis of methyl benzoate.

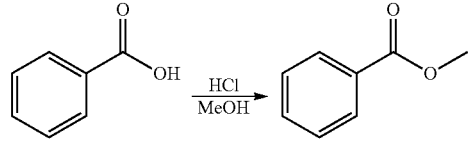

Synthesis of methyl benzoate. Benzoic acid (100.0 mg, 0.819 mmol) was dissolved in MeOH (5 mL) in a 50 mL round-bottom flask. HCl (4 N, 0.5 mL) was added followed by SOMS (1.0 g). The SOMS were saturated with MeOH and the reaction was heated at 60° C. for 24 hrs. The SOMS were washed during filtration with MeOH (250 mL). The solution was a saturated $NaHCO_3$ solution (250 mL) and washed with $CH_2Cl_2$ (100 mL, 3×). The combined organic extracts were dried with $Na_2SO_4$ and concentrated in vacuo to afford methyl benzoate as a white solid (110.4 mg, 99%). $^1$H-NMR (400 MHz, $CDCl_3$) δ 8.03 (m, 2H), 7.59 (m, 1H), 7.45 (m, 2H), 3.80 (s, 3H).

Scheme 3.3: Synthesis of methyl oleate.

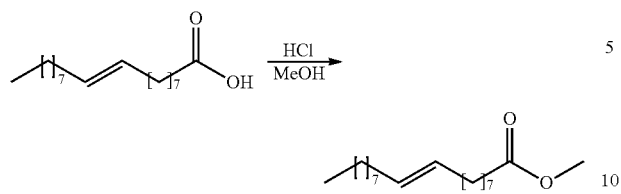

Synthesis of methyl oleate. Oleic acid (75.0 mg, 0.266 mmol) was dissolved in MeOH (5 mL) in a 50 mL round-bottom flask. HCl (4 N, 0.5 mL) was added followed by SOMS (1.0 g). The SOMS were saturated with MeOH and the reaction was heated at 60° C. for 24 hrs. The SOMS were washed during filtration with MeOH (250 mL). The solution was suspended in a saturated NaHCO$_3$ solution (250 mL) and washed with CH$_2$Cl$_2$ (100 mL, 3×). The combined organic extracts were dried with Na$_2$SO$_4$ and concentrated in vacuo to afford methyl oleate as an orange liquid (78.7 mg, 100%). $^1$H-NMR (400 MHz, CDCl$_3$) δ 5.33 (m, 1H), 5.28 (m, 2H), 3.60 (s, 3H), 2.25 (m, 2H), 1.91 (m, 2H), 1.55 (m, 2H), 1.43 (m, 2H), 1.38 (m, 2H), 1.24 (m, 6H), 1.20 (m, 20H).

Scheme 3.4: Synthesis of N-(4-methoxyhenyl)benzamide.

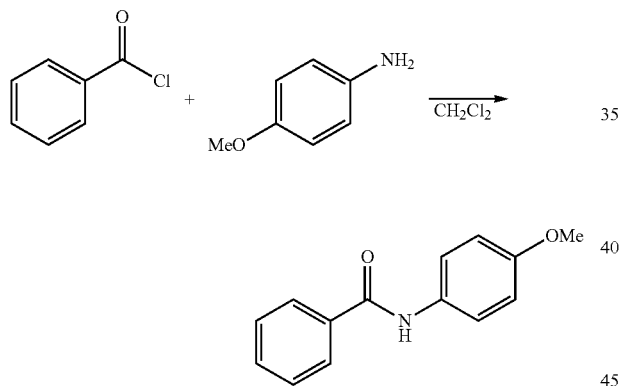

Synthesis of N-(4-methoxyphenyl)benzamide. Benzoyl chloride (140.7 mg, 1.0 mmol) and CH$_2$Cl$_2$ (15 mL) were added to a 100 mL round-bottom flask followed by SOMS (500 mg). p-Anisidine (123.1 mg, 1.0 mmol) was added to the round-bottom flask. CH$_2$Cl$_2$ was removed on the rotary evaporator (859 mbar, 40° C.). The SOMS were washed during filtration with CH$_2$Cl$_2$ (150 mL). The solution was concentrated in vacuo to afford N-(4-methoxyphenyl)benzamide (228 mg, 100%). $^1$H-NMR (400 MHz, CDCl$_3$) δ 8.0 (d, 2H), 7.52 (m, 5H), 7.22 (t, 2H), 7.01 (d, 1H).

Scheme 3.5: Synthesis of N,1-diphenylmethanimine.

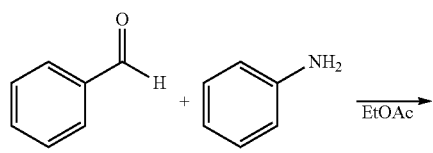

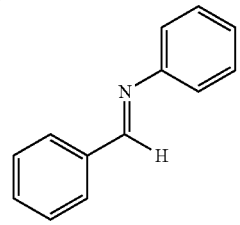

Synthesis of N,1-diphenylmethanimine. Dichloromethane (CH$_2$Cl$_2$, 10 mL), followed by benzaldehyde (113.9 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 30° C. for 2 hours. The SOMS were washed during filtration with EtOAc (150 mL) and the organic solution was dried with MgSO$_4$. The solution was decanted and the solvent was evaporated in vacuo to afford N,1-diphenylmethanimine as an off white solid (170.4 mg, 94%). $^1$H-NMR (400 MHz, CDCl$_3$) δ 8.79 (s, 1H), 8.19 (d, 2H), 7.51 (t, 2H), 7.45-7.46 (m, 4H), 7.32 (d, 2H).

Scheme 3.6: Synthesis of N-(3,5-dichlorophenyl)-1-phenylmethanimine.

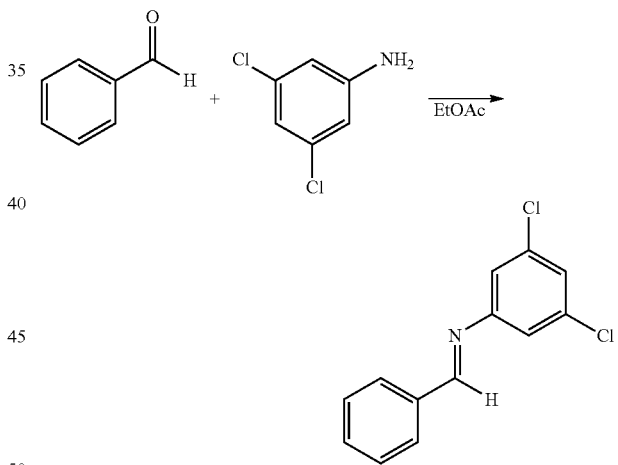

Synthesis of N-(3,5-dichlorophenyl)-1-phenylmethanimine. Dichloromethane (CH$_2$Cl$_2$, 10 mL), followed by benzaldehyde (113.9 mg, 1.0 mmol) and SOMS (1.0 g) were added to a 100 mL round-bottom flask. The solvent was removed in vacuo. In a 50 mL beaker, 3,5-dichloroaniline (162.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 23 hours. The SOMS were washed during filtration with EtOAc (150 mL) and the organic solution was dried with MgSO$_4$. The solution was decanted and the solvent was evaporated in vacuo to afford N-(3,5-dichlorophenyl)-1-phenylmethanimine as an off white solid (202.6 mg, 81%).

$^1$H-NMR (400 MHz, CDCl$_3$) δ 8.81 (s, 1H), 8.19 (d, 2H), 7.59 (s, 1H), 7.45-7.46 (m, 5H).

Scheme 3.7: Synthesis of N-(4-methoxyphenyl)-1-phenylmethanimine.

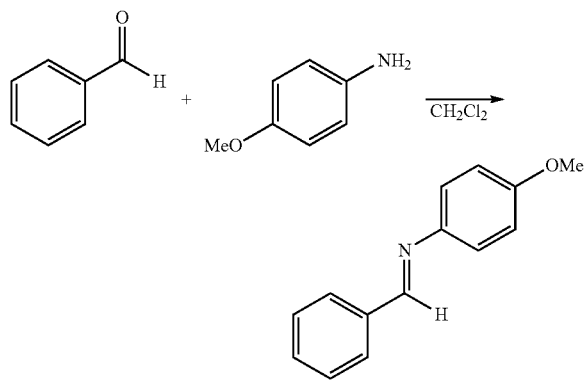

Synthesis of N-(4-methoxyphenyl)-1-phenylmethanimine. Dichloromethane (CH$_2$Cl$_2$, 10 mL), followed by benzaldehyde (113.9 mg, 1.0 mmol) and SOMS (1.0 g) were added to a 100 mL round-bottom flask. The solvent was removed in vacuo. In a 50 mL beaker, anisole (108.4 mg, 1 mmol) and CH$_2$Cl$_2$ (10 mL) were added. The contents of the beaker were added to the round-bottom flask and the CH$_2$Cl$_2$ was removed on the rotary evaporator (859 mbar, 40° C.). The previous step was repeated an additional three times. The SOMS were washed during filtration with CH$_2$Cl$_2$ (150 mL) and the organic solution was dried with MgSO$_4$. The solution was decanted and the solvent was evaporated in vacuo to afford N-(4-methoxyphenyl)-1-phenylmethanimine as an off white solid (211.3 mg, 100%). $^1$H-NMR (400 MHz, CDCl$_3$) δ 8.66 (s, 1H), 7.93 (d, 2H), 7.32 (t, 2H), 7.27-7.29 (m, 3H), 7.01 (d, 2H), 3.78 (s, 3H).

Scheme 3.8: Synthesis of N-(4-nitrophenyl)-1-phenylmethanimine.

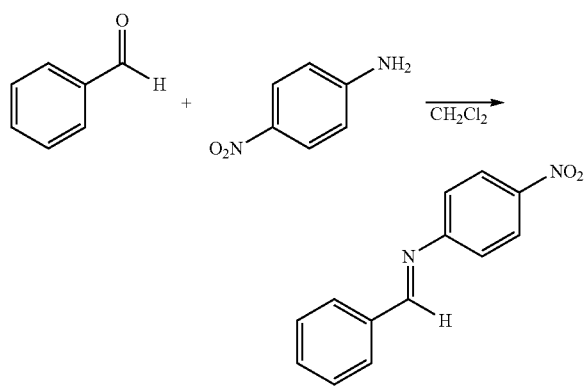

Synthesis of N-(4-nitrophenyl)-1-phenylmethanimine. Dichloromethane (CH$_2$Cl$_2$, 10 mL), followed by benzaldehyde (113.9 mg, 1.0 mmol) and SOMS (1.0 g) were added to a 100 mL round-bottom flask. The solvent was removed in vacuo. In a 50 mL beaker, 4-nitroaniline (138.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 22 hours. The SOMS were washed during filtration with EtOAc (150 mL) and the organic solution was dried with MgSO$_4$. The solution was decanted and the solvent was evaporated in vacuo to afford N-(4-nitrophenyl)-1-phenylmethanimine as an off white solid (90.5 mg, 40%). $^1$H-NMR (400 MHz, CDCl$_3$) δ 9.01 (s, 1H), 8.31 (d, 2H), 8.24 (d, 2H), 7.68 (d, 1H), 7.41 (d, 2H).

Scheme 3.9: Synthesis of 1-(4-nitrophenyl)-N-phenylmethanimine.

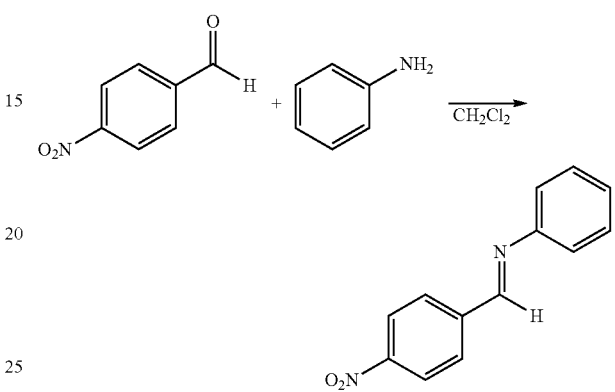

Synthesis of 1-(4-nitrophenyl)-N-phenylmethanimine. Dichloromethane (CH$_2$Cl$_2$, 10 mL), followed by 4-nitrobenzaldehyde (115.1 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the CH$_2$Cl$_2$ was removed on the rotary evaporator (859 mbar, 40° C.). The previous step was repeated an additional time. The SOMS were washed during filtration with CH$_2$Cl$_2$ (150 mL) and the organic solution was dried with MgSO$_4$. The solution was decanted and the solvent was evaporated in vacuo to afford 1-(4-nitrophenyl)-N-phenylmethanimine as an off white solid (214.9 mg, 95%).

Conversely, dichloromethane (CH$_2$Cl$_2$, 10 mL), followed by 4-nitrobenzaldehyde (115.1 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 1.5 hours. The SOMS were washed during filtration with EtOAc (150 mL) and the organic solution was dried with MgSO$_4$. The solution was decanted and the solvent was evaporated in vacuo to afford 1-(4-nitrophenyl)-N-phenylmethanimine as an off white solid (226.6 mg, 99%).

$^1$H-NMR (400 MHz, CDCl$_3$) δ 9.04 (s, 1H), 8.01 (d, 2H), 7.76 (d, 2H), 7.42-7.50 (m, 5H).

Scheme 3.10: Synthesis of 1-(4-methylphenyl)-N-phenylmethanimine.

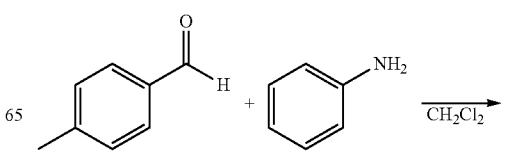

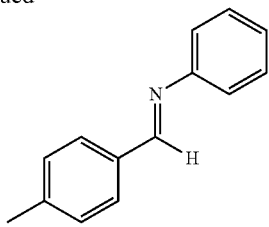

Synthesis of 1-(4-methylphenyl)-N-phenylmethanimine. Dichloromethane (CH$_2$Cl$_2$, 10 mL), followed by 4-methylbenzaldehyde (120.2 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the CH$_2$Cl$_2$ was removed on the rotary evaporator (859 mbar, 40° C.). The previous step was repeated an additional time. The SOMS were washed during filtration with CH$_2$Cl$_2$ (150 mL) and the organic solution was dried with MgSO$_4$. The solution was decanted and the solvent was evaporated in vacuo to afford 1-(4-methylphenyl)-N-phenylmethanimine as an off white solid (177.7 mg, 91%).

Conversely, dichloromethane (CH$_2$Cl$_2$, 10 mL), followed by 4-methylbenzaldehyde (120.2 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 2.5 hours. The SOMS were washed during filtration with EtOAc (150 mL) and the organic solution was dried with MgSO$_4$. The solution was decanted and the solvent was evaporated in vacuo to afford 1-(4-methylphenyl)-N-phenylmethanimine as an off white solid (189.4 mg, 97%).

$^1$H-NMR (400 MHz, CDCl$_3$) δ 8.89 (s, 1H), 7.51 (d, 2H), 7.41 (d, 1H), 7.36 (m, 4H), 7.16 (d, 2H), 2.28 (s, 3H).

Scheme 3.11: Synthesis of 1-(4-methoxyphenyl)-N-phenylmethanimine.

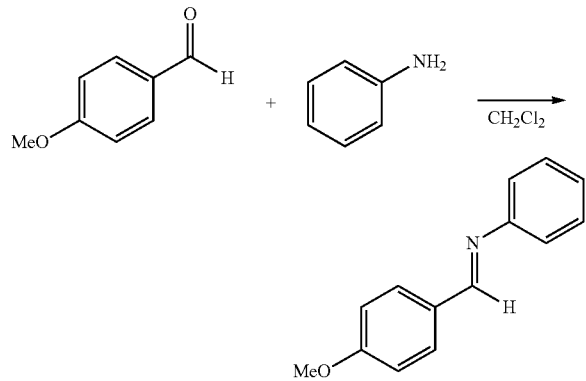

Synthesis of 1-(4-methoxyphenyl)-N-phenylmethanimine. Dichloromethane (CH$_2$Cl$_2$, 10 mL), followed by 4-methoxybenzaldehyde (136.1 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the CH$_2$Cl$_2$ was removed on the rotary evaporator (859 mbar, 40° C.). The previous step was repeated an additional time. The SOMS were washed during filtration with CH$_2$Cl$_2$ (150 mL) and the organic solution was dried with MgSO$_4$. The solution was decanted and the solvent was evaporated in vacuo to afford 1-(4-methyoxyphenyl)-N-phenylmethanimine as an off white solid (181.7 mg, 86%).

Conversely, dichloromethane (CH$_2$Cl$_2$, 10 mL), followed by 4-methoxybenzaldehyde (136.1 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 23 hours. The SOMS were washed during filtration with EtOAc (150 mL) and the organic solution was dried with MgSO$_4$. The solution was decanted and the solvent was evaporated in vacuo to afford 1-(4-methyoxyphenyl)-N-phenylmethanimine as an off white solid (196.5 mg, 93%).

$^1$H-NMR (400 MHz, CDCl$_3$) δ 8.77 (s, 1H), 7.55 (d, 2H), 7.31 (m, 4H), 7.26 (d, 1H), 7.16 (d, 2H), 3.88 (s, 3H).

Scheme 3.12: Synthesis of 1-(3-nitrophenyl)-N-phenylmethanimine.

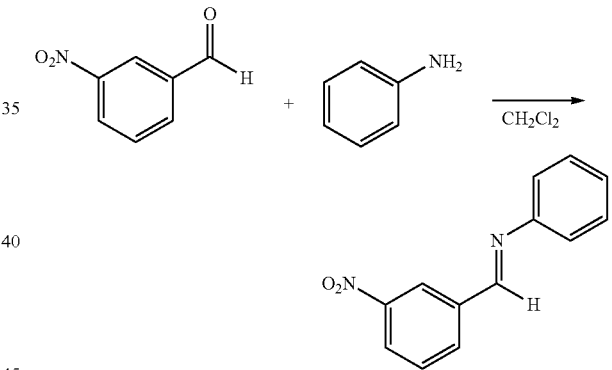

Synthesis of 1-(3-nitrophenyl)-N-phenylmethanimine. Dichloromethane (CH$_2$Cl$_2$, 10 mL), followed by 3-nitrobenzaldehyde (115.1 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the CH$_2$Cl$_2$ was removed on the rotary evaporator (859 mbar, 40° C.). The previous step was repeated an additional time. The SOMS were washed during filtration with CH$_2$Cl$_2$ (150 mL) and the organic solution was dried with MgSO$_4$. The solution was decanted and the solvent was evaporated in vacuo to afford 1-(3-nitrophenyl)-N-phenylmethanimine as an off white solid (185.5 mg, 82%).

Conversely, dichloromethane (CH$_2$Cl$_2$, 10 mL), followed by 3-nitrobenzaldehyde (115.1 mg, 1.0 mmol) and SOMS (1.0 g) were added to a 100 mL round-bottom flask. The solvent was removed in vacuo. In a 50 mL beaker, aniline (93.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 1.5 hours. The SOMS were washed during filtration with EtOAc (150 mL) and the organic solution was dried with MgSO$_4$. The solution was decanted and the solvent was evaporated in vacuo to afford 1-(3-nitrophenyl)-N-phenyl-methanimine as an off white solid (205.9 mg, 91%).

$^1$H-NMR (400 MHz, CDCl$_3$) δ 8.89 (s, 1H), 8.72 (s, 1H), 8.33 (d, 1H), 7.83 (d, 1H), 7.65 (m, 1H), 7.53 (m, 3H), 7.37 (d, 2H).

Scheme 3.13: Synthesis of N-(4-methoxyphenyl)-1-(4-nitrophenyl) methanimine.

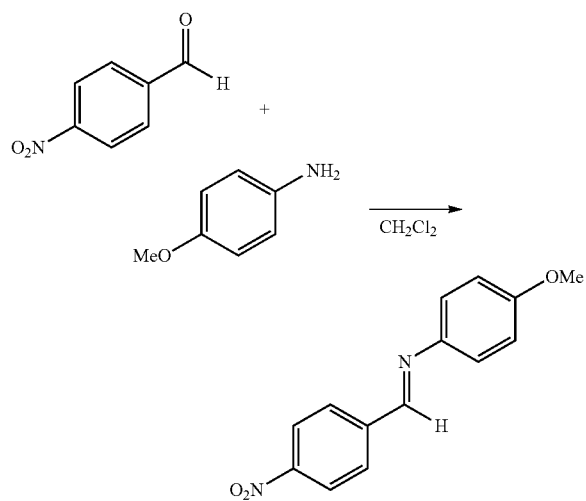

Synthesis of N-(4-methoxyphenyl)-1-(4-nitrophenyl)methanimine. Dichloromethane (CH$_2$Cl$_2$, 10 mL), followed by 4-nitrobenzaldehyde (115.1 mg, 1.0 mmol) and SOMS (1.0 g) were added to a 100 mL round-bottom flask. The solvent was removed in vacuo. In a 50 mL beaker, anisole (108.4 mg, 1 mmol) and CH$_2$Cl$_2$ (10 mL) were added. The contents of the beaker were added to the round-bottom flask and the CH$_2$Cl$_2$ was removed on the rotary evaporator (859 mbar, 40° C.). The previous step was repeated an additional time. The SOMS were washed during filtration with CH$_2$Cl$_2$ (150 mL) and the organic solution was dried with MgSO$_4$. The solution was decanted and the solvent was evaporated in vacuo to afford N-(4-methoxyphenyl)-1-(4-nitrophenyl) methanimine as an off white solid (256.3 mg, 100%). $^1$H-NMR (400 MHz, CDCl$_3$) δ 8.91 (s, 1H), 8.72 (s, 1H), 8.22 (d, 2H), 7.83 (d, 1H), 7.66 (d, 2H), 7.35 (d, 2H), 6.83 (d, 2H), 3.89 (s, 3H).

Scheme 3.14: Synthesis of N,1-bis(4-methoxyphenyl) methanimine.

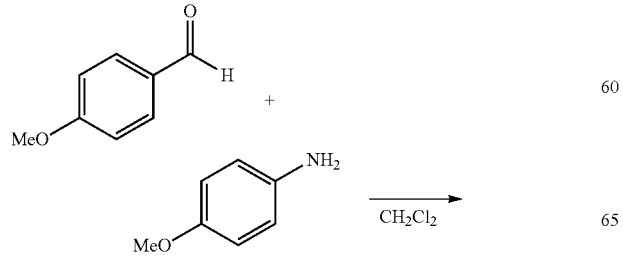

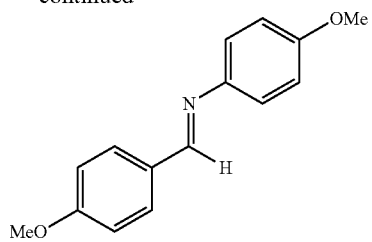

Synthesis of N, 1-bis(4-methoxyphenyl)methanimine. Dichloromethane (CH$_2$Cl$_2$, 10 mL), followed by 4-methoxybenzaldehyde (136.2 mg, 1.0 mmol) and SOMS (1.0 g) were added to a 100 mL round-bottom flask. The solvent was removed in vacuo. In a 50 mL beaker, anisole (108.4 mg, 1 mmol) and CH$_2$Cl$_2$ (10 mL) were added. The contents of the beaker were added to the round-bottom flask and the CH$_2$Cl$_2$ was removed on the rotary evaporator (859 mbar, 40° C.). The previous step was repeated an additional time. The SOMS were washed during filtration with CH$_2$Cl$_2$ (150 mL) and the organic solution was dried with MgSO$_4$. The solution was decanted and the solvent was evaporated in vacuo to afford N,1-bis(4-methoxyphenyl) methanimine as an off white solid (190.6 mg, 79%).

Conversely, dichloromethane (CH$_2$Cl$_2$, 10 mL), followed by 4-methoxybenzaldehyde (136.2 mg, 1.0 mmol) and SOMS (1.0 g) were added to a 100 mL round-bottom flask. The solvent was removed in vacuo. In a 50 mL beaker, anisole (108.4 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 23 hours. The SOMS were washed during filtration with EtOAc (150 mL) and the organic solution was dried with MgSO$_4$. The solution was decanted and the solvent was evaporated in vacuo to afford N,1-bis(4-methoxyphenyl)methanimine as an off white solid (236.5 mg, 98%).

$^1$H-NMR (400 MHz, CDCl$_3$) δ 8.61 (s, 1H), 7.40 (d, 2H), 7.20 (d, 2H), 7.13 (d, 2H), 7.04 (d, 2H), 3.83 (s, 3H), 3.78 (d, 3H).

Scheme 3.15: Synthesis of N-(3,5-dichlorophenyl)-1-(4-nitrophenyl) methanimine.

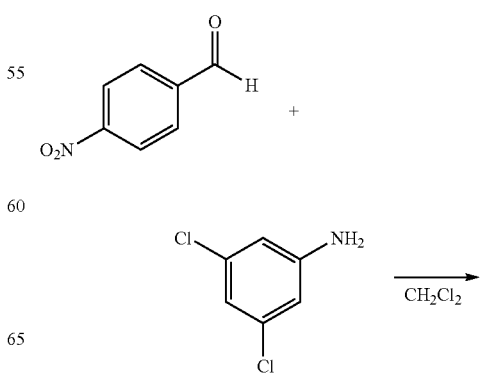

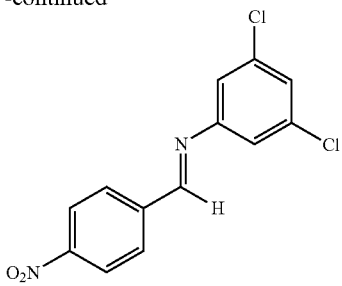

Synthesis of N-(3,5-dichlorophenyl)-1-(4-nitrophenyl) methanimine Dichloromethane (CH$_2$Cl$_2$, 10 mL), followed by 4-nitrobenzaldehyde (115.1 mg, 1.0 mmol) and SOMS (1.0 g) were added to a 100 mL round-bottom flask. The solvent was removed in vacuo. In a 50 mL beaker, 3,5-dichloroaniline (162.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 22 hours. The SOMS were washed during filtration with EtOAc (150 mL) and the organic solution was dried with MgSO$_4$. The solution was decanted and the solvent was evaporated in vacuo to afford N-(3,5-dichlorophenyl)-1-(4-nitrophenyl)methanimine as an off white solid (289.2 mg, 98%). $^1$H-NMR (400 MHz, CDCl$_3$) δ 9.10 (s, 1H), 8.01 (d, 2H), 7.78 (m, 3H), 7.51 (s, 2H).

Scheme 3.16: Synthesis of N-(3,5-dichlorophenyl)-1-(4-methoxyphenyl)methanimine.

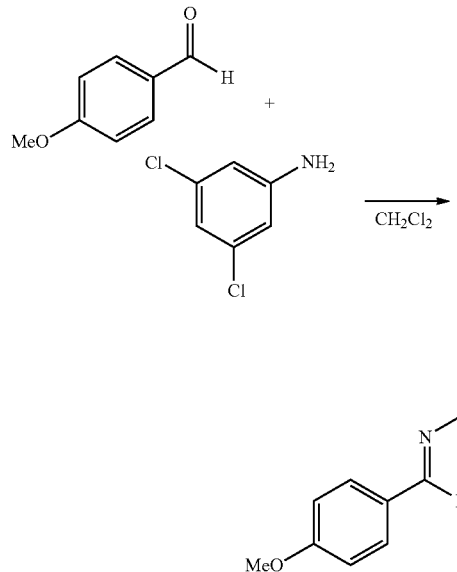

Synthesis of N-(3,5-dichlorophenyl)-1-(4-methoxyphenyl) methanimine Dichloromethane (CH$_2$Cl$_2$, 10 mL), followed by 4-methoxybenzaldehyde (136.2 mg, 1.0 mmol) and SOMS (1.0 g) were added to a 100 mL round-bottom flask. The solvent was removed in vacuo. In a 50 mL beaker, 3,5-dichloroaniline (162.1 mg, 1 mmol) and CH$_2$Cl$_2$ (10 mL) were added. The contents of the beaker were added to the round-bottom flask and the solvent was removed in vacuo. The previous step was repeated an additional three times to ensure mixing. Ethyl acetate (EtOAc, 2 mL) was added to the SOMS and the solution was attached to a reflux condenser and heated at 35° C. for 1.5 hours. The SOMS were washed during filtration with EtOAc (150 mL) and the organic solution was dried with MgSO$_4$. The solution was decanted and the solvent was evaporated in vacuo to afford N-(3,5-dichlorophenyl)-1-(4-methoxyphenyl)methanimine as an off white solid (249.3 mg, 89%). $^1$H-NMR (400 MHz, CDCl$_3$) δ 8.79 (s, 1H), 7.57 (d, 2H), 7.38 (s, 2H), 7.16 (m, 3H), 3.81 (s, 3H).

Scheme 3.17: Synthesis of methyl palmate.

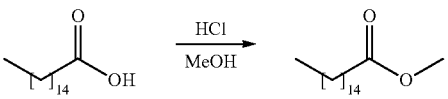

Synthesis of methyl palmate. In a 100 mL round-bottom flask, was added palmitic acid (1.0 g, 3.89 mol), dichloromethane (CH$_2$Cl$_2$, 20 mL), and SOMS (5.0 g). Dichloromethane was removed in vacuo. Hydrochloric acid (3N in methanol, 800 μL), followed by methanol (7.50 mL) were added until the SOMS became visibly saturated. The round-bottom flask was equipped with a reflux condenser and was heated at 65° C. for 24 hrs. The SOMS were washed during filtration with MeOH (350 mL) and the desired product, methyl palmate was recovered as an oil (1.1 g, 99%). $^1$H-NMR (400 MHz, CDCl$_3$) δ 3.69 (s, 3H), 2.32 (m, 2H), 1.64 (m, 2H), 1.27 (m, 24H), 0.90 (t, 3H).

Scheme 3.18: Synthesis of methyl 4-methoxybenzoate.

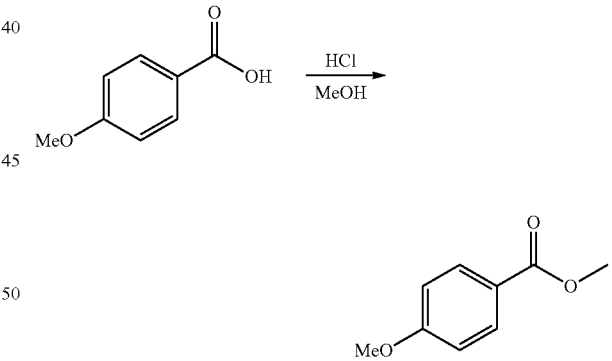

Synthesis of methyl 4-methoxybenzoate. In a 100 mL round-bottom flask, was added 4-methoxybenzoic acid (50.0 mg, 0.328 mmol) and ethylacetate (EtOAc, 10 mL). SOMS (100 mg) was added and the solvent was removed in vacuo. Hydrochloric acid (HCl, 82.16 μL, 4N in dioxane) was added dropwise followed by MeOH (1.5 mL). The round-bottom flask was equipped with a reflux condenser and allowed to heat at 40° C. for 1 hr. The SOMS were washed during extraction with MeOH (100 mL). Solvent was removed in vacuo and the desired product, methyl 4-methoxybenzoate, was recovered as an off white solid (54.4 mg, 100%). $^1$H-NMR (400 MHz, CDCl$_3$) δ 7.91 (d, 2H), 6.89 (d, 2H), 3.69 (s, 3H), 3.61 (s, 3H).

Scheme 3.19: Synthesis of methyl 4-nitrobenzoate.

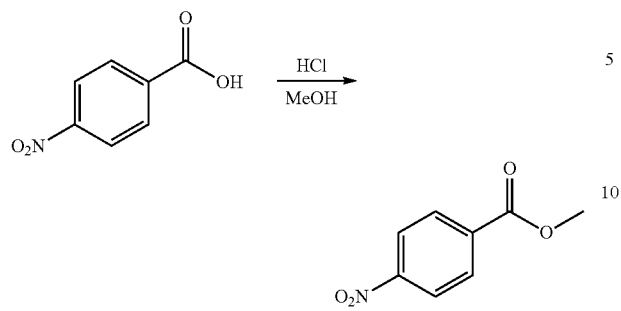

Synthesis of methyl 4-nitrobenzoate. In a 100 mL round-bottom flask, was added 4-nitrobenzoic acid (50.0 mg, 0.299 mmol) and diethylether (10 mL). SOMS (100 mg) was added and the solvent was removed in vacuo. Hydrochloric acid (HCl, 82.16 µL, 4N in dioxane) was added dropwise followed by MeOH (1.5 mL). The round-bottom flask was equipped with a reflux condenser and allowed to heat at 40° C. for 1 hr. The SOMS were washed during extraction with MeOH (100 mL). Solvent was removed in vacuo and the desired product, methyl 4-nitrobenzoate, was recovered as an off white solid (54.2 mg, 100%). $^1$H-NMR (400 MHz, CDCl$_3$) δ 8.25 (d, 2H), 8.18 (d, 2H), 3.79 (s, 3H).

Scheme 3.20: Synthesis of methyl 2,2-dimethylpropanoate.

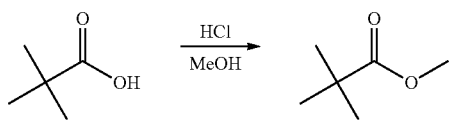

Synthesis of methyl 2,2-dimethylpropanoate. In a 100 mL round-bottom flask, was added pivalic acid (50.0 mg, 0.484 mmol) and diethylether (10 mL). SOMS (100 mg) was added and the solvent was removed in vacuo. Hydrochloric acid (HCl, 82.16 µL, 4N in dioxane) was added dropwise followed by MeOH (1.5 mL). The round-bottom flask was equipped with a reflux condenser and allowed to heat at 40° C. for 1.5 hr. The SOMS were washed during extraction with MeOH (100 mL). Solvent was removed in vacuo and the desired product, methyl 2,2-dimethylpropanoate, was recovered as an oil (56.2 mg, 100%). $^1$H-NMR (400 MHz, CDCl$_3$) δ 3.68 (s, 3H), 2.08 (s, 9H).

Scheme 3.21: Synthesis of cyclohexylacetate.

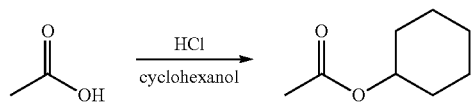

Synthesis of cyclohexylacetate. In a 100 mL round-bottom flask, was added acetic acid (500.0 mg, 0.833 mmol) and diethylether (10 mL). SOMS (100 mg) was added and the solvent was removed in vacuo. Hydrochloric acid (HCl, 82.16 µL, 4N in dioxane) was added dropwise followed by cyclohexanol (1.5 mL). The round-bottom flask was equipped with a reflux condenser and allowed to heat at 40° C. for 1.5 hr. The SOMS were washed during extraction with CH$_2$Cl$_2$ (100 mL). Solvent was removed in vacuo and the desired product, cyclohexylacetate, was recovered as an oil (118.2 mg, 100%). $^1$H-NMR (400 MHz, CDCl$_3$) δ 3.70 (m, 1H), 2.07 (s, 3H), 1.89 (m, 4H), 1.74 (m, 4H), 1.24 (m, 2H).

Scheme 3.22: Synthesis of cyclohexyl 4-nitrobenzoate.

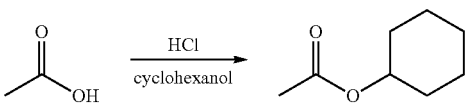

Synthesis of cyclohexyl 4-nitrobenzoate. In a 100 mL round-bottom flask, was added acetic acid (50.0 mg, 0.299 mmol) and diethylether (10 mL). SOMS (100 mg) was added and the solvent was removed in vacuo. Hydrochloric acid (HCl, 82.16 µL, 4N in dioxane) was added dropwise followed by cyclohexanol (46.7 µL, 0.488 mmol). The round-bottom flask was equipped with a reflux condenser and allowed to heat at 40° C. for 12 hr. The SOMS were washed during extraction with CH$_2$Cl$_2$ (100 mL). Solvent was removed in vacuo and the desired product, cyclohexyl 4-nitrobenzoate, was recovered as an oil (74.5 mg, 100%). $^1$H-NMR (400 MHz, CDCl$_3$) δ 8.83 (d, 2H), 8.25 (d, 2H), 3.61 (m, 1H), 1.89 (m, 4H), 1.75 (m, 4H), 1.38 (m, 2H).

Scheme 3.23: Synthesis of cyclohexyl 2,2-dimethylpropanoate.

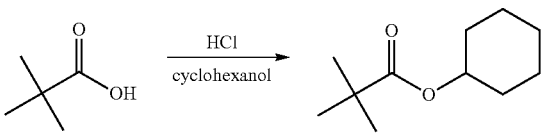

Synthesis of cyclohexyl 2,2-dimethylpropanoate. In a 100 mL round-bottom flask, was added pivalic acid (50.0 mg, 0.484 mmol) and diethylether (10 mL). SOMS (100 mg) was added and the solvent was removed in vacuo. Hydrochloric acid (HCl, 82.16 µL, 4N in dioxane) was added dropwise followed by cyclohexanol (46.7 µL, 0.488 mmol). The round-bottom flask was equipped with a reflux condenser and allowed to heat at 40° C. for 12 hr. The SOMS were washed during extraction with CH$_2$Cl$_2$ (100 mL). Solvent was removed in vacuo and the desired product, cyclohexyl 2,2-dimethylpropanoate, was recovered as an oil (89.2 mg, 100%). $^1$H-NMR (400 MHz, CDCl$_3$) δ 4.74 (m, 1H), 3.68 (s, 9H), 1.87 (m, 4H), 1.73 (m, 4H), 1.39 (m, 2H).

Scheme 3.24: Synthesis of methyl acetate.

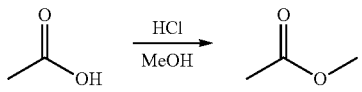

Synthesis of methylacetate. In a 100 mL round-bottom flask, was added acetic acid (500.0 mg, 0.833 mmol) and diethylether (10 mL). SOMS (100 mg) was added and the solvent was removed in vacuo. Hydrochloric acid (HCl, 82.16 µL, 4N in dioxane) was added dropwise followed by methanol (4.5 mL). The round-bottom flask was equipped with a reflux condenser and allowed to heat at 40° C. for 12 hr. The SOMS were washed during extraction with CH$_2$Cl$_2$ (100 mL). Solvent was removed in vacuo and the desired product, methylacetate, was recovered as an oil (61.7 mg, 100%). $^1$H-NMR (400 MHz, CDCl$_3$) δ 3.67 (s, 3H), 1.03 (s, 3H).

Scheme 3.23: Synthesis of cyclohexylbenzoate.

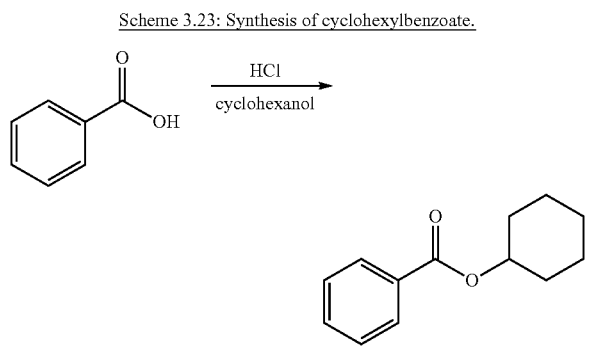

Synthesis of cyclohexylbenzoate. In a 100 mL round-bottom flask, was added benzoic acid (500.0 mg, 0.445 mmol) and diethylether (10 mL). SOMS (100 mg) was added and the solvent was removed in vacuo. Hydrochloric acid (HCl, 111.5 µL, 4N in dioxane) was added dropwise followed by cyclohexanol (1.5 mL). The round-bottom flask was equipped with a reflux condenser and allowed to heat at 40° C. for 12 hr. The SOMS were washed during extraction with $CH_2Cl_2$ (100 mL). Solvent was removed in vacuo and the desired product, cyclohexylbenzoate, was recovered as an oil (13.6 mg, 15%). $^1$H-NMR (400 MHz, $CDCl_3$) δ 8.05 (d, 2H), 7.51 (t, 1H), 7.43 (t, 2H), 4.99 (m, 1H), 1.86 (m, 4H), 1.70 (m, 4H), 1.41 (m, 2H).

Scheme 3.26: Synthesis of Boc-Trp-OMe.

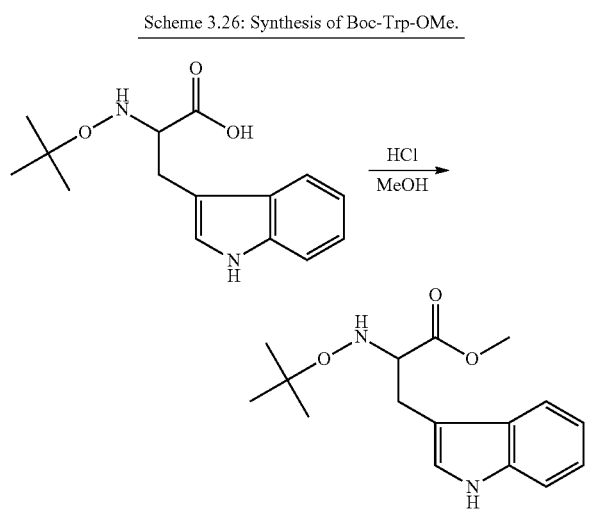

Synthesis of Boc-Trp-OMe Boc anhydride (1.0 g, 4.58 mmol), water (8.0 mL), triethyl amine ($Et_3N$, 1.0 mL), and $H_2N$-Trp-OMe hydrochloride (2.0 g, 7.85 mmol) were combined in a 150 mL round-bottom flask. Dimethylformamide (DMF, 4.0 mL) was added, followed by SOMS (10 g). The round-bottom flask was equipped with a reflux condenser and allowed to heat at 60° C. for 18 hrs. The SOMS were washed during extraction with ethyl acetate (EtOAc, 100 mL). The resulting solution as combined with water (100 mL) in a separatory funnel. The organic layer was removed and washed with water (100 mL, 3×). The organic layer was washed with HCl (1.0 M, 100 mL, 3×) and dried over $Na_2SO_4$. The solution was decanted and solvent was removed in vacuo to afford Boc-Trp-OMe as an off white solid (2.43 g, 100%).

Conversely, Boc-Trp-OH (1.0 g, 3.286 mmol) was dissolved in methanol (30 mL) in a 500 mL round-bottom flask. Hydrocholoric acid (4N in dioxane, 100 µL) was added followed by SOMS (20 g). The methanol was removed on the rotary evaporator (119 mbar, 40° C.). Methanol (50 mL) was added and removed on the rotary evaporator (119 mbar, 40° C.). Methanol (50 mL) was added and removed on the rotary evaporator (119 mbar, 40° C.). SOMS was washed during extraction with $CH_2Cl_2$ (200 mL). The organic layer was washed with HCl (1 M, 100 mL, 3×_followed by NaOH (1 M, 100 mL, 3×). The organic layer was dried with $Na_2SO_4$ and concentrated in vacuo to afford Boc-Trp-OMe as an off white solid (2.43 g, 100%).

$^1$H-NMR (400 MHz, $CDCl_3$) δ 8.01 (s, 1H), 7.49 (d, 1H), 7.30 (d, 1H), 7.18 (t, 1H), 7.05 (t, 1H), 6.94 (d, 1H), 4.55 (d, 1H), 3.61 (s, 3H), 3.22 (d, 2H), 1.37 (s, 3H).

Example 4: Use of SOMS as Nanoreactors to Facilitate Electrophilic Aromatic Substitution Reactions

Scheme 4.0: Generic electrophilic aromatic substitution reaction.

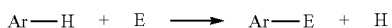

Electrophilic aromatic substitution reactions are a subclass of synthetic organic reactions, Scheme 4.0. These reactions feature the substitution of an aromatic hydrogen atom by an electrophile. A new covalent bond between the electrophile and the aromatic molecule is formed followed by loss of a hydrogen atom.

Specific Examples

Scheme 4.1: Synthesis of methyl N-methylimidazole-2-carboxylate.

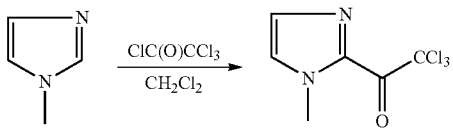

Synthesis of methyl N-methylimidazole-2-carboxylate N-methylimidazole (100.0 mg, 1.218 mmol) was diluted in $CH_2Cl_2$ (15 mL) in a 100 mL round-bottom flask. Methyl chloroformate (126.6 mg, 1.334 mmol) was added, followed by SOMS (1.5 g). The solvent was removed at 40° C. and 719 mbar. A solution of methyl chloroformate (122.6 mg) in $CH_2Cl_2$ was added to the round-bottom flask followed by solvent removal at 40° C. and 719 mbar. This cycle was repeated three more times for a total of five times. The SOMS were washed during filtration with $CH_2Cl_2$ (300 mL). The solution was suspended in a saturated $NaHCO_3$ solution (250 mL) and washed with $CH_2Cl_2$ (100 mL, 3×). The combined organic extracts were dried with $Na_2SO_4$ and concentrated in vacuo to afford methyl N-methylimidazole-2-carboxylate as an off white solid (167.3 mg, 98%). $^1$H-NMR (400 MHz, $CDCl_3$) δ 7.24 (d, 1H), 7.08 (d, 1H), 3.70 (s, 3H), 3.68 (s, 3H).

Example 5: Use of SOMS as Nanoreactors to Facilitate Nucleophilic Aromatic Addition Reactions Scheme 5.0: Generic nucleophilic aromatic addition reaction.

Nucleophilic aromatic addition reactions are a sub-class of synthetic organic reactions, Scheme 5.0. These reactions feature the substitution of an aromatic hydrogen atom by a nucleophile. A new covalent bond between the nucleophile and the aromatic molecule is formed followed by loss of a hydrogen atom.

Example 6: Use of SOMS as Nanoreactors to Facilitate Cycloaddition Reactions Scheme 6.0: Generic nucleophilic aromatic addition reaction.

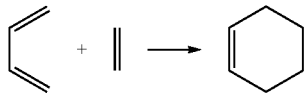

Cycloaddition reactions are a sub-class of synthetic organic reactions, Scheme 6.0. These reactions feature the addition of a poly-unsaturated carbon bearing residue to an unsaturated carbon bearing molecule such that new covalent carbon-carbon bonds are formed.

Specific Examples

Scheme 6.1: Synthesis of 5,6-dimethoxy-1,3,3a,4,7,7a-hexahydro-2-benzofuran-1,3-dione.

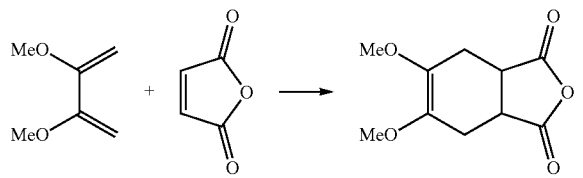

Synthesis of 5,6-dimethoxy-1,3,3a,4,7,7a-hexahydro-2-benzofuran-1,3-dione. 2,3-dimethylbutadiene (150.0 mg, 1.314 mmol) was diluted with $CH_2Cl_2$ (10 mL) in a 25 mL round-bottom flask. 2,5-dihydrofuran; furan-2,5-dione (128.8 mg, 1.314 mmol) was added followed by SOMS (1.0 g). Solvent was removed at 40° C. and 719 mbar. $CH_2Cl_2$ (10 mL) was added and the solvent removed at 40° C. and 719 mbar. This was repeated six more times, for a total of eight times. The SOMS were washed during filtration with $CH_2Cl_2$ (300 mL). Solvent was removed in vacuo to afford 5,6-dimethoxy-1,3,3a,4,7,7a-hexahydro-2-benzofuran-1,3-dione as an off white solid (278.8 mg, 100%). $^1$H-NMR (400 MHz, $CDCl_3$) δ 3.70 (s, 6H), 2.97 (m, 2H), 2.66 (m, 4H).

Scheme 6.2: Synthesis of 1-benzyl-4-(2-phenylethyl)-1H-1,2,3-triazole.

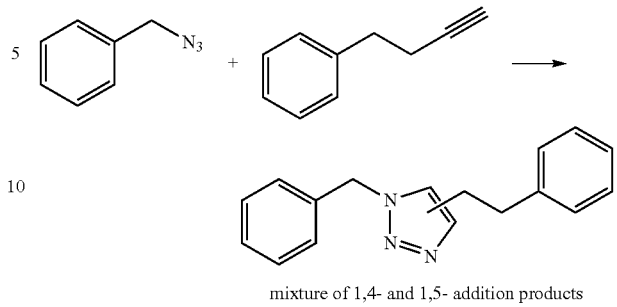

mixture of 1,4- and 1,5- addition products

Synthesis of 1-benzyl-4-(2-phenylethyl)-1H-1,2,3-triazole. Phenylbutyne (75.0 mg, 0.58 mmol) was dissolved in dichloromethane ($CH_2Cl_2$, 10 mL) in a 100 mL round-bottom flask. SOMS (1.0 g) was added to the flask. A solution of (azidomethyl)benzene (77.0 mg, 0.58 mmol) in $CH_2Cl_2$ (10 mL) was added to the round-bottom flask and the $CH_2Cl_2$ was removed in vacuo until the SOMS was saturated, but not oversaturated. The round-bottom flask was equipped with a reflux condenser and heated at 60° C. for 17 hours. The SOMS were washed during filtration with $CH_2Cl_2$ (100 mL). The solvent was removed in vacuo to afford 1-benzyl-4-(2-phenylethyl)-1H-1,2,3-triazole as an off white solid (61.1 mg, 40%). $^1$H-NMR (400 MHz, $CDCl_3$) δ 7.39 (m, 3H), 7.27 (m, 2H), 7.20 (m, 1H), 7.18 (m, 2H), 7.07 (m, 2H), 6.99 (s, 1H), 5.22 (s, 2H), 3.06 (t, 2H), 2.80 (t, 2H).

Scheme 6.3: Synthesis of 4-[2-(3-methylphenyl)ethyl]-1-[(3-methylphenyl)methyl]-1H-1,2,3-triazole.

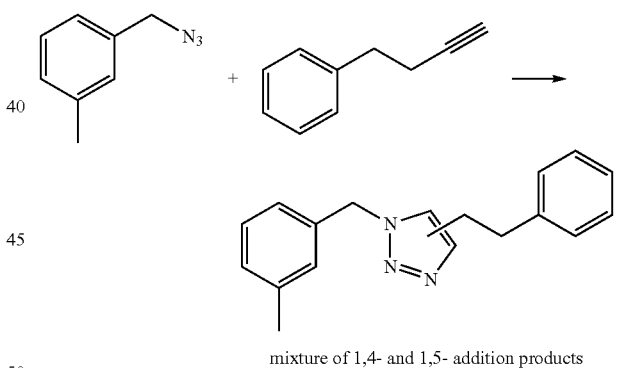

mixture of 1,4- and 1,5- addition products

Synthesis of 4-[2-(3-methylphenyl)ethyl]-1-[(3-methylphenyl)methyl]-1H-1,2,3-triazole. Phenylbutyne (75.0 mg, 0.58 mmol) was dissolved in dichloromethane ($CH_2Cl_2$, 10 mL) in a 100 mL round-bottom flask. SOMS (1.0 g) was added to the flask. A solution of 1-(azidomethyl)-3-methylbenzene (85.4 mg, 0.58 mmol) in $CH_2Cl_2$ (10 mL) was added to the roud=bottom flask and the $CH_2Cl_2$ was removed in vacuo until the SOMS was saturated, but not oversaturated. The round-bottom flask was equipped with a reflux condenser and heated at 60° C. for 17 hours. The SOMS were washed during filtration with $CH_2Cl_2$ (100 mL). The solvent was removed in vacuo to afford 4-[2-(3-methylphenyl)ethyl]-1-[(3-methylphenyl)methyl]-1H-1,2,3-triazole as an off white solid (64.2 mg, 38%). $^1$H-NMR (400 MHz, $CDCl_3$) δ 7.14-7.27 (m, 4H), 7.14 (m, 1H), 6.94-7.03 (m, 4H), 5.20 (3, 2H), 3.06 (t, 2H), 2.79 (t, 2H), 2.25 (s, 6H).

Scheme 6.4: Synthesis of 1-[4-(4-carboxy-1H-1,2,3-triazol-1-yl)butyl]-1H-1,2,3-triazole-4-carboxylic acid.

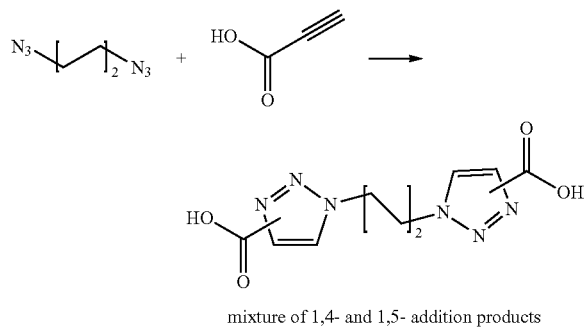

mixture of 1,4- and 1,5- addition products

Synthesis of 1-[4-(4-carboxy-1H-1,2,3-triazol-1-yl)butyl]-1H-1,2,3-triazole-4-carboxylic acid. Propionic acid (20.0 mg, 0.286 mmol) was dissolved in $CH_2Cl_2$ (5 mL) and placed in a round-bottom flask. Diazidobutane (10.1 mg, 0.143 mmol) and SOMS (100 mg) were added to the flask. The solvent was removed in vacuo. $CH_2Cl_2$ (1:1, v:v) was added until the SOMS was saturated, but not oversaturated. The round-bottom flask was equipped with a reflux condenser and heated at 60° C. for 23 hours. The SOMS were washed during filtration with $CH_2Cl_2$ (100 mL). The solvent was removed in vacuo to afford 1-[4-(4-carboxy-1H-1,2,3-triazol-1-yl)butyl]-1H-1,2,3-triazole-4-carboxylic acid as an off white solid (16.0 mg, 40%). $^1$H-NMR (400 MHz, $CDCl_3$) δ 7.85 (s, 2H), 4.22 (t, 4H), 1.95 (t, 4H).

Scheme 6.5: Synthesis of 1-[8-(4-carboxy-1H-1,2,3-triazol-1-yl)butyl]-1H-1,2,3-triazole-4-carboxylic acid.

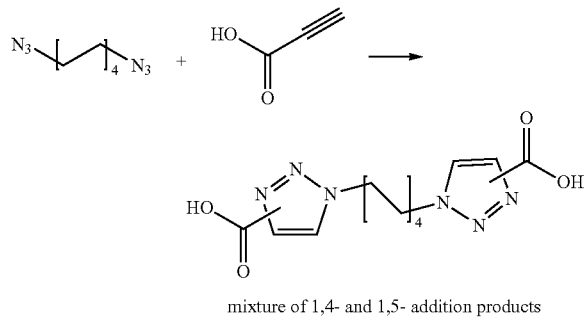

mixture of 1,4- and 1,5- addition products

Synthesis of 1-[8-(4-carboxy-1H-1,2,3-triazol-1-yl)butyl]-1H-1,2,3-triazole-4-carboxylic acid. Propionic acid (20.0 mg, 0.286 mmol) was dissolved in $CH_2Cl_2$ (5 mL) and placed in a round-bottom flask. Diazidobutane (28.1 mg, 0.143 mmol) and SOMS (100 mg) were added to the flask. The solvent was removed in vacuo. $CH_2Cl_2$ (1:1, v:v) was added until the SOMS was saturated, but not oversaturated. The round-bottom flask was equipped with a reflux condenser and heated at 60° C. for 23 hours. The SOMS were washed during filtration with $CH_2Cl_2$ (100 mL). The solvent was removed in vacuo to afford 1-[8-(4-carboxy-1H-1,2,3-triazol-1-yl)butyl]-1H-1,2,3-triazole-4-carboxylic acid as an off white solid (15.4 mg, 32%). $^1$H-NMR (400 MHz, $CDCl_3$) δ 7.85 (s, 2H), 4.22 (t, 4H), 1.87 (p, 4H), 1.33 (p, 4H), 1.24 (t, 4H).

Example 7: Use of SOMS as Nanoreactors to Facilitate Direct Amidation Reactions

Scheme 7.0: Generic nucleophilic direct amidation reaction wherein $R_1$ and $R_2$ are carbon bearing residues.

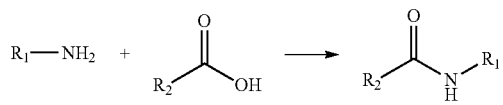

Direct amidation reactions are a sub-class of synthetic organic reactions, Scheme 7.0. These reactions feature the direct addition of an amine ($NH_2$) containing residue ($R_1$) to a carboxylic acid (COOH) containing residue ($R_2$) such that a new covalent bond between the amine and carboxylic acid is formed. There exist no literature reports of direct amidation reactions, under synthetically useful conditions.

Specific Examples

Scheme 7.1: Synthesis of N-benzoyl-N-methylbenzamide.

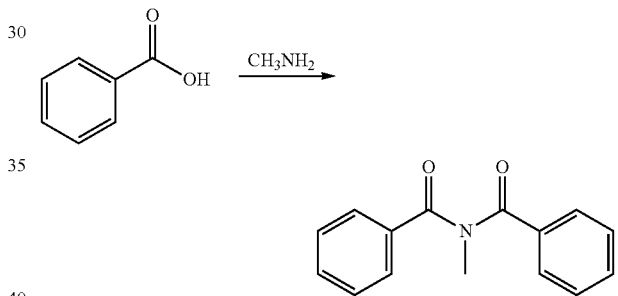

Synthesis of N-benzoyl-N-methylbenzamide. To a solution of benzoic acid (100.0 mg, 0.819 mmol) was dissolved in $CH_2Cl_2$ (10 mL) in a 100 mL round-bottom flask. Methylamine (80%, w:w, 5 mL) was added followed by SOMS (1.5 g). The solution was heated at 45° C. for 24 hrs. The SOMS were washed during filtration with $CH_2Cl_2$ (300 mL). The organic layer was dried with $Na_2SO_4$ and concentrated in vacuo to afford N-benzoyl-N-methylbenzamide as a clear solid (96.0 mg, 98%). $^1$H-NMR (400 MHz, $CDCl_3$) δ 7.75 (m, 2H), 7.64 (m, 1H), 7.47 (m, 2H), 2.63 (s, 3H).

Scheme 7.2: Synthesis of $N^1$, $N^2$-di(9H-fluorem-9-yl)adipamode (4C).

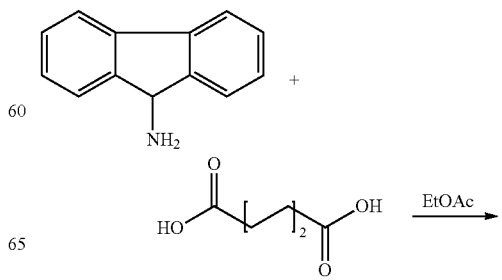

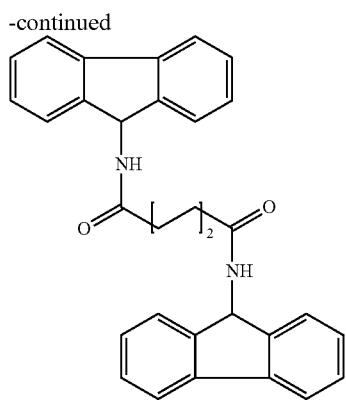

Synthesis of N¹,N²-di(9H-fluorem-9-yl)adipamode (4C). To an oven-dried 50 ml RBF was added 9-aminofluorene HCl (100 mg, 0.46 mmol) and a stir bar. While stirring, Ethyl-MgBr (3.0 M, 4.0 mL) in ether was added drop wise, and a color change from white to amber was observed, in addition to some effervescence. Once effervescence subsided, 500 mg of SOMS was added and ether was removed in vacuo. The resulting product, deprotonated 9-aminofluorene, was used as a reactant and the resulting MgCl and HBr salts were removed upon extraction of product from SOMS using a fritted glass funnel. The reaction vessel from the deprotonation of 9-aminofluorene HCl was suspended in a bath of ice. To the RBF was added adipic acid (33.54 mg, 0.92 mmol), EtOAc (10 mL), and SOMS (1.5 g). After 22 hours, the reaction mixture was extracted, washed, and concentrated to yield (4C) as a dark brown, viscous solid. ¹H-NMR (400 MHz, CDCl₃) δ 8.48 (d, 1H), 7.88 (d, 2H), 7.58 (d, 2H), 7.51 (t, 2H), 7.44 (t, 2H), 2.28 (t, 4H), 1.57 (t, 4H).

Scheme 7.3: Synthesis of N¹, N²-di(9H-fluorem-9-yl)adipamode (8C).

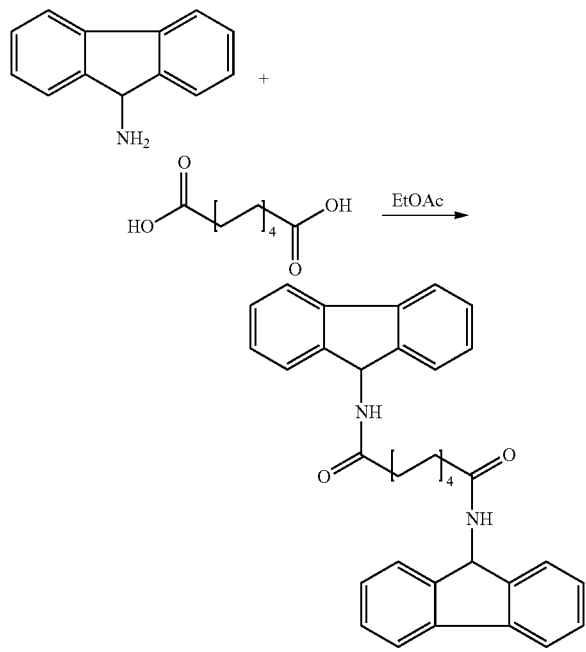

Synthesis of N¹,N²-di(9H-fluorem-9-yl)adipamode (8C). To an oven-dried 50 ml RBF was added 9-aminofluorene HCl (100 mg, 0.46 mmol) and a stir bar. While stirring, Ethyl-MgBr (3.0 M, 4.0 mL) in ether was added drop wise, and a color change from white to amber was observed, in addition to some effervescence. Once effervescence subsided, 500 mg of SOMS was added and ether was removed in vacuo. The resulting product, deprotonated 9-aminofluorene, was used as a reactant and the resulting MgCl and HBr salts were removed upon extraction of product from SOMS using a fritted glass funnel. The reaction vessel from the deprotonation of 9-aminofluorene HCl was suspended in a bath of ice water. To the RBF was added sebacic acid (46.5 mg, 0.92 mmol), EtOAc (10 mL), and SOMS (1.5 g). After 24 hours the reaction mixture was extracted, washed, and concentrated to yield (8C) as an amber/brown solid. ¹H-NMR (400 MHz, CDCl₃) δ 8.53 (d, 1H), 7.89 (d, 2H), 7.59 (d, 2H), 7.50 (t, 2H), 7.48 (t, 2H), 2.28 (t, 4H), 1.53 (p, 2H), 1.26 (m, 4H), Scheme 7.4: Synthesis of N¹, N²-di(9H-fluorem-9-yl)adipamode (10C).

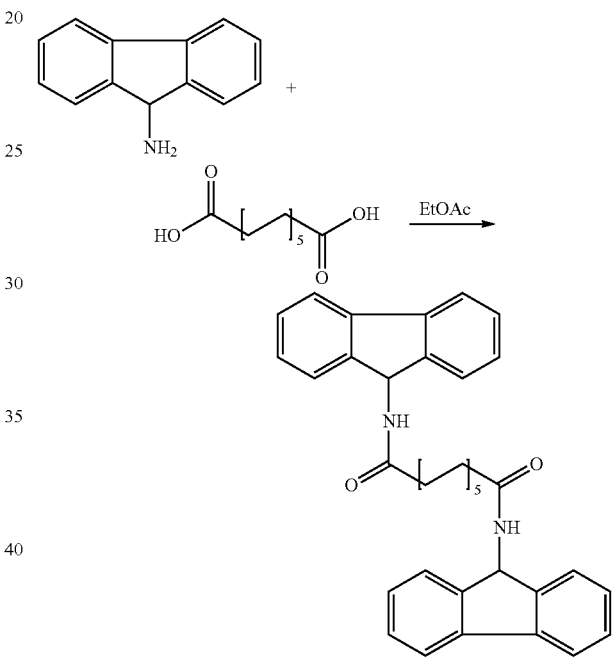

Synthesis of N¹,N²-di(9H-fluorem-9-yl)adipamode (10C). To an oven-dried 50 ml RBF was added 9-aminofluorene HCl (100 mg, 0.46 mmol) and a stir bar. While stirring, EthylMgBr (3.0 M, 4.0 mL) in ether was added drop wise, and a color change from white to amber was observed, in addition to some effervescence. Once effervescence subsided, 500 mg of SOMS was added and ether was removed in vacuo. The resulting product, deprotonated 9-aminofluorene, was used as a reactant and the resulting MgCl and HBr salts were removed upon extraction of product from SOMS using a fritted glass funnel. The reaction vessel from the deprotonation of 9-aminofluorene HCl was suspended in a bath of ice water. To the RBF was added thapsic acid (65.7 mg, 0.92 mmol), EtOAc (10 mL), and SOMS (1.5 g). After approximately 24 hours the reaction mixture was extracted, washed, and concentrated to yield (10C) as a dark brown solid. ¹H-NMR (400 MHz, CDCl₃) δ 8.52 (d, 1H), 7.90 (d, 2H), 7.57 (d, 2H), 7.51 (t, 2H), 7.43 (t, 2H), 2.28 (t, 4H), 1.53 (p, 2H), 1.24 (m, 6H), Scheme 7.5: General scheme for the synthesis of tri-peptides.

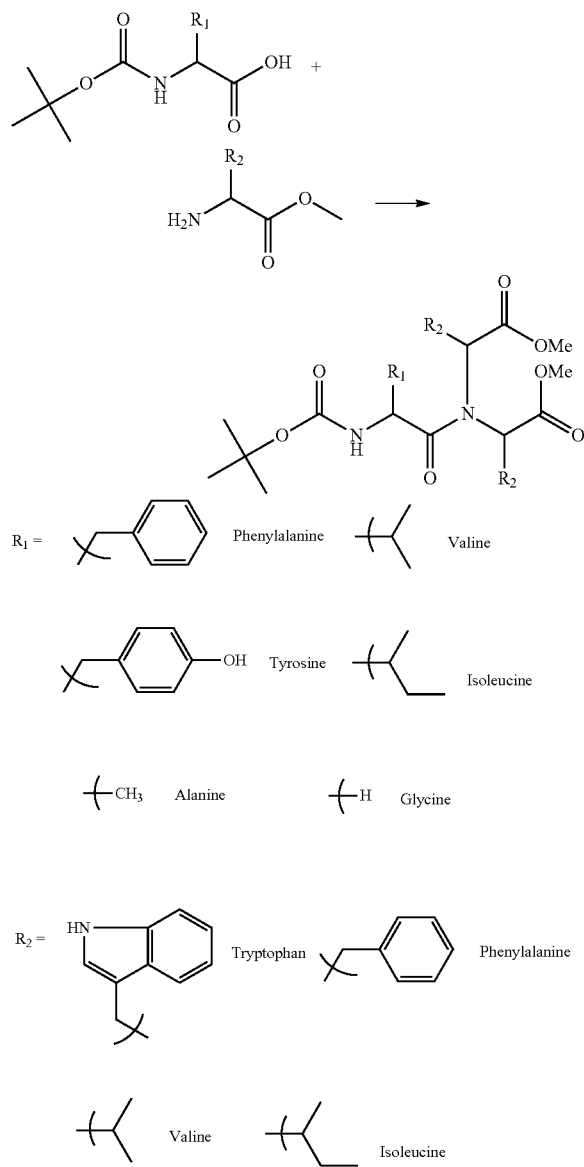

Synthesis of trip-peptides. The N-terminus protected amino acid (0.50 mmol) was dissolved in dichloromethane (CH$_2$Cl$_2$, 5 mL) in a 50 mL round-bottom flask. SOMS (500 mg) was added and the solvent was removed in vacuo. The C-terminus amino acid was added (1.0 mmol) to the round-bottom flask, followed by triethyl amine (1.0 mmol). The SOMS were saturated with CH$_2$Cl$_2$ such that the SOMS were not oversaturated. The round-bottom flask was equipped with a reflux condenser and heated at 40° C. for two hours. The SOMS were washed during extraction (MeOH, 100 mL) and the solvent was concentrated in vacuo to afford the tripeptide.

Conversely, The N-terminus protected amino acid (0.50 mmol) was dissolved in dichloromethane (CH$_2$Cl$_2$, 5 mL) in a 50 mL round-bottom flask. SOMS (500 mg) was added and the solvent was removed in vacuo. The C-terminus amino acid was added (1.0 mmol) to the round-bottom flask, followed by triethyl amine (1.0 mmmol). Solvent was removed on the rotary evaporator (719 mbar, 40° C.). CH$_2$Cl$_2$ (10 mL) was added to the round-bottom flask and removed on the rotary evaporator (719 mbar, 40° C.), this step was repeated an additional three times. The SOMS were washed during extraction (MeOH, 100 mL) and the solvent was concentrated in vacuo to afford the tripeptide.

Scheme 7.6: Synthesis of Boc-Phe-(Trp-OMe)$_2$.

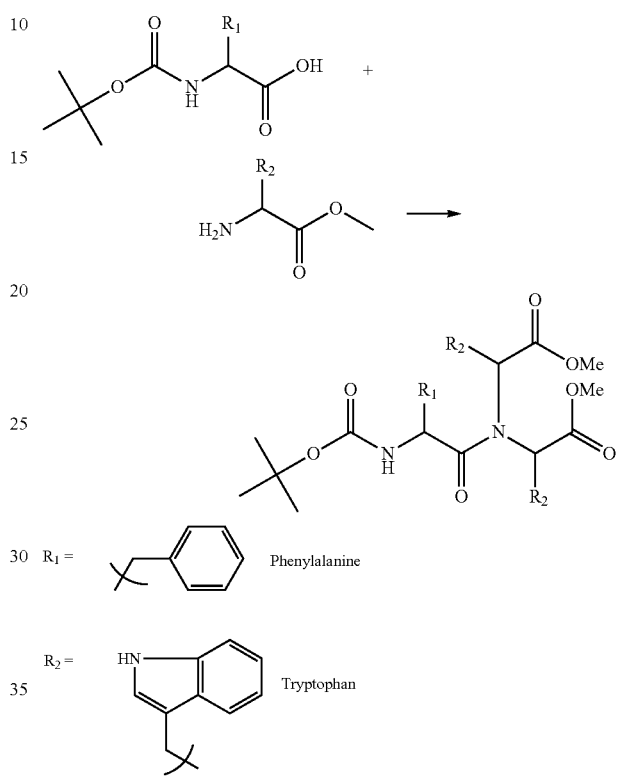

Synthesis of Boc-Phe-(Trp-OMe)$_2$. Boc-Phe-(Trp-OMe)$_2$ was afforded as an off white solid (100%). $^1$H-NMR (400 MHz, CDCl$_3$) δ 8.94 (br, 1H), 7.02-7.49 (m, 15H), 5.27 (br, 2H), 4.27 (m, 2H), 3.68 (s, 3H), 3.58 (m, 6H), 1.18 (s, 9H).

Scheme 7.7: Synthesis of Boc-Phe-(Phe-OMe)$_2$.

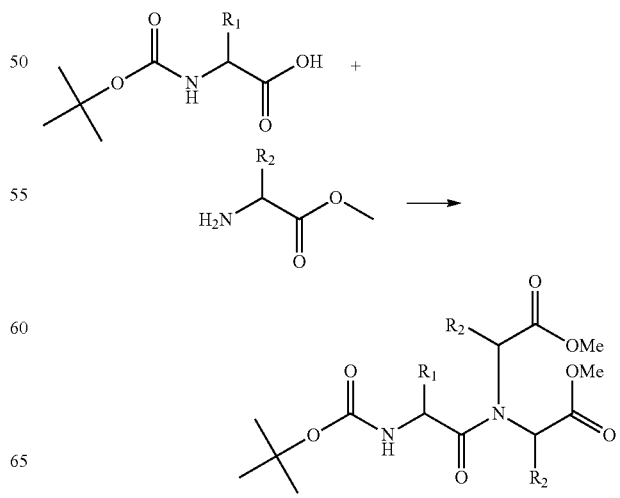

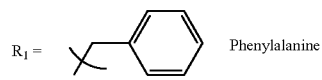 R₁ = Phenylalanine

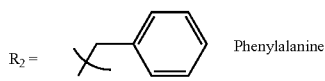 R₂ = Phenylalanine

Synthesis of Boc-Phe-(Phe-OMe)₂. Boc-Phe-(Phe-OMe)₂ was afforded as an off white solid (100%). ¹H-NMR (400 MHz, CDCl₃) δ 7.15-7.32 (m, 10H), 5.09 (d, 1H), 4.48 (d, 1H), 3.92 (m, 1H), 3.71 (s, 6H), 3.01-3.22 (m, 6H), 1.12 (s, 9H).

Scheme 7.8: Synthesis of Boc-Val-(Val-OMe)₂.

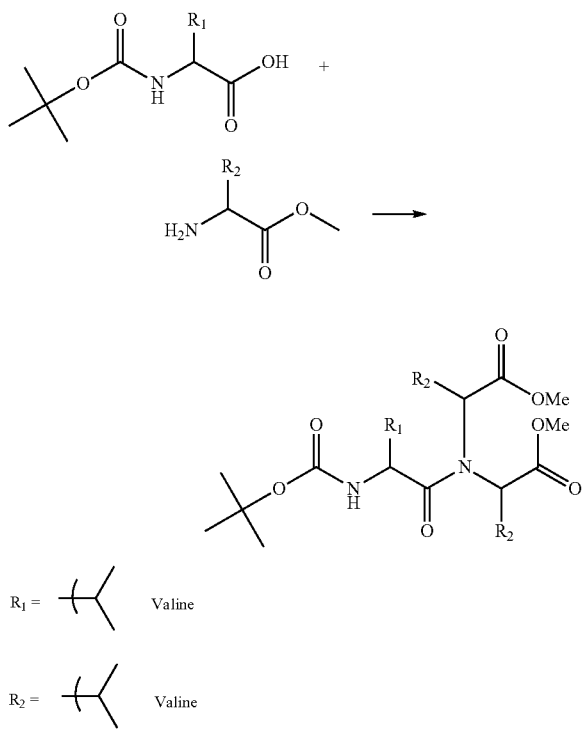

R₁ = Valine

R₂ = Valine

Synthesis of Boc-Val-(Val-OMe)₂. Boc-Val-(Val-OMe)₂ was afforded as an off white solid (100%). ¹H-NMR (400 MHz, CDCl₃) δ 5.12 (m, 1H), 4.04 (m, 1H), 3.72 (s, 6H), 3.03 (m, 3H), 1.21 (s, 9H), 0.84-0.91 (m, 12H).

Scheme 7.9: Synthesis of Boc-Phe-(Val-OMe)₂.

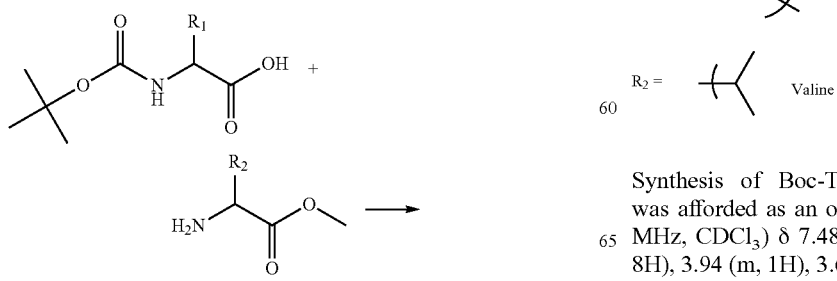

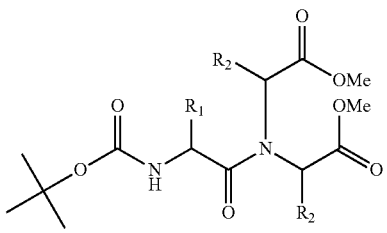

R₁ = Phenylalanine

R₂ = Valine

Synthesis of Boc-Phe-(Val-OMe)₂. Boc-Phe-(Val-OMe)₂ was afforded as an off white solid (100%). ¹H-NMR (400 MHz, CDCl₃) δ 7.08-7.18 (m, 5H), 6.31 (br, 3H), 5.08 (m, 1H), 4.27 (m, 1H), 3.48 (s, 6H), 2.78-2.91 (m, 3H), 1.18 (s, 9H), 0.91 (m, 6H).

Scheme 7.10 Synthesis of Boc-Trp-(Val-OMe)2.

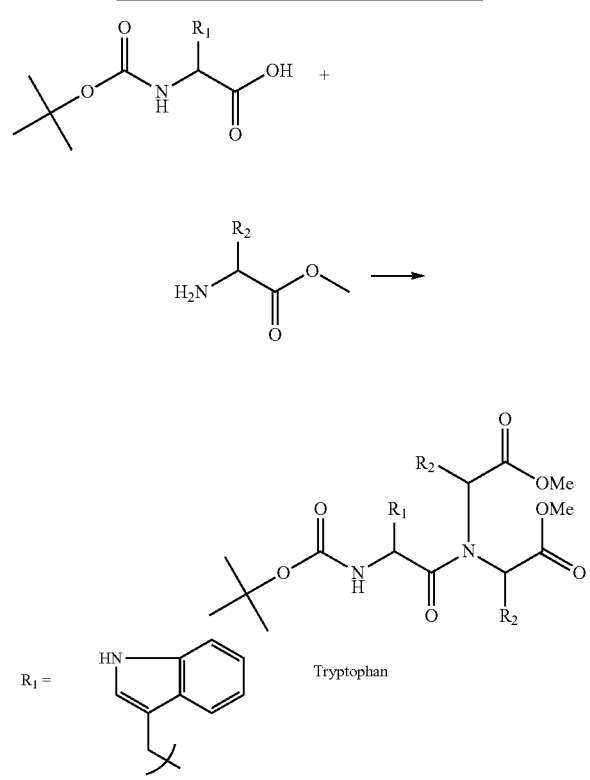

R₁ = Tryptophan

R₂ = Valine

Synthesis of Boc-Trp-(Val-OMe)₂. Boc-Trp-(Val-OMe)₂ was afforded as an off white solid (100%). ¹H-NMR (400 MHz, CDCl₃) δ 7.48 (d, 2H), 7.31 (d, 2H), 7.02-2.09 (m, 8H), 3.94 (m, 1H), 3.68 (m, 1H), 3.61 (m, 1H), 3.59 (s, 6H), 3.14-3.28 (m, 4H), 1.18 (s, 9H), 0.81 (m, 6H).

Scheme 7.11: Synthesis of Boc-Tyr-(Trp-OMe)₂.

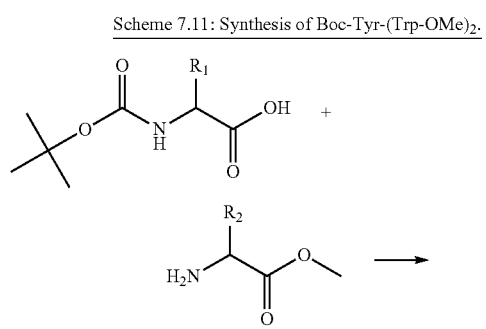

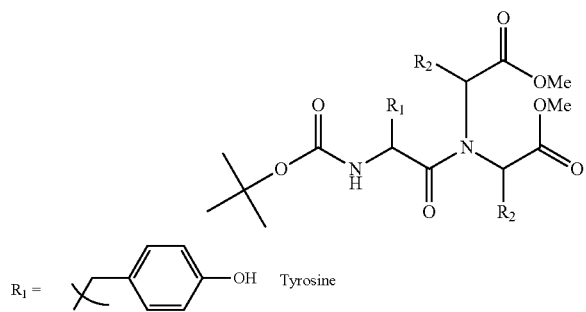

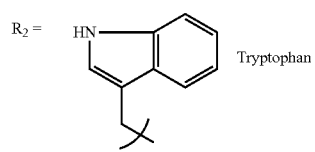

Synthesis of Boc-Tyr-(Trp-OMe)₂. Boc-Tyr-(Trp-OMe)₂ was afforded as an off white solid (100%). ¹H-NMR (400 MHz, CDCl₃) δ 8.25 (br, 1H), 7.02-7.49 (m, 14H), 4.99 (br, 2H), 4.34 (m, 2H), 3.97 (m, 1H), 3.68 (s, 3H), 3.58 (m, 6H), 1.18 (s, 9H).

Scheme 7.12: Synthesis of Boc-Phe-(Ile-OMe)₂.

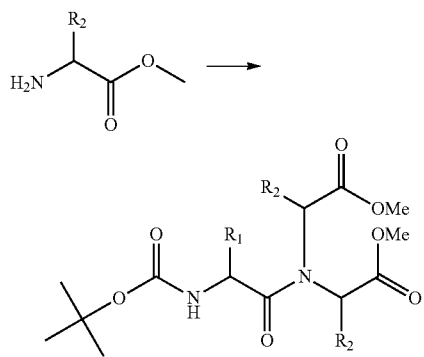

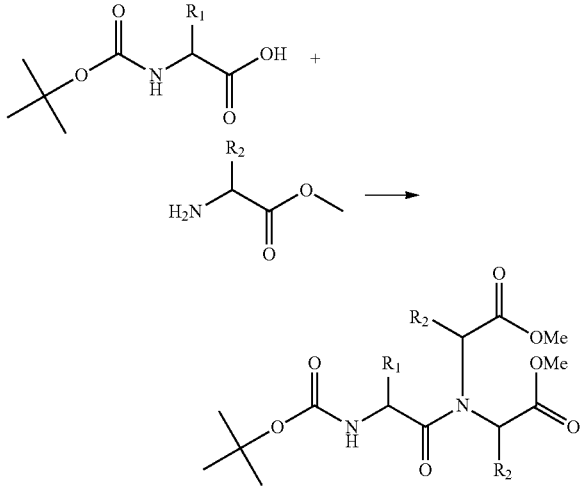

Synthesis of Boc-Phe-(Ile-OMe)₂. Boc-Phe-(Ile-OMe)₂ was afforded as an off white solid (100%). ¹H-NMR (400 MHz, CDCl₃) δ 7.19-7.30 (m, 5H), 5.08 (m, 1H), 4.51 (m, 1H), 3.49 (s, 6H), 3.10-3.22 (m, 4H), 1.89 (m, 2H), 1.28 (s, 9H), 0.91-1.27 (m, 12H).

Scheme 7.13: Synthesis of Boc-Val-(Trp-OMe)₂.

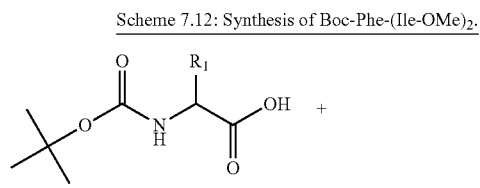

Synthesis of Boc-Val-(Trp-OMe)₂. Boc-Val-(Trp-OMe)₂ was afforded as an off white solid (100%). ¹H-NMR (400 MHz, CDCl₃) δ 8.25 (br, 1H), 8.18 (br, s), 7.02-7.49 (m, 10H), 6.29 (m, 1H), 5.18 (m, 2H), 4.31 (m, 2H), 3.97 (m, 1H), 3.71 (s, 3H), 3.59 (m, 3H), 1.18 (s, 9H).

Scheme 7.14 Synthesis of Boc-Ile-(Trp-OMe)₂.

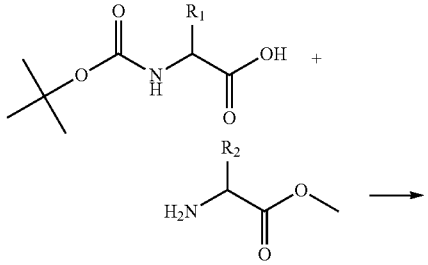

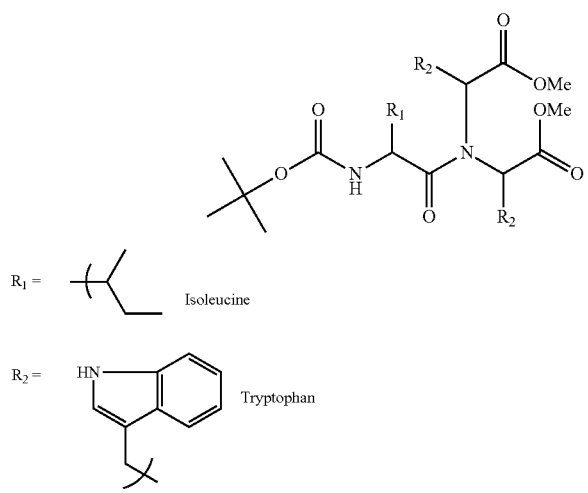

R₁ = Isoleucine

R₂ = Tryptophan

Synthesis of Boc-Ile-(Trp-OMe)₂. Boc-Ile-(Trp-OMe)₂ was afforded as an off white solid (100%). ¹H-NMR (400 MHz, CDCl₃) δ 7.06-7.46 (m, 10H), 5.21 (m, 1H), 4.07 (m, 2H), 3.65 (s, 6H), 3.22-3.44 (m, 4H), 1.78 (br, 1H), 1.41 (s, 9H), 0.80-0.90 (m, 6H).

Scheme 7.15: Synthesis of Boc-Ala-(Trp-OMe)₂.

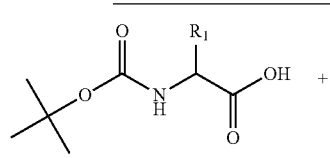

R₁ = —CH₃  Alanine

R₂ = Tryptophan

Synthesis of Boc-Ala-(Trp-OMe)₂. Boc-Ala-(Trp-OMe)₂ was afforded as an off white solid (100%). ¹H-NMR (400 MHz, CDCl₃) δ 7.12-7.53 (m, 10H), 5.21 (m, 1H), 4.13 (m, 2H), 3.96 (m, 1H), 3.65 (s, 6H), 3.17-3.39 (m, 4H), 1.78 (br, 1H), 1.49 (s, 9H), 0.90 (s, 3H).

Scheme 7.16: Synthesis of Boc-Val-(Trp-OMe)₂.

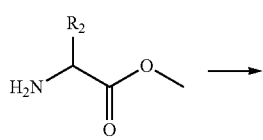

R₁ = Valine

R₂ = Tryptophan

Synthesis of Boc-Val-(Trp-OMe)₂. Boc-Val-(Trp-OMe)₂ was afforded as an off white solid (100%). ¹H-NMR (400 MHz, CDCl₃) δ 7.00-7.37 (m, 10H), 5.45 (m, 1H), 5.03 (m, 4H), 4.06 (m, 1H), 3.65 (s, 6H), 3.17-3.37 (m, 4H), 2.01 (br, 1H), 1.38 (s, 9H), 0.87 (s, 3H).

Scheme 7.17: Synthesis of Boc-Gly-(Trp-OMe)₂.

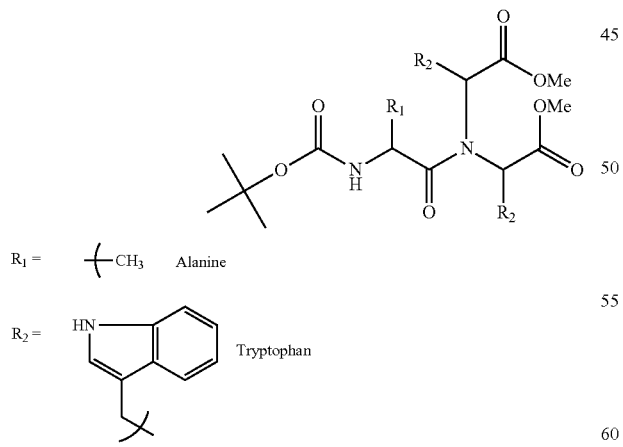

-continued

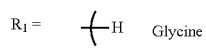

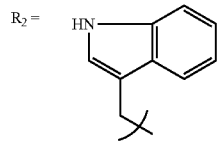

Synthesis of Boc-Gly-(Trp-OMe)$_2$. Boc-Gly-(Trp-OMe)$_2$ was afforded as an off white solid (100%). $^1$H-NMR (400 MHz, CDCl$_3$) δ 9.06 (s, 1H), 7.04-6.92 (m, 10H), 4.04 (s, 1H), 3.65 (s, 6H), 3.59-3.05 (m, 5H), 1.44 (s, 9H).

Example 8: Use of SOMS as Nanoreactors to Facilitate Elimination Reactions

Scheme 8.0: Generic elimination reaction wherein R$_1$ is a carbon bearing residue.

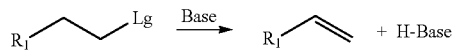

Elimination reactions are a sub-class of synthetic organic reactions, Scheme 8.0. These reactions feature the loss of a hydrogen from a carbon bearing residue (R$_1$). A new carbon-carbon bond is formed following loss of the leaving group.

Specific Examples

Scheme 8.1: Synthesis of cyclohexene.

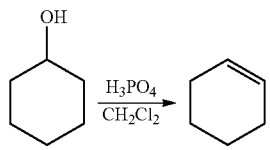

Synthesis of cyclohexene. Cyclohexanol (100 mg, 0.998 mmol) was dissolved in CH$_2$Cl$_2$ (5 mL) in a 100 mL round-bottom flask. Phosphoric acid (0.5 mL) was added followed by SOMS (1.0 g). The reaction was heated at 60° C. for 24 hours. The SOMS were washed during filtration with CH$_2$Cl$_2$ (300 mL) and the solvent was concentrated in vacuo to afford cyclohexene as a clear liquid (75.6 mg, 97%). $^1$H-NMR (400 MHz, CDCl$_3$) δ 5.17 (m, 2H), 2.05 (m, 4H), 1.40 (m, 4H).

Example 9: Use of SOMS as Nanoreactors to Facilitate Electrophilic Alkene and Alkyne Addition Reactions Scheme 9.0: Generic electrophilic alkene and alkyne addition reactions wherein R$_1$ is a carbon bearing residue.

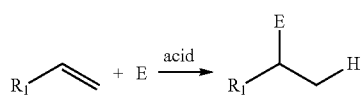

Electrophilic alkene and alkyne addition reactions are a sub-class of synthetic organic reactions, Scheme 9.0. These reactions feature the addition of an electrophile and hydrogen atom to an alkene bearing a carbon residue (R$_1$).

Specific Examples

Scheme 9.1: Synthesis of cyclohexylether.

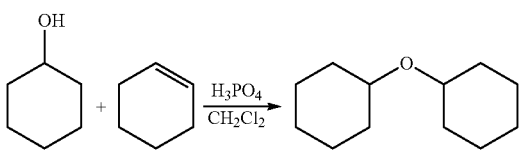

Synthesis of cyclohexylether. Cyclohexanol (100 mg, 0.998 mmol) was dissolved in CH$_2$Cl$_2$ (5 mL) in a 100 mL round-bottom flask. Cyclohexene (81.9 mg, 0.998 mmol) and phosphoric acid (100 μL) was added followed by SOMS (1.0 g). The reaction was heated at 60° C. for 24 hours. The SOMS were washed during filtration with CH$_2$Cl$_2$ (300 mL) and the solvent was concentrated in vacuo to afford cyclohexylether as a clear liquid (75.6 mg, 97%). $^1$H-NMR (400 MHz, CDCl$_3$) δ 3.46 (m, 2H), 1.36-1.75 (m, 18H) 1.41 (m, 2H).

Example 10: Use of SOMS as Nanoreactors to Facilitate Nucleophilic Alkene and Alkyne Addition Reactions Scheme 10.0: Generic nucleophilic alkene and alkyne addition reactions wherein R is a carbon bearing residue.

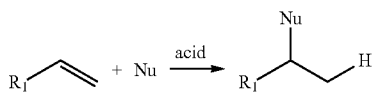

Nucleophilic alkene and alkyne addition reactions are a sub-class of synthetic organic reactions, Scheme 10.0. These reactions feature the addition of a nucleophile and hydrogen atom to an alkene bearing a carbon residue (R$_1$).

Example 11: Use of SOMS as Nanoreactors to Facilitate Multi Component Reactions Scheme 11.0: Generic Ugi reaction (a), Biginelli reaction (b), Passarini reaction (c), and Mannich reaction (d), examples of multi component reactions.

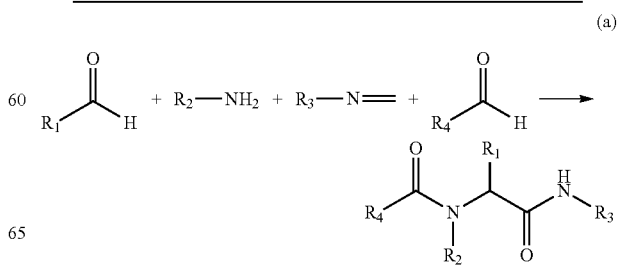

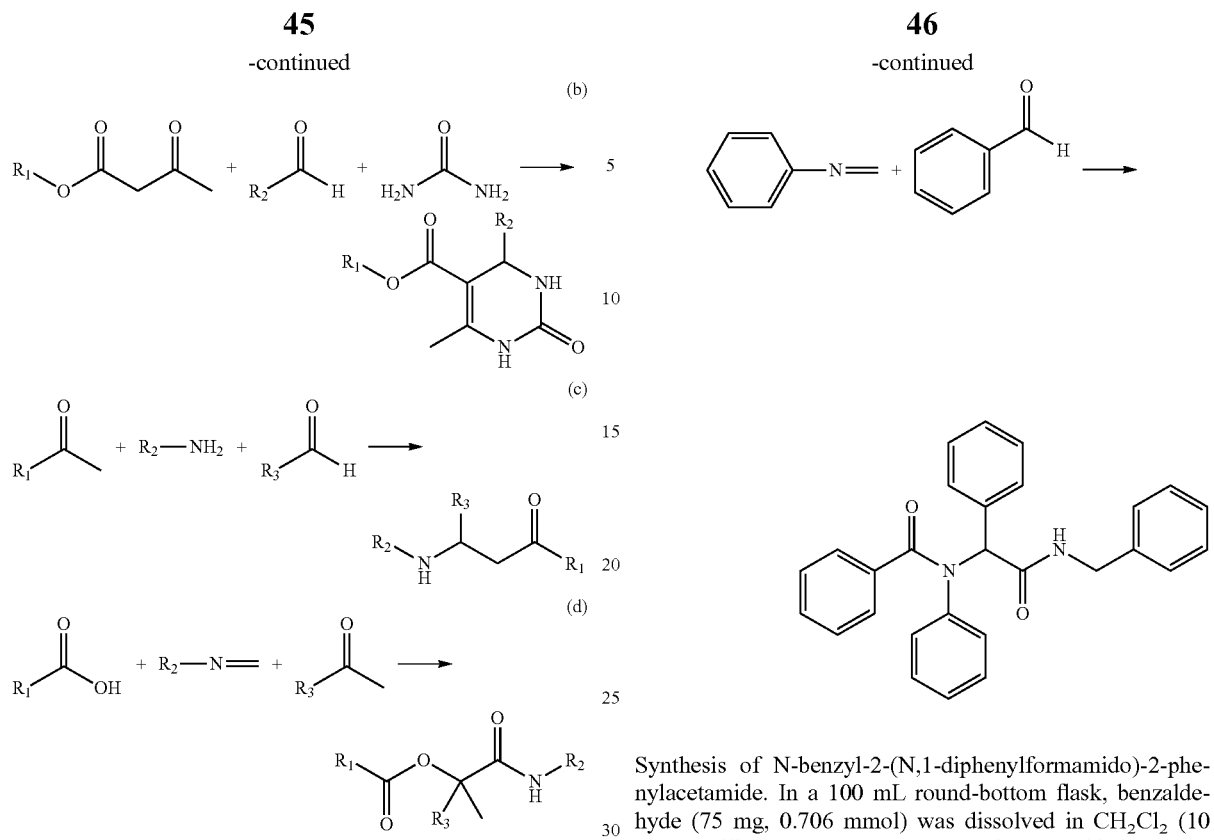

The Ugi reaction (Scheme 11.0(a)) is four-component reaction between an aldehyde bearing carbon residue ($R_1$), an amine bearing carbon residue ($R_2$), an isocyanide bearing carbon residue ($R_3$), and a carboxylic acid bearing residue ($R_4$) to produce a bis-amide.

The Biginelli reaction (Scheme 11.0(b)) is a three-component reaction between a ß-ketoester bearing residue ($R_1$), an aldehyde bearing carbon residue ($R_2$), and urea to produce a dihydropyrimidones.

The Passarini reaction (Scheme 11.0(c)) is a three-component reaction between a carboxylic acid bearing carbon residue ($R_1$), a ketone bearing molecule ($R_2$), and an isocyanide bearing carbon residue ($R_3$) to produce an α-acyloxy amide.

The Mannich reaction (Scheme 11.0(d)) is a three-component reaction between a ketone bearing carbon residue ($R_1$), an aldehyde bearing carbon residue ($R_2$) and an amine bearing compound ($R_3$) to produce a β-amino-carbonyl compound, the Mannich base.

Specific Examples

Scheme 11.1: Synthesis of N-benzyl-2-(N,1-diphenylformamido)-2-phenylacetamide.

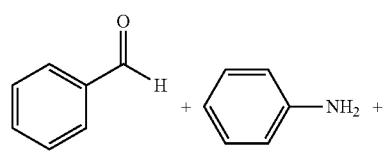

Synthesis of N-benzyl-2-(N,1-diphenylformamido)-2-phenylacetamide. In a 100 mL round-bottom flask, benzaldehyde (75 mg, 0.706 mmol) was dissolved in $CH_2Cl_2$ (10 mL). Aniline (65.8 mg, 0.706 mmol) was added and the solvent was removed at 40° C. and 719 mbar. $CH_2Cl_2$ (10 mL was added) and the solvent was removed at 40° C. and 719 mbar. This process was repeated eight more times, for a total of ten times. Benzoic acid (86.2 mg, 0.706 mmol) and benzyklcyanide (82.7 mg, 0.706 mmol) were dissolved in $CH_2Cl_2$ (10 mL) and added to the round-bottom flask. The solvent was removed at 40° C. and 719 mbar. The SOMS were saturated with $CH_2Cl_2$ and the round-bottom flask was heated at 45° C. for 24 hrs. The SOMS were washed during filtration with $CH_2Cl_2$ (300 mL) and the solvent was concentrated in vacuo to afford N-benzyl-2-(N,1-diphenylformamido)-2-phenylacetamide as an off-white solid (285.0 mg, 96%). $^1$H-NMR (400 MHz, CDCl$_3$) δ 7.54-7.62 (m, 6H), 7.27-7.52 (m, 14H), 7.16-7.26 (m, 3H), 6.5 (br, 1H), 6.21 (s, 1H), 4.50 (s, 2H), 4.31 (br, 1H).

Scheme 11.2: Synthesis of N-benzyl-2-[N-(4-methoxyphenyl)-1-phenylformamido]-2-(3-nitrophenyl)acetamide.

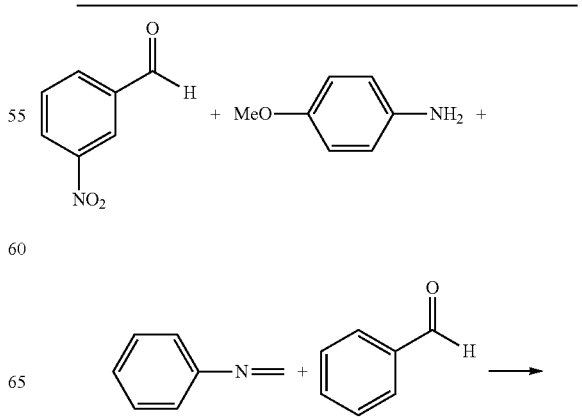

-continued

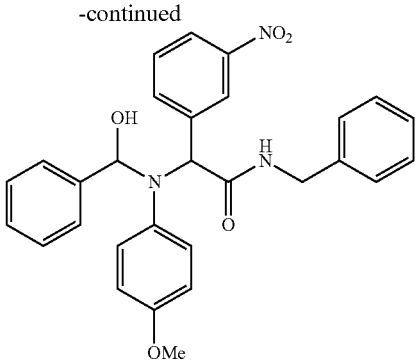

Synthesis of N-benzyl-2-[N-(4-methoxyphenyl)-1-phenyl-formamido]-2-(3-nitrophenyl)acetamide 3-Nitrobenzaldehyde (1.290 g, 8.53 mmol), p-anisidine (1.051 g, 8.53 mmol), and dichloromethane (CH$_2$Cl$_2$, 10 mL) were combined in a 100 mL round-bottom flask. SOMS (1.0 g) was added to the flask followed by CH$_2$Cl$_2$ (5.0 mL). Solvent was removed using the rotary evaporator (488 mbar, 40° C.). CH$_2$Cl$_2$ (3.5 mL) was added and evaporated using the rotary evaporator (488 mbar, 40° C.). This step was repeated an additional three times. Benzoic acid (1.042 g, 8.53 mmol) and benzyl isocyanide (1.051 g, 8.53 mmol) were added to the round-bottom flask followed by CH$_2$Cl$_2$ (10 mL). Solvent was removed using the rotary evaporator (488 mbar, 40° C.). CH$_2$Cl$_2$ (3.5 mL) was added and evaporated using the rotary evaporator (488 mbar, 40° C.). This step was repeated an additional 13 times. The SOMS were washed during filtration and the solution was concentrated in vacuo to afford enantiomers of N-benzyl-2-[N-(4-methoxyphenyl)-1-phenylformamido]-2-(3-nitrophenyl)acetamide as an off white solid (4.227 g, 100%). $^1$H-NMR (400 MHz, CDCl$_3$) δ 6.48-8.52 (m, 18H), 4.62 (s, 1H), 4.62 (s, 2H), 4.53 (s, 1H), 3.81 (s, 3H), 3.71 (s, 2H), 3.62 (s, 3H).

Scheme 11.3: Synthesis of ethyl 6-methyl-2-oxo-4-phenyl-1,2,3,4-tetrahydropyrimidine-5-carboxylate.

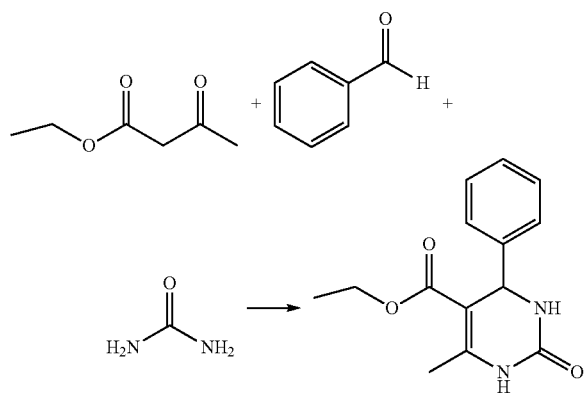

Synthesis of Ethyl 6-methyl-2-oxo-4-phenyl-1,2,3,4-tetrahydropyrimidine-5-carboxylate Benzaldehyde (100 mg, 1.023 mmol) was added to a 100 mL round-bottom flask followed by CH$_2$Cl$_2$ (5 mL), ethyl acetoacetate (129.7 mg, 0.998 mmol), and urea (59.9 mg, 0.998 mmol). SOMS (2.0 g) were added and CH$_2$Cl$_2$ was added until the SOMS were saturated. The solution was heated at 50° C. for 24 hrs. The SOMS were washed during filtration with CH$_2$Cl$_2$ (300 mL) and the solvent was concentrated in vacuo to afford the ethyl 6-methyl-2-oxo-4-phenyl-1,2,3,4-tetrahydropyrimidine-5-carboxylate as an off-white solid (246.8 mg, 95%). $^1$H-NMR (400 MHz, CDCl$_3$) δ 7.30 (m, 2H), 7.21 (m, 1H), 6.87 (m, 2H), 5.29 (s, 1H), 4.14 (q, 2H), 2.46 (s, 3H), 1.21 (t, 3H).

Scheme 11.4: Synthesis of 1-(benzylamino)-1-(3-nitrophenyl)pentan-2-one.

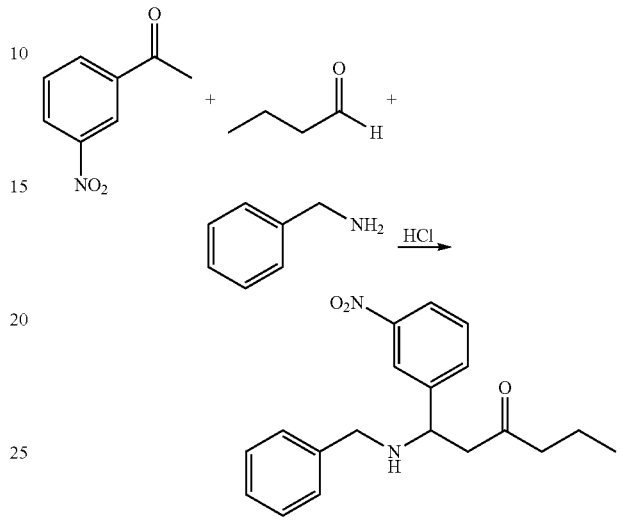

Synthesis of 1-(benzylamino)-1-(3-nitrophenyl)pentan-2-one. 3-Nitrobenzaldehyde (500 mg, 3.30 mmol), butyraldehyde (240 mg, 0.330 mmol), benzylamine (35.3 mg, 0.330 mmol), and solvent (H$_2$O:MeOH; 1:100; v:v, 5 mL) were combined in a 100 mL round-bottom flask. K$_2$CO$_3$ (503.3 mg) was added to the flask followed by acetone washed SOMS (1.0 g). The round-bottom flask was equipped with a reflux condenser and heat at 60° C. for 1.5 hrs. The SOMS were washed during filtration with MeOH (100 mL). Solvent was removed in vacuo to afford 1-(benzylamino)-1-(3-nitrophenyl)pentan-2-one as a 3:2 ratio of enantiomers (75%).

Conversely, 3-nitrobenzaldehyde (500 mg, 3.30 mmol), butyraldehyde (240 mg, 0.330 mmol), benzylamine (35.3 mg, 0.330 mmol), and solvent (H$_2$O:MeOH; 1:100; v:v, 5 mL) were combined in a 100 mL round-bottom flask. SOMS (1.0 g) was added to the flask. The round-bottom flask was equipped with a reflux condenser and heat at 60° C. for 1.5 hrs. The SOMS were washed during filtration with MeOH (100 mL). Solvent was removed in vacuo to afford 1-(benzylamino)-1-(3-nitrophenyl)pentan-2-one as a 3:1 ratio of enantiomers (55%).

Conversely, 3-Nitrobenzaldehyde (500 mg, 3.30 mmol), butyraldehyde (240 mg, 0.330 mmol), benzylamine (35.3 mg, 0.330 mmol), and solvent (H$_2$O:MeOH; 1:100; v:v, 5 mL) were combined in a 100 mL round-bottom flask. K$_2$CO$_3$ (503.3 mg) was added to the flask followed by acetone washed SOMS (1.0 g). Solvent was removed using the rotary evaporator (488 mbar, 40° C.). Solvent (H$_2$O: MeOH; 1:100; v:v, 5 mL) was added and evaporated using the rotary evaporator (488 mbar, 40° C.). This step was repeated an additional 13 times. The SOMS were washed during filtration and the solution was concentrated in vacuo to afford 1-(benzylamino)-1-(3-nitrophenyl)pentan-2-one as a 2:1 ratio of enantiomers (85%).

$^1$H-NMR (400 MHz, CDCl$_3$) δ 7.51-8.67 (m, 9H), 4.89 (s, 1H), 4.51 (s, 2H), 2.61 (t, 2H), 1.61 (p, 2H), 1.28 (t, 3H).

Scheme 11.5: Synthesis of diphenyl(phenylcarbamoyl)methyl benzoate.

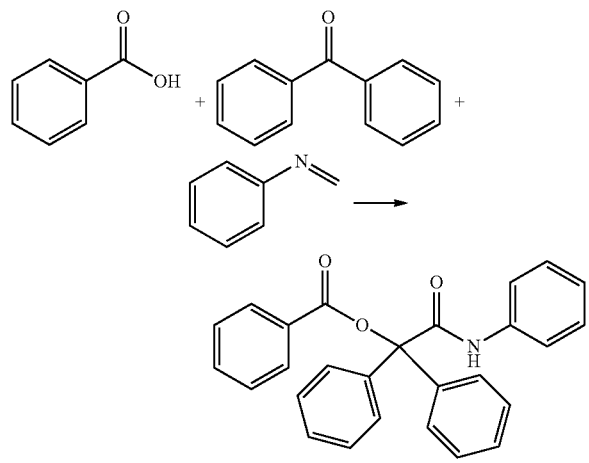

Synthesis of diphenyl(phenylcarbamoyl)methyl benzoate. Benzoic acid (335 mg, 2.74 mmol), benzophenone (500 mg, 2.74 mmol), benzyl isocyanide (321 mg, 2.74 mmol), and dichloromethane ($CH_2Cl_2$, 3 mL) were combined in a 100 mL round-bottom flask followed by acetone washed SOMS (1.0 g). The round-bottom flask was equipped with a reflux condenser and heat at 50° C. for 1.5 hrs. The SOMS were washed during filtration with $CH_2Cl_2$ (100 mL). Solvent was removed in vacuo to afford diphenyl(phenylcarbamoyl)methyl benzoate as an off white solid (1.004 g, 90%). $^1$H-NMR (400 MHz, $CDCl_3$) δ 8.27 (d, 1H), 8.11 (d, 1H), 7.80-7.25 (m, 18H).

Example 12: Use of SOMS as Nanoreactors to Facilitate Wittig Reactions

Scheme 12.0: Generic Wittig reaction wherein $R_1$ and $R_2$ are carbon bearing residues.

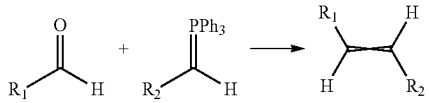

The Wittig reaction is a carbon bond forming reaction (Scheme 12.0). These reactions feature the addition of an aldehyde or ketone bearing carbon residue ($R_1$) to a triphenylphosphide ylide bearing carbon residue ($R_2$) to for a new carbon-carbon double bond.

Specific Examples

Scheme 12.1: Synthesis of ethyl (2E)-3-phenylprop-2-enoate and ethyl (2Z)-3-phenylprop-2-enoate.

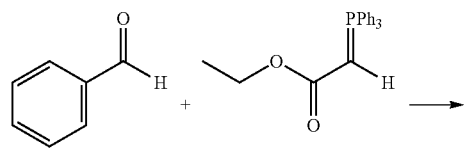

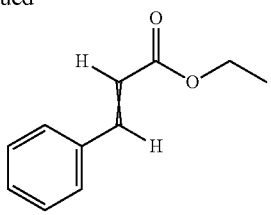

Synthesis of Ethyl (2E)-3-phenylprop-2-enoate and Ethyl (2Z)-3-phenylprop-2-enoate. To a solution of ethyl(triphenylphosphoranylidene)acetate (75 mg, 0.215 mmol) in ethanol (15 mL) in a 100 mL round-bottom flask. Benzaldehyde (22.8 mg, 0.215 mmol) was added followed by SOMS (1.0 g). The solvent was removed at 40° C. and 119 mbar. MeOH (50 mL) was added to the round-bottom flask followed by solvent removal at 40° C. and 119 mbar. This cycle was repeated four more times for a total of six times. The SOMS were washed during filtration with EtOH (300 mL) and the solvent was concentrated in vacuo to afford ethyl (2E)-3-phenylprop-2-enoate and ethyl (2Z)-3-phenylprop-2-enoate, a mixture of E and Z isomers, as an off-white solid 37.0 mg, 99%. $^1$H-NMR (400 MHz, $CDCl_3$) δ (E isomer) 7.73 (d, 1H), 7.54 (m, 2H), 7.38-7.48 (m, 3H), 6.65 (d, 1H), 4.12 (q, 2H), 1.22 (t, 3H). $^1$H-NMR (400 MHz, $CDCl_3$) δ (Z isomer) 7.54 (m, 2H), 7.39 (d, 1H), 7.37-7.48 (m, 4H), 5.76 (d, 1H), 4.12 (q, 2H), 1.22 (t, 3H).

Example 13: Use of SOMS as Nanoreactors to Facilitate the Synthesis of Acetylsalicylic Acid (Aspirin)

Scheme 13.0: Synthesis of acetylsalicylic acid (aspirin).

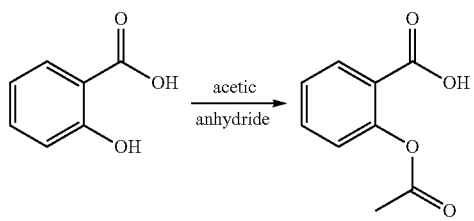

Acetylsalicylic acid, also known as aspirin, is an over-the-counter medication commonly used to treat pain, fever, and inflammation and can be prepared as shown in Scheme 13.0.

Specific Examples

Synthesis of Acetylsalicylic Acid. Salicylic acid (100 mg, 0.724 mmol) was dissolved in 10 mL of $CH_2Cl_2$ in a 100 mL round-bottom flask. Acetic anhydride (147.8 mg, 1.448 mmol) was added followed by SOMS (1 g). The solvent was removed at 40° C. and 719 mbar. Solvent was removed at 40° C. and 719 mbar. $CH_2Cl_2$ (10 mL) was added and the solvent removed at 40° C. and 719 mbar. This was repeated three more times, for a total of five times. The SOMS were washed during filtration with $CH_2Cl_2$ (150 mL). The solution was washed with a saturated $NaHCO_3$ solution (250 mL, 3×). The organic layer was collected and the solvent was removed in vacuo to afford acetylsalicylic acid as a white solid (127.8 mg, 97%). ¹H-NMR (400 MHz, CDCl₃) δ 8.10 (m, 1H), 7.71 (m, 1H), 7.53 (m, 1H), 7.43 (m, 1H), 2.11 (s, 3H).

Example 14: Use of SOMS as Nanoreactors to Facilitate the Synthesis of Acetaminophen (Tylenol®)

Scheme 14.0: Synthesis of acetaminophen (Tylenol®).

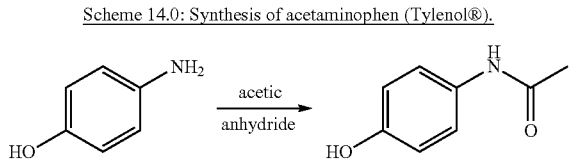

Acetaminophen, also known as Tylenol®, is an over-the-counter medication commonly used to treat pain and fever and can be prepared as shown in Scheme 14.0.

Specific Examples

Synthesis of Acetaminophen. 4-Aminophenol (100 mg, 0.916 mmol) was dissolved in 10 mL of CH₂Cl₂ in a 100 mL round-bottom flask. Acetic anhydride (187.1 mg, 1.832 mmol) was added followed by SOMS (1 g). The solvent was removed at 40° C. and 719 mbar. Solvent was removed at 40° C. and 719 mbar. CH₂Cl₂ (10 mL) was added and the solvent removed at 40° C. and 719 mbar. This was repeated three more times, for a total of five times. The SOMS were washed during filtration with CH₂Cl₂ (150 mL). The solution was washed with a saturated NaHCO₃ solution (250 mL, 3×). The organic layer was collected and the solvent was removed in vacuo to afford acetaminophen acid as a white solid (137.1 mg, 99%). ¹H-NMR (400 MHz, CDCl₃) δ 7.26 (m, 2H), 6.67 (m, 2H), 6.08 (br, 1H), 4.81 (br, 1H) 2.02 (s, 3H).

Example 15: Use of SOMS as Nanoreactors to Facilitate the Synthesis of Resveratrol Scheme 15.0: Synthesis of resveratrol.

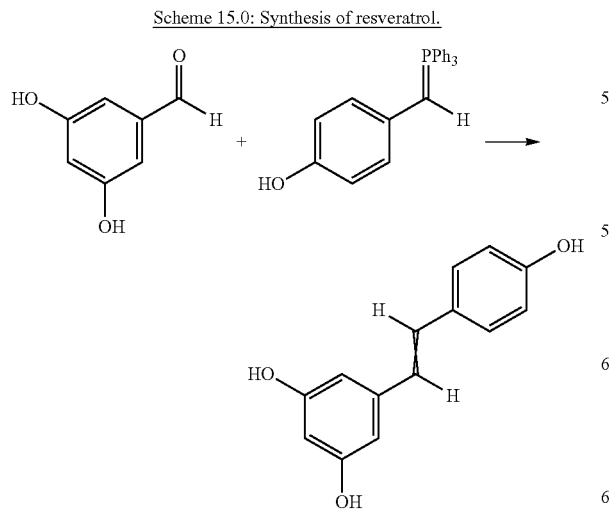

Resveratrol is a naturally occurring phenol commonly found in grapes, blueberries, and raspberries, and can be prepared as shown in Scheme 15.0.

Specific Examples

Synthesis of Resveratrol. To a solution of [(3,5-dihydroxyphenyl)methyl]triphenylphosphonium bromide (75 mg, 0.130 mmol) in ethanol (15 mL) in a 100 mL round-bottom flask. P-tolualdehyde (15.83 mg, 0.130 mmol) was added followed by SOMS (1.0 g). The solvent was removed at 40° C. and 119 mbar. MeOH (50 mL) was added to the round-bottom flask followed by solvent removal at 40° C. and 119 mbar. This cycle was repeated four more times for a total of six times. The SOMS were washed during filtration with EtOH (300 mL) and the solvent was concentrated in vacuo to afford resveratrol, a mixture of isomers, as off-white solid 29.7 mg, 99%. ¹H-NMR (400 MHz, CDCl₃) δ 7.31-7.37 (m, 5H), 7.21 (d, 1H), 7.18 (d, 1H), 6.03-6.85 (m, 3H).

Example 16: Use of SOMS as Nanoreactors to Facilitate the Synthesis of Diazepam (Valium®)

Scheme 16.0: Synthesis of diazepam (Valium®).

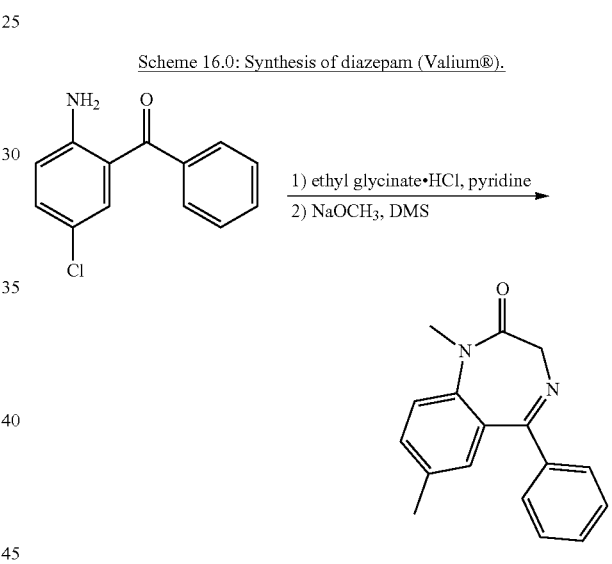

Diazepam is a benzodiazepine family drug commonly used in the treatment of anxiety, and can be prepared as shown in Scheme 16.0.

Example 17: Use of SOMS as Nanoreactors to Facilitate the Synthesis of Amphetamine (Adderall®)

Scheme 17.0: Synthesis of amphetamine (Adderall®).

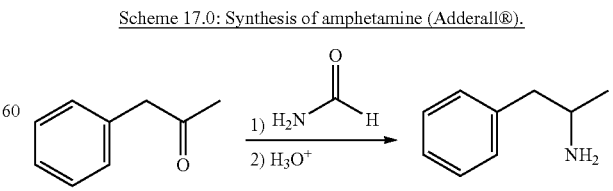

Adderall is a central nervous system stimulant commonly used in the treatment of anxiety and can be prepared as shown in Scheme 17.0.

Example 18: Use of SOMS as Nanoreactors to Facilitate the Synthesis of Kyotorphin
Scheme 18.0: Synthesis of kyotorphin.
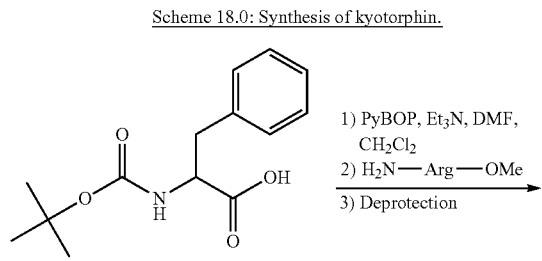
Kyotorphin is a neuroactive dipeptide used in the treatment of pain and can be prepared as shown in Scheme 18.0.
Example 19: Use of SOMS as Nanoreactors to Facilitate the Synthesis of Peptides
Scheme 19.0: General scheme for the step-wise synthesis of peptides.
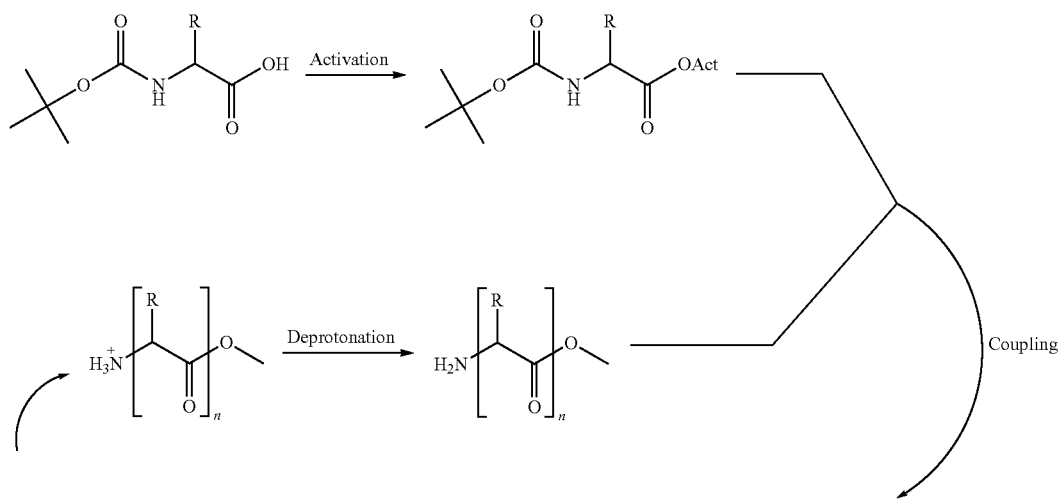
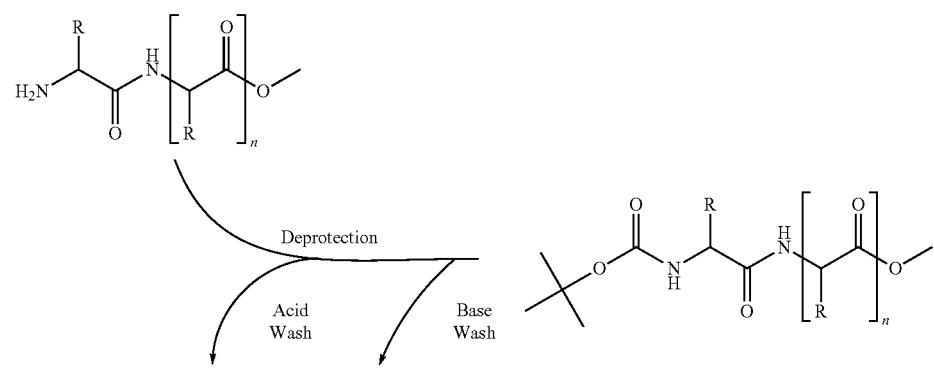

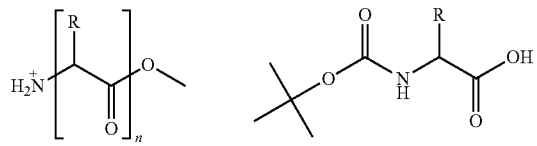

The chemical synthesis of peptides can be carried out using traditional solution-phase techniques or by solid-phase methods. The use of SOMS nanoreactors in peptide synthesis (Scheme 19.0) offers the ability to dramatically decrease the time required to couple peptides (from hours to minutes) while also affording the peptides in quantitative (100%) yield which renders the need for purification unnecessary. SOMS nanoreactor facilitated peptide synthesis offers a much needed alternative to traditional synthesis methods.

Specific Examples

Boc-Deprotection Procedure—The Boc-protected (0.5 mmol) was dissolved in $CH_2Cl_2$ (5.0 mL) in a 100 mL round-bottom flask. SOMS (500 mg) was added to the flask and solvent was removed in vacuo. $CH_2Cl_2$ (5.0 mL) was added to the flask followed by hydrochloric acid (HCl, 4N in dioxane, 1.0 mL) and the solvent was removed using the rotary evaporator (788 mbar, 40° C. This step was repeated one additional time. The SOMS was washed during filtration with MeOH (100 mL). The solvent was removed in vacuo. The resulting solid was dissolved in NaOH (aq) (1.0 M in water, 60 mL) and $CH_2Cl_2$ (60 mL). The aqueous layer was removed and the organic layer was washed an additional two times with NaOH (aq) (1.0 M in water, 60 mL). The resulting organic layer was dried with $Na_2SO_4$ and the solvent was removed in vacuo to afford the desired free amine.

Scheme 19.1: Synthesis of H₂N-Trp-OMe.

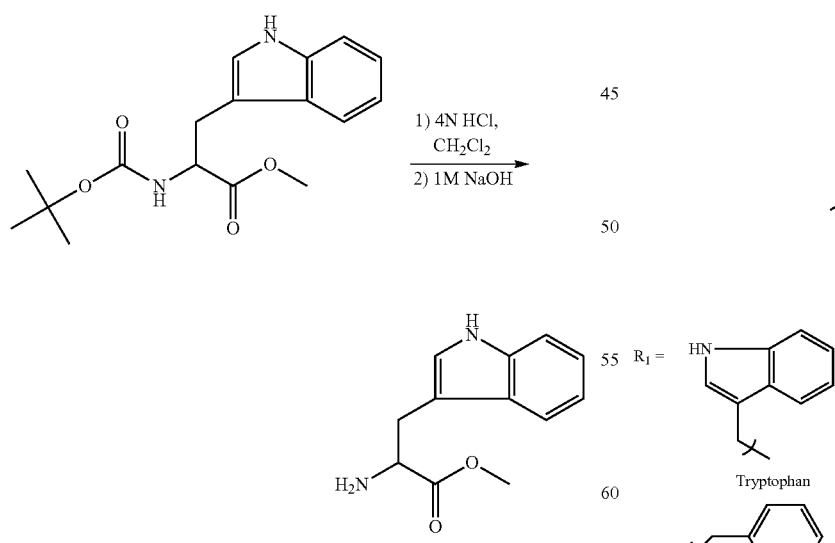

Synthesis of H₂N-Trp-OMe. H₂N-Trp-OMe was afforded as a clear oil 109.2 mg, 100%. $^1$H-NMR (400 MHz, CDCl$_3$) δ 7.54 (d, 1H), 7.27 (d, 1H), 7.19 (t, 1H), 7.02 (m, 2H), 3.79 (t, 1H), 3.57 (s, 3H), 3.23 (dd, 2H).

Scheme 19.2: Synthesis of methyl 4-amino-1-methyl-1H-pyrrole-2-carboxylate.

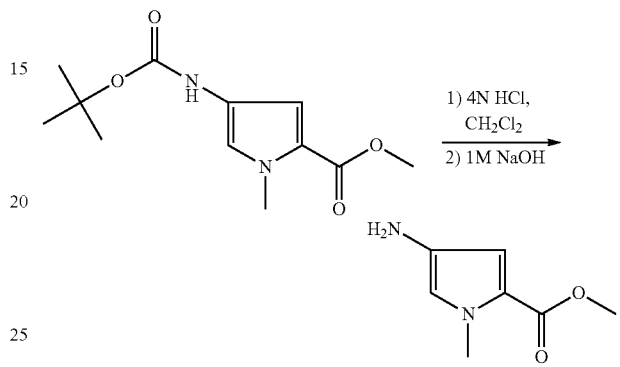

Synthesis of methyl 4-amino-1-methyl-1H-pyrrole-2-carboxylate. Methyl 4-amino-1-methyl-1H-pyrrole-2-carboxylate was afforded as a light yellow oil 77.1 mg, 100%. $^1$H-NMR (400 MHz, CDCl$_3$) δ 6.41 (s, 1H), 5.89 (s, 1H), 3.89 (s, 3H), 3.82 (s, 3H).

Scheme 19.3: General scheme for the synthesis of di-peptides.

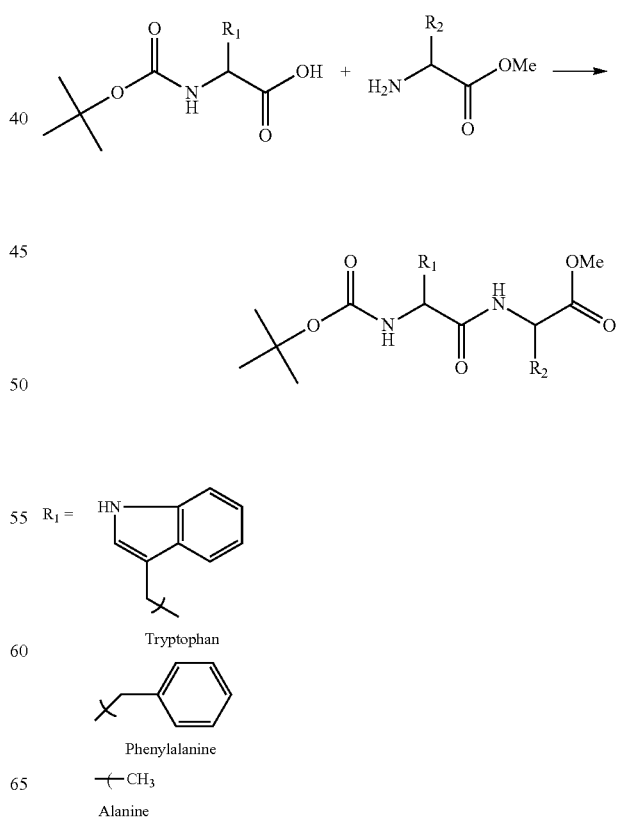

-continued

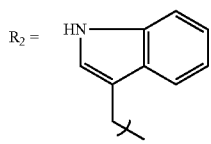
Tryptophan

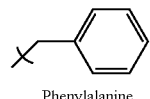
Phenylalanine

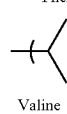
Valine

Coupling Procedure—The N-protected amino acid (0.5 mmol) was dissolved in dichloromethane (CH$_2$Cl$_2$, 10 mL) in a 100 mL round-bottom flask. Base (triethyl amine or diisopropyl amine, 0.5 mmol) was added to the flask. In a separate beaker, the activating agents [PyBOP (0.5 mmol) or EDC/HOBt (0.5 mmol each) or EDC (0.5 mmol)] were added along with dimethyl formamide (DMF, 0.5 mL). The contents of the beaker were added to the round-bottom flask and the solvent was removed at 40° C. and 719 mbar using a rotary evaporator. The C-protected amino acid (0.5 mmol) was dissolved CH$_2$Cl$_2$ (10 mL) and added to the contents of the round-bottom flask and the solvent was removed at 40° C. and 719 mbar using a rotary evaporator. CH$_2$Cl$_2$ (10 mL) was evaporated at 40° C. and 719 mbar using a rotary evaporator. This step was repeated an additional three times. The SOMS were washed during filtration using CH$_2$Cl$_2$ (100 mL). The organic layer was washed with saturated NaHCO$_3$ (3×100 mL) and HCl (1.0 M, 3× 100 mL). The organic layer was dried with Na$_2$SO$_4$ and concentrated in vacuo to afford the desired di-peptide.

Scheme 19.4: Synthesis of Boc-Trp-Trp-OMe.

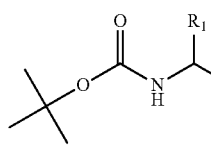

R$_1$ = 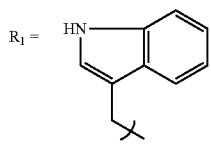
Tryptophan

R$_2$ = 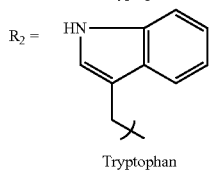
Tryptophan

Synthesis of Boc-Trp-Trp-OMe. Boc-Trp-Trp-OMe was recovered as an off-white solid (75%). $^1$H-NMR (400 MHz, CDCl$_3$) δ 7.26-7.44 (m, 6H), 6.68 (d, 4H), 6.25 (br, 1H), 5.05 (d, 1H) 4.55 (m, 1H), 3.47 (s, 3H), 3.05-3.21 (m, 2H), 1.48 (3, 9H).

Scheme 19.5: Synthesis of Boc-Phe-Trp-OMe.

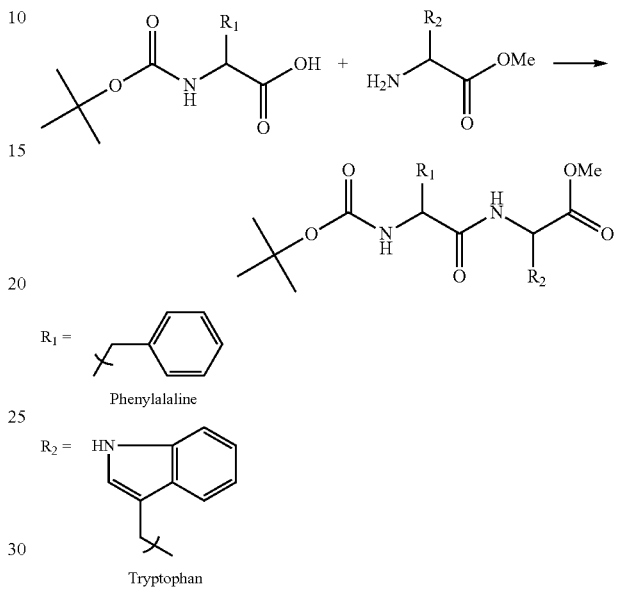

Synthesis of Boc-Phe-Trp-OMe. Boc-Phe-Trp-OMe was recovered as an off-white solid (81%). $^1$H-NMR (400 MHz, CDCl$_3$) δ 6.93-7.19 (m, 10H), 4.67 (m, 1H), 4.36 (dd, 1H), 3.51 (s, 3H), 3.01-3.19 (m, 2H)

Scheme 19.6: Synthesis of Boc-Phe-Phe-OMe.

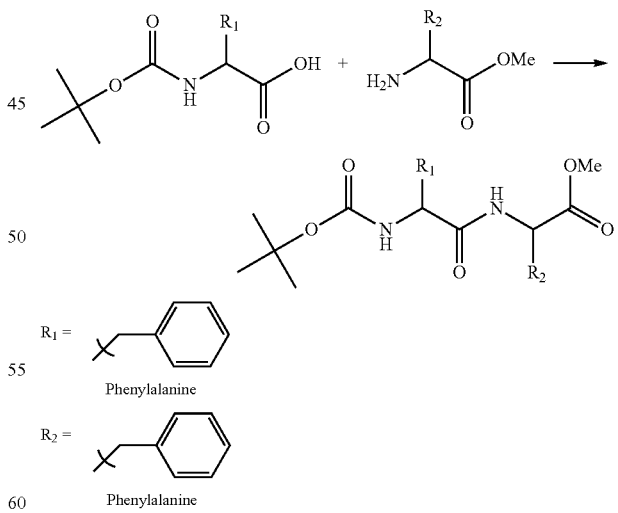

Synthesis of Boc-Phe-Phe-OMe. Boc-Phe-Phe-OMe was recovered as an off-white solid (84%). $^1$H-NMR (400 MHz, CDCl$_3$) δ 7.16-7.48 (m, 8H), 6.68 (d, 2H), 6.27 (br, 1H), 4.70 (br, 1H), 4.27 (dd, 1H), 3.48 (s, 3H), 3.05-3.21 (m, 2H), 1.52 (3, 9H).

Scheme 19.7: Synthesis of Boc-Phe-Val-OMe.

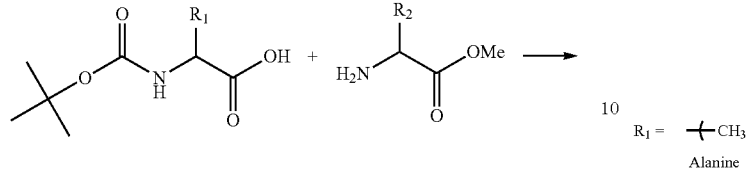

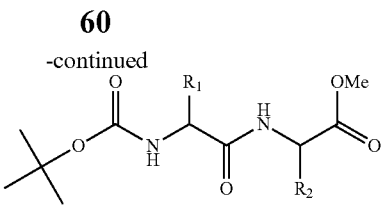

$R_1 = $ —CH$_3$
Alanine $R_2 = $ HN-indole
Tryptophan

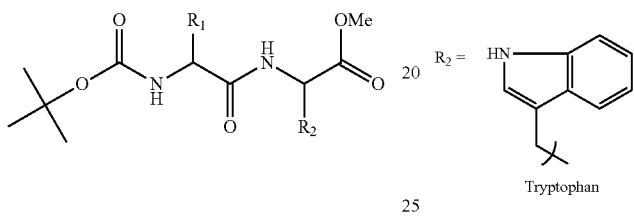

$R_1 = $ benzyl
Phenylalaline $R_2 = $ isopropyl
Valine

Synthesis of Boc-Phe-Val-OMe. Boc-Phe-Val-OMe was recovered as an off-white solid (83%). $^1$H-NMR (400 MHz, CDCl$_3$) δ 7.81 (dd, 2H), 7.37 (m, 3H), 6.57 (br, 1H), 5.01 (br, 1H), 4.1 (m, 2H), 3.51 (s, 3H), 3.01-3.55 (m, 3H), 1.49 (s, 9H), 0.89 (d, 6H).

Synthesis of Boc-Ala-Trp-OMe. Boc-Ala-Trp-OMe was recovered as an off-white solid (77%). $^1$H-NMR (400 MHz, CDCl$_3$) δ 7.26-7.44 (m, 4H), 6.68 (d, 1H), 6.04 (br, 1H), 5.03 (br, 1H), 3.95-3.18 (m, 5H), 1.48 (3, 9H).

Sequential Coupling Procedure—The N-terminus amino acid (100 mg) was dissolved in CH$_2$Cl$_2$ (10 mL) in a 50 mL round-bottom flask. PyBoP (1 mol eq.) and DiPEA (1 mol eq.) were added, followed by SOMS (1 g). The solvent was removed at 40° C. and 719 mbar. CH$_2$Cl$_2$ (10 mL) was added and the solvent removed at 40° C. and 719 mbar. This was repeated three more times, for a total of five times. Meanwhile, in a separate flask, the C-terminus protected amino acid (1 mol eq.) was diluted in CH$_2$Cl$_2$ (15 mL) and added to the round-bottom flask and the solvent removed at 40° C. and 719 mbar. CH$_2$Cl$_2$ (10 mL) was added and the solvent removed at 40° C. and 719 mbar. This was repeated three more times, for a total of five times. HCl (4 N in dioxane, 5 mL) was added and the solvent was removed at 40° C. and 719 mbar. CH$_2$Cl$_2$ (10 mL) was added and the solvent removed at 40° C. and 719 mbar. This was repeated three more times, for a total of five times. The SOMS were suspended in H$_2$O (500 mL) and allowed to stir for 30 min. The SOMS were vacuum filtered and allowed to dry.

In a separate flask, a second N-terminus amino acid (100 mg) was dissolved in CH$_2$Cl$_2$ (10 mL) in a 50 mL round-bottom flask. PyBoP (1 mol eq.) and DiPEA (1 mol eq.) were added, followed by SOMS (1 g). The solvent was removed at 40° C. and 719 mbar. CH$_2$Cl$_2$ (10 mL) was added and the solvent removed at 40° C. and 719 mbar. This was repeated three more times, for a total of five times. The SOMS from the two round-bottom flasks were combined, followed by CH$_2$Cl$_2$ (50 mL) and the solvent removed at 40° C. and 719 mbar. CH$_2$Cl$_2$ (10 mL) was added and the solvent removed at 40° C. and 719 mbar. This was repeated three more times, for a total of five times. The SOMS were washed during filtration with CH$_2$Cl$_2$ (300 mL). Solvent was removed in vacuo to afford the tri-peptide.

Scheme 19.8: Synthesis of Boc-Ala-Trp-OMe.

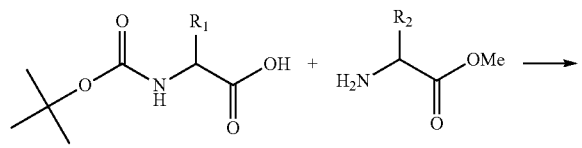

Scheme 19.9: Synthesis of Boc-Trp-Trp-Trp-OMe
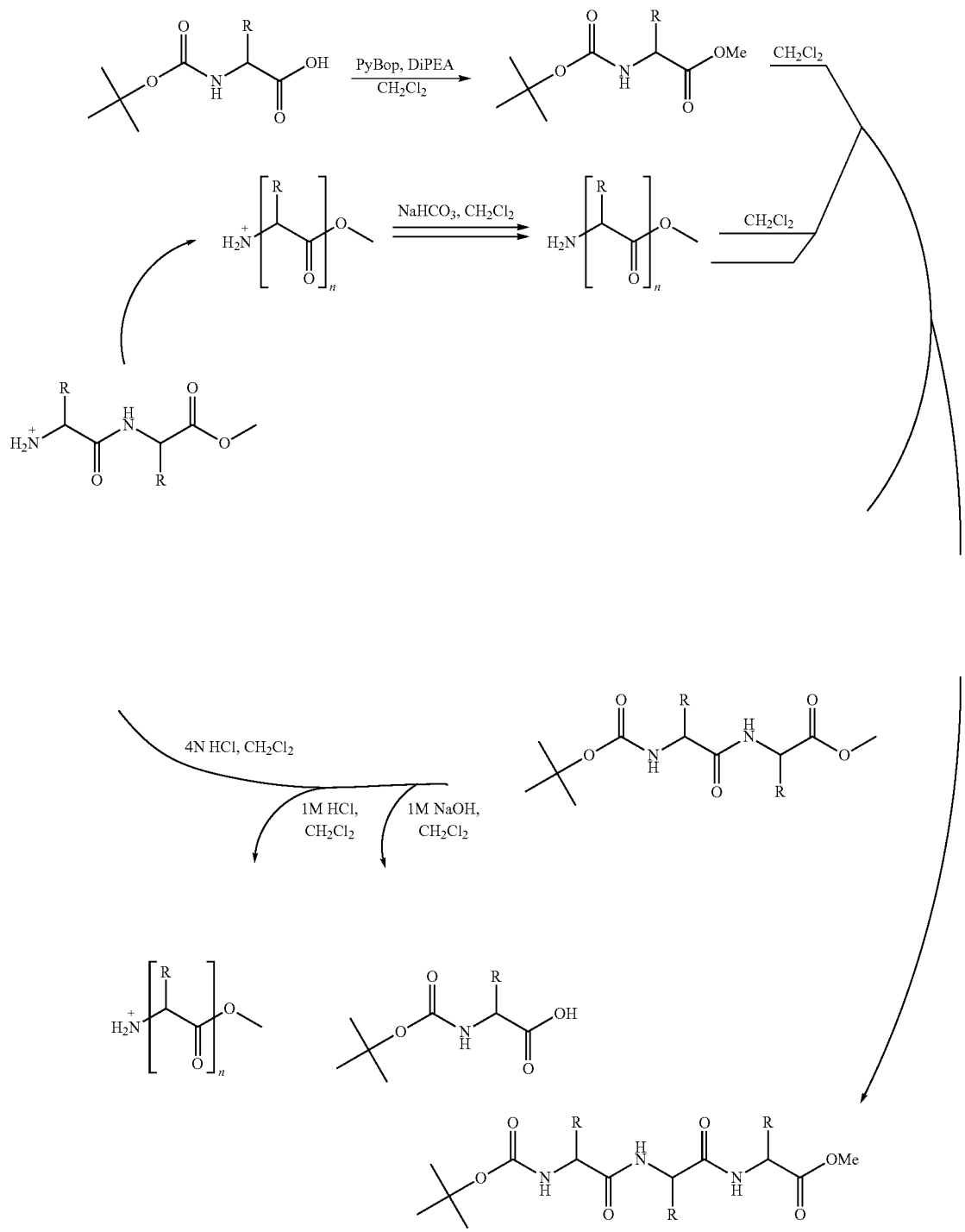
where n = 1, 2.
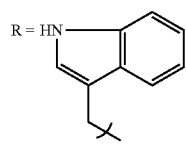
Tryptophan Synthesis of Boc-Trp-Trp-Trp-OMe. Boc-Trp-Trp-Trp-OMe was recovered as an off-white sold (60%). $^1$H-NMR (400 MHz, CDCl$_3$) δ 7.23-7.48 (m, 9H), 6.69 (d, 4H), 6.25 (br, 1H), 5.0 (d, 1H) 4.55 (m, 1H), 4.47 (m, 1H), 3.05-3.21 (m, 6H), 1.48 (3, 9H).

Example 20: Use of SOMS as Nanoreactors to Facilitate the Synthesis of Monastrol Scheme 20.0: Synthesis of monastrol.

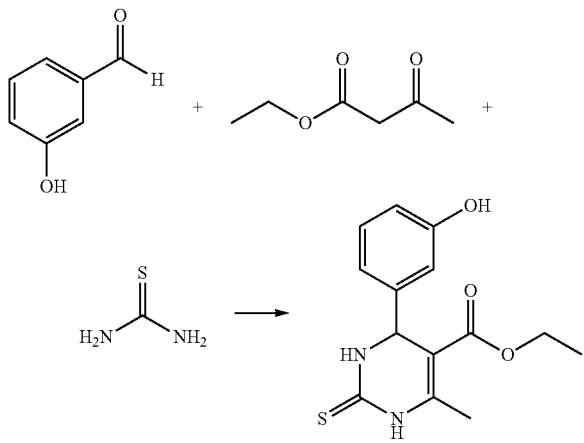

Monastrol is a cell-permeable inhibitor of mitosis and can be prepared as shown in Scheme 20.0.

Specific Examples

Synthesis of monastrol. In a 100 mL round-bottom flask, 2-hydroxy benzaldehyde (75 mg, 0.614 mmol) was added to a 100 mL round-bottom flask followed by CH$_2$Cl$_2$ (5 mL), ethyl acetoacetate (79.9 mg, 0.614 mmol), and thiourea (76.7 mg, 0.614 mmol). SOMS (2.0 g) were added and CH$_2$Cl$_2$ was added until the SOMS were saturated. The solution was heated at 50° C. for 24 hrs. The SOMS were washed during filtration with CH$_2$Cl$_2$ (300 mL) and the solvent was concentrated in vacuo to afford the monostrol as an off-white solid (152.6 mg, 85%). $^1$H-NMR (400 MHz, CDCl$_3$) δ 7.24 (m, 1H), 6.97-7.06 (m, 2H), 6.90 (m, 1H), 5.24 (s, 1H), 4.14-4.18 (m, 2H), 2.48 (s, 3H), 1.23 (s, 3H).

Example 21: Use of SOMS as Nanoreactors to Facilitate the Synthesis of Biodiesel Fuel Scheme 21.0: Synthesis of biodiesel fuel wherein R and R$_1$ are carbon bearing residues.

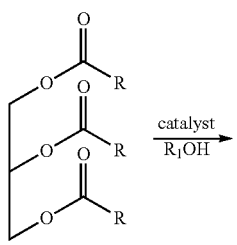

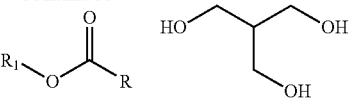

Biodiesel fuel is commonly produced from the catalyzed reaction of triglycerides (plant or animal-based fats) and alcohol. The use of SOMS nanoreactors allows for the use of all triglyceride sources (including used cooking oil) and all alcohol (hydroxyl bearing carbon residues, R$_2$) sources in the synthesis of biodiesel fuel; traditional methods of biodiesel fuel synthesis can only tolerate a limited number of triglyceride and alcohol sources.

Continued dependence on fossil fuels (petroleum, coal, and natural gas) for energy production pose numerous and significant challenges. Fossil fuels are non-renewable, limited in supply, and cause damage to the environment. The search for renewable, readily available, environmentally acceptable, technically feasible, and economically competitive alternative fuels remains a practical and an ethical obligation.

Biodiesel is an alternative fuel that contains approximately 90% of the energy content of fossil derived diesel and is as a promising long-term replacement to petroleum-based diesel fuels (Tabatabaei et al. *Biofuel Research Journal* 2 (3): 258-267 (2015)). In many ways, biodiesel is an advantageous replacement to fossil derived diesel as it is biodegradable, it possesses an inherent lubricity (which improves engine longevity) and higher flashpoint (which makes it safe to store, handle and transport), it is compatible with the existing fuel distribution infrastructure (Ajala et al. *ChemBioEng Reviews* 2 (3): 145-156 (2015)), and reduces combustion emissions to near zero (Atabani et al. *Renewable and Sustainable Energy Reviews* 16 (4): 2070-2093 (2012)).

The synthesis of biodiesel (chemically known as fatty acid esters) is technically and logistically simple. Combine a lipid (typically vegetable oil), alcohol (typically methanol), catalyst, and heat at a moderate temperature (approximately 60° C.). Following purification, biodiesel, suitable for combustion in any compression engine, is obtained. The method for this 'transesterification' of lipids is so simple it is commonly taught in sophomore level collegiate organic chemistry teaching laboratories and is the method of choice used at large-scale biodiesel production facilities and by at home do-it-yourselfers alike.

Despite biodiesel's numerous advantages, it currently does not significantly contribute to total energy generation. In 2015, the use of biodiesel for energy production accounted for only 9.5% of total bioenergy generation, a mere 0.5% of total energy generation in the United States (Warner, et al. *Bioenergy Market Report; National Renewable Energy Laboratory*; p 70 (2017)). And while contributions from other (non-biofuel) renewable energy are expected to increase in United States' by 2040, forecasted contributions from biodiesel in 2040 remain consistent with today's minor contributions (LaRose, A. et. al., *Annual Energy Outlook* 2017 *with projections to* 2050; *U.S. Energy Information Administration, p* 64 (2017). With all the advantages biodiesel affords, why doesn't biodiesel play a larger role in the energy landscape moving forward?

The challenges facing the contributions of biodiesel to total energy production are numerous and impacted by feedstock selection, the transesterification method used, and subsequent biodiesel purification.

Biodiesel production from pure plant-based oils is a well-established process (Demirbas, *Progress in Energy and Combustion Science*, 31 (5-6) (2005)), however the use of pure plant-based oils poses economic considerations and significant risks to food security. The major cost factor in the production of biodiesel is the cost of the raw material—catalyst and raw material costs account for 70-88% of the overall costs Chuah et al. *Journal of Cleaner Production* 146: 181-193 (2017)). Furthermore, competition between the edible oil market and biodiesel market remains a global concern. Between 2004-2007, approximately 34% of edible oil was estimated for worldwide biodiesel production (Aransiola et al., *Biomass and Bioenergy* 61: 276-297 (2014)). In an effort to alleviate feed-stock challenges, the use of used waste cooking oils (which are up to three times less expensive than pure oils and are capable of producing around 50% of current biodiesel demand) as feedstock for biodiesel production has been extensively explored (Tabatabaei et al. *Biofuel Research Journal* 2 (3): 258-267 (2015)).

If waste cooking oil is the most economically and ethically viable feedstock for biodiesel production, then serious transesterification challenges must be solved. Waste cooking oil differs chemically from their pure-counterparts as pure oils slowly and partially decompose into free fatty acids (FFAs) upon extended use which complicates biodiesel production. The presence of FFAs dramatically increases the production of soap when traditional alkali catalysts are used, decreasing the overall yield of biodiesel. Id. The acid catalyzed transesterification of used cooking oil 'tolerates' the presence of FFAs, as both oil and FFAs are converted into biodiesel, however, the acid catalyzed conversion of FFAs is time consuming (often requiring greater than four hours to reach completion) and produces water as a byproduct which can dramatically decrease the overall yield of biodiesel.

Furthermore, regardless of the reactants present, basic chemical reactivity challenges persist. The feedstock oil and alcohol are not miscible, and oil that does not come in contact with alcohol will not undergo transesterification—efforts in increasing miscibility by decreasing droplet size, the use of co-solvent, and the use of microwave (Barnard et al., *Energy & Fuels* 21 (3): 1777-1781 (2007)), membrane reactors (Atadashi et al., *Renewable and sustainable energy reviews* 15(9): 5051-5062 (2011)), and microfluidic devices (Britton and Raston. *RSC Advances* 5 (3): 2276-2280 (2014)) have all been used in an effort to improve miscibility and subsequent reactivity. Even when the reactants are miscible, they must collide with sufficient velocity and in the correct, three-dimensional, orientation such that transesterification will occur.

Upon completion of transesterification, the produced biodiesel must be purified from its co-product, glycerol. While purification is relatively easy when pure plant-based oil feedstocks are quantitatively converted into biodiesel, the presence of FFAs, water, unconverted and partially converted oils (the product of incomplete transesterification) and alcohol impact the ease of biodiesel purification (Gnanaprakasam et al., *Journal of Energy* 2013: 1-10 (2013))—biodiesel produced from used cooking oil with an FFA percentage of 10% requires different purification procedures than biodiesel produced from used cooking oil with a FFA percentage of 23%. Chemists are routinely forced to sacrifice yields in an effort to produce market worthy biodiesel which increases production costs (Javidialesaadi and Raeissi. *APCBEE Procedia*, 5:474-478 (2013)). With the purification procedures being dependent on oil feedstock and the transesterification method used, the need of a 'one size fits all' procedure remains the hurdle in biodiesel proliferation (Aransiola et al., *Biomass and Bioenergy* 61: 276-297 (2014)).

The use of SOMS as a nanoreactor addresses these issues and provides a novel procedure for the synthesis of biodiesel. The procedure is tolerant to a diverse range of feedstock oils, it is very efficient at producing biodiesel fuel at quantitative yields, and subsequent purification is predictably simple.

Any alternative fuel must be technically feasible, economically competitive, environmentally acceptable, and readily available. In 2016, the cost of biodiesel production was more expensive than conventional diesel which drove the price of biodiesel to over $0.50/L when compared to normal diesel $0.35/L20. Production of biodiesel using SOMS addresses many of the challenges of inherent in tradition biodiesel production methods while simultaneously decreasing production costs. Feedstock costs are reduced as SOMS biodiesel synthesis procedure tolerates any feedstock oils—even those high in FFA content. Furthermore, transesterification costs are also reduced as the procedure synthesizes biodiesel more efficiently than traditional methods while requiring lower temperatures. Finally, purification costs are reduced as the biodiesel is produced in quantitative yields, which makes purification predictable and simple.

As discussed in Example 1, SOMS behaves as a nanoreactor for, in this case, biodiesel synthesis when the oil, alcohol, and acid catalyst are 'flexed': the oil and catalyst are diluted with alcohol and introduced to SOMS which causes SOMS to swell. SOMS contracts upon the removal of excess alcohol which drives the reactants closer together in SOMS. Upon complete removal of excess methanol, the reactants are encapsulated in SOMS so close to one another that transesterification is ensured. This flexing process can be repeated which drives the reaction to completion. The synthesized biodiesel is easily recovered when the biodiesel laden SOMS is washed with excess methanol.

Figure 5:
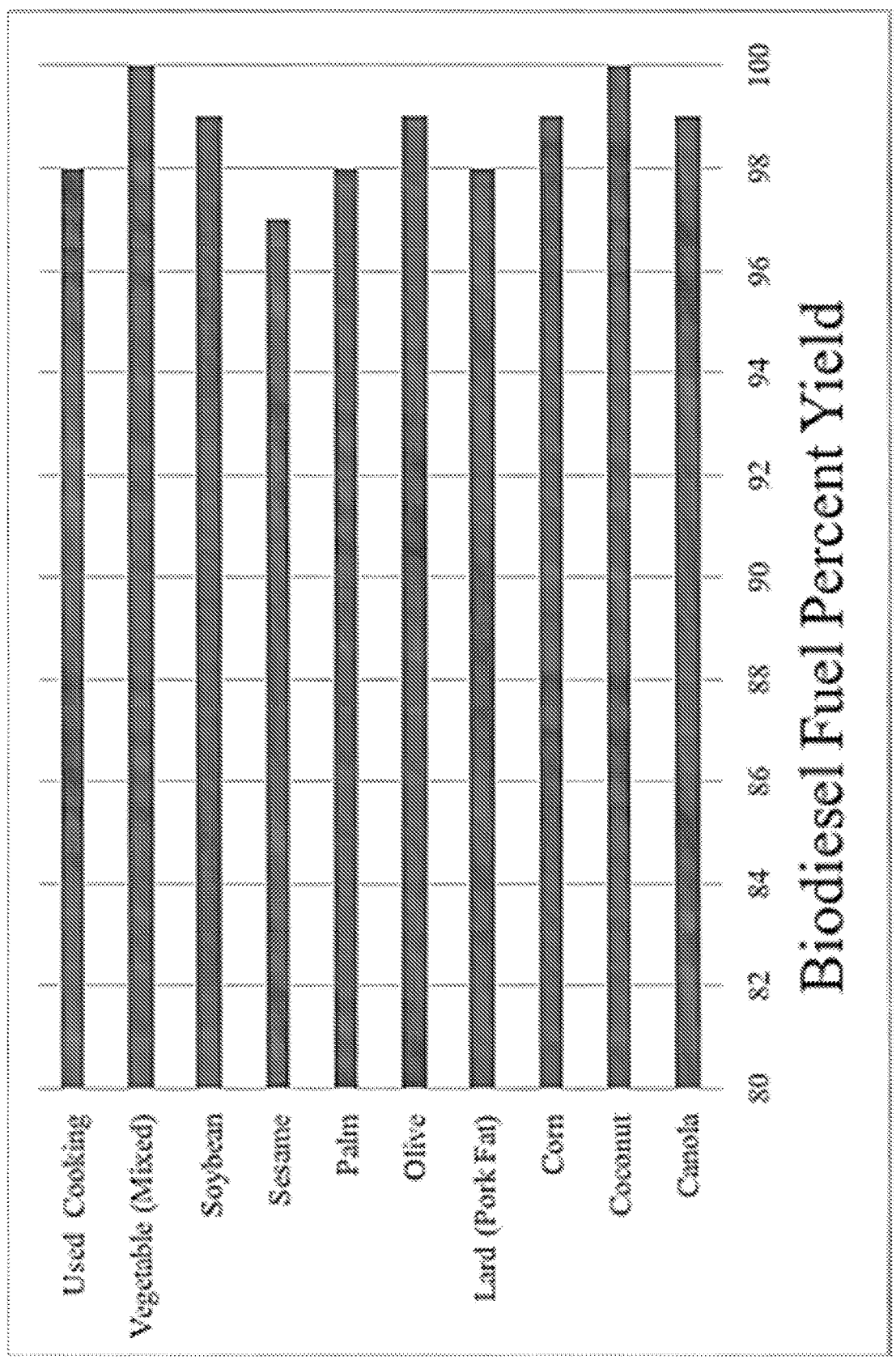
FIG. 5. Percent yields of SOMS produced biodiesel from various sources.

Using this method, biodiesel can be produced in efficiently and with high yield, regardless of the feedstock used. The transesterification of canola oil in SOMS was found to be 50% complete after six closes and approached completion (99%+) after 13 closes, a process that was complete in approximately 20 minutes. See FIG. 3A. Furthermore, SOMS was capable of transesterifying numerous oil feedstocks from pure vegetable oils (mixed vegetable oil, olive, corn, etc.) to common waste oils (used cooking oil and lard—waste animal fat), FIG. 5. Most importantly, SOMS is capable of repeatedly facilitating the transesterification of biodiesel with no observable decline in yield or efficiency. SOMS produced 98% pure biodiesel with high efficiency even after ten successive syntheses. See FIG. 4.

SOMS is utilized also to prepare alternative biofuels. The most commonly produced biodiesel is produced using methanol. Methanol is relatively cheap when compared to other alcohols. And while these methyl ester fatty acids are suitable for compression engine combustion, fatty acid esters derived from different alcohols have physical characteristics that make their combustion more appealing. Fatty acid ethyl esters provide the opportunity to synthesize biodiesel that is a truly 'green' as ethanol can be sourced naturally (Nikhom and Tongurai, *Fuel* 117:926-931 (2014)). Furthermore, fatty acid esters synthesized from propanols and butanols have a higher lubricity which decreases engine wear and increases engine longevity (Zaher and Soliman, *Egyptian Journal of Petroleum* 24(4): 439-443 (2015)). Fatty acid ethyl esters are be synthesized using SOMS with the same efficiency and yield as fatty acid methyl esters.

Specific Examples

| Oil ($R_1$ component) | | Alcohol ($R_2$ component) | |
| --- | --- | --- | --- |
| Coconut Oil | Used Cooking Oil | Methanol | $^n$Butanol |
| Canola Oil | Lard | Ethanol | $^{iso}$Butanol |
| Vegetable Oil | Sesame Oil | $^n$Propanol | 2-Methyl-3-butyn-2-ol |
| Safflower Oil | Peanut Oil | $^{iso}$Propanol | |
| Olive Oil | Corn Oil | | |

Heterogeneous Acid Catalyzed Procedure: Oil (1 g), was diluted in methanol (20 mL) in a 200 mL round-bottom flask. Aqueous acid [HCl (aq), $H_2SO_4$ (aq), or $H_3PO_4$ (aq)] or organic acid [HCl in dioxane, HCl in MeOH, or HCl in diethyl ether] (1 mL) was added to the flask followed by SOMS (20 g). The flask was heated at 45° C. for 4 hours. The SOMS were washed during filtration with MeOH (500 mL) and solvent was removed in vacuo. The resulting biphasic solution was separated and the top ester layer was recovered as a light brown viscous oil (100%).

Heterogeneous Base Catalyzed Procedure: Oil (1 g), was diluted in methanol (20 mL) in a 200 mL round-bottom flask. Sodium methoxide (1 mL), afforded in situ as a solution of NaOH in MeOH or $NaOCH_3$ in MeOH, was added to the flask followed by SOMS (20 g). The flask was heated at 45° C. for 15 min. The SOMS were washed during filtration with MeOH (500 mL) and the resulting solution was neutralized with HCl and solvent was removed in vacuo. The resulting biphasic solution was separated and the top ester layer was recovered as a light brown viscous oil (100%).

Homogeneous Acid Catalyzed Procedure: Oil (1 g) was diluted with methanol (50 mL) in a 200 mL round-bottom flask. Aqueous acid [HCl (aq), $H_2SO_4$ (aq), or $H_3PO_4$ (aq)] or organic acid [HCl in dioxane, HCl in MeOH, or HCl in diethyl ether] (1 mL) was added to the flask followed by SOMS (20 g). The solvent was removed at 40° C. and 119 mbar. MeOH (50 mL) was added to the round-bottom flask followed by solvent removal at 40° C. and 119 mbar. This cycle was repeated nine more times for a total of 11 times. The SOMS were washed during filtration with MeOH (500 mL) and solvent was removed in vacuo. The resulting biphasic solution was separated and the top ester layer was recovered as a light brown viscous oil (100%).

Homogeneous Base Catalyzed Procedure: Oil (1 g) was diluted with methanol (50 mL) in a 200 mL round-bottom flask. Sodium methoxide (1 mL), afforded in situ as a solution of NaOH in MeOH or $NaOCH_3$ in MeOH, was added to the flask followed by SOMS (20 g). The solvent was removed at 40° C. at 119 mbar. MeOH (20 mL) was added to the round-bottom flask followed by solvent removal at 40° C. and 119 mbar. This cycle was repeated one additional time for a total of three times. The SOMS were washed during filtration with MeOH (500 mL) and the resulting solution was neutralized with HCl and solvent was removed in vacuo. The resulting biphasic solution was separated and the top ester layer was recovered as a light brown viscous oil (100%).

Synthesis of fatty acid methyl esters from vegetable oil. $^1$H-NMR (400 MHz, $CDCl_3$) δ 3.55 (s, 3H), 2.61 (t, 2H), 2.48 (p, 2H), 1.89 (m, 2H), 1.51 (m, 2H), 1.31 (m, 20H), 0.71 (t, 3H).

Synthesis of fatty acid methyl esters from coconut oil. $^1$H-NMR (400 MHz, $CDCl_3$) δ 3.57 (s, 3H), 2.62 (t, 2H), 2.49 (p, 2H), 1.87 (m, 2H), 1.50 (m, 2H), 1.30 (m, 20H), 0.71 (t, 3H).

Synthesis of fatty acid methyl esters from canola oil. $^1$H-NMR (400 MHz, $CDCl_3$) δ 3.55 (s, 3H), 2.60 (t, 2H), 2.48 (p, 2H), 1.90 (m, 2H), 1.52 (m, 2H), 1.33 (m, 20H), 0.72 (t, 3H).

Synthesis of fatty acid methyl esters from peanut oil. $^1$H-NMR (400 MHz, $CDCl_3$) δ 3.58 (s, 3H), 2.67 (t, 2H), 2.43 (p, 2H), 1.85 (m, 2H), 1.53 (m, 2H), 1.31 (m, 20H), 0.72 (t, 3H).

Synthesis of fatty acid methyl esters from olive oil. $^1$H-NMR (400 MHz, $CDCl_3$) δ 3.55 (s, 3H), 2.59 (t, 2H), 2.49 (p, 2H), 1.87 (m, 2H), 1.52 (m, 2H), 1.32 (m, 20H), 0.74 (t, 3H).

Synthesis of fatty acid methyl esters from lard. $^1$H-NMR (400 MHz, $CDCl_3$) δ 3.57 (s, 3H), 2.65 (t, 2H), 2.49 (p, 2H), 1.85 (m, 2H), 1.51 (m, 2H), 1.32 (m, 20H), 0.72 (t, 3H).

Synthesis of fatty acid methyl esters from sesame oil. $^1$H-NMR (400 MHz, $CDCl_3$) δ 3.55 (s, 3H), 2.60 (t, 2H), 2.45 (p, 2H), 1.88 (m, 2H), 1.51 (m, 2H), 1.33 (m, 20H), 0.73 (t, 3H).

Synthesis of fatty acid methyl esters from corn oil. $^1$H-NMR (400 MHz, $CDCl_3$) δ 3.57 (s, 3H), 2.62 (t, 2H), 2.47 (p, 2H), 1.91 (m, 2H), 1.52 (m, 2H), 1.31 (m, 20H), 0.72 (t, 3H).

Synthesis of fatty acid methyl esters from peanut oil. $^1$H-NMR (400 MHz, $CDCl_3$) δ 3.56 (s, 3H), 2.67 (t, 2H), 2.50 (p, 2H), 1.89 (m, 2H), 1.52 (m, 2H), 1.33 (m, 20H), 0.72 (t, 3H).

Synthesis of fatty acid methyl esters from used-cooking oil. $^1$H-NMR (400 MHz, $CDCl_3$) δ 3.55 (s, 3H), 2.61 (t, 2H), 2.48 (p, 2H), 1.89 (m, 2H), 1.51 (m, 2H), 1.31 (m, 20H), 0.74 (t, 3H).

Scheme 21.1: Synthesis of biodiesel fuel using ethanol.

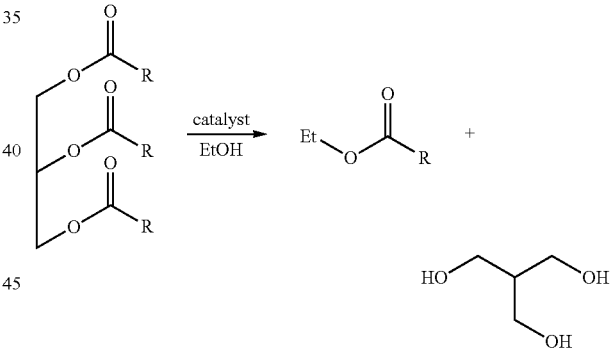

Synthesis of fatty acid ethyl esters from vegetable oil. $^1$H-NMR (400 MHz, $CDCl_3$) δ 3.57 (2, 3H), 2.60 (t, 2H), 2.51 (t, 3H), 2.43 (p, 2H), 1.91 (m, 2H), 1.50 (m, 2H), 1.33 (m, 20H), 0.8 (t, 3H).

Scheme 21.2: Synthesis of biodiesel fuel using $^n$propanol.

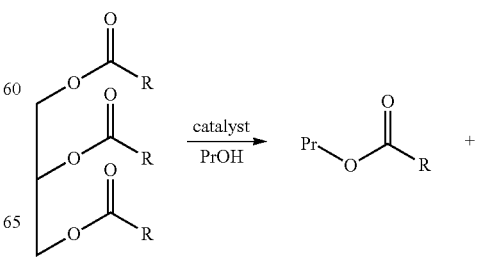

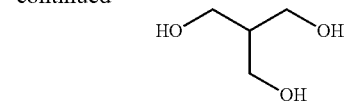

Synthesis of fatty acid propyl esters from vegetable oil. $^1$H-NMR (400 MHz, CDCl$_3$) δ 4.15 (t, 2H), 2.61 (t, 2H), 2.48 (p, 2H), 1.89 (m, 2H), 1.79 (m, 2H), 1.51 (m, 2H), 1.31 (m, 2H), 0.93 (t, 3H), 0.74 (t, 3H).

Scheme 21.3: Synthesis of biodiesel fuel using $^n$butanol.

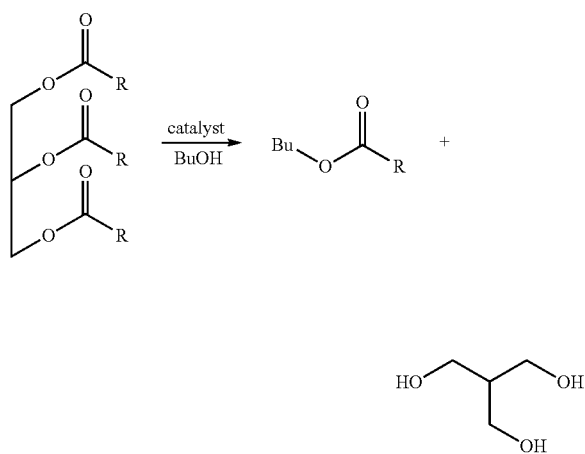

Synthesis of fatty acid $^n$butyl esters from vegetable oil. $^1$H-NMR (400 MHz, CDCl$_3$) δ 4.17 (t, 2H), 2.61 (t, 2H), 2.45 (p, 2H), 1.88 (m, 2H), 1.71 (m, 4H), 1.53 (m, 2H), 1.39 (m, 2H), 1.30 (m, 2H), 0.93 (t, 3H), 0.87 (t, 2H), 0.74 (t, 3H).

Scheme 21.4: Synthesis of biodiesel fuel using $^{iso}$propanol.

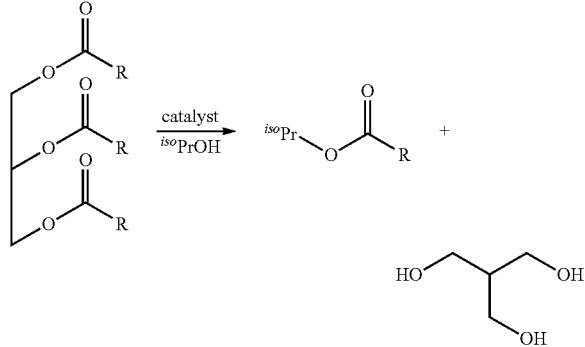

Synthesis of fatty acid $^n$ propyl esters from vegetable oil. $^1$H-NMR (400 MHz, CDCl$_3$) δ 4.81 (m, 1H), 2.31 (t, 2H), 2.49 (p, 2H), 1.91 (m, 2H), 1.50 (m, 2H), 1.45 (d, 6H), 1.31 (m, 2H), 0.74 (t, 3H).

Scheme 21.5: Synthesis of biodiesel fuel using $^{iso}$butanol.

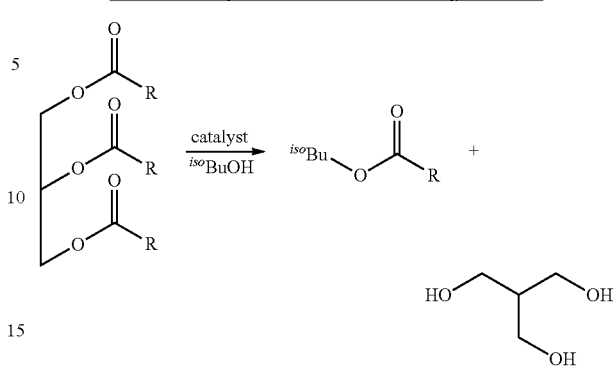

Synthesis of fatty acid $^n$butyl esters from vegetable oil. $^1$H-NMR (400 MHz, CDCl$_3$) δ 4.33 (d, 2H), 2.60 (t, 2H), 2.45 (p, 2H), 1.89 (m, 3H), 1.50 (m, 2H), 1.34 (m, 20H), 0.92 (d, 6H), 0.71 (t, 3H).

Scheme 21.5: Synthesis of biodiesel fuel using 2-methyl-3-butyn-2-ol.

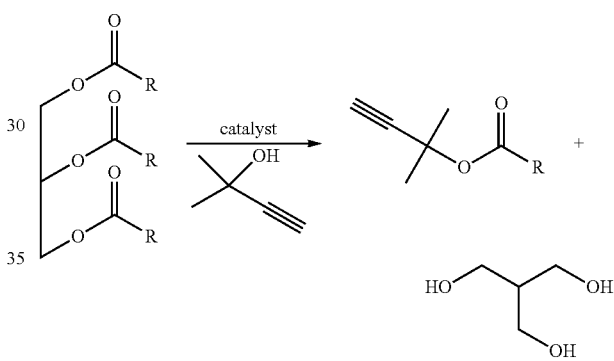

Synthesis of fatty acid 2-methyl-3-butyn-2-esters from vegetable oil. $^1$H-NMR (400 MHz, CDCl$_3$) δ 2.94 (s, 1H), 2.60 (t, 2H), 2.43 (p, 2H), 1.87 (m, 2H), 1.51 (m, 8H), 1.33 (m, 20H), 0.76 (t, 3H).

We claim:

1. A method for conducting a chemical reaction comprising:
   (i) combining reactants, solvent, and swellable organically modified silica (SOMS) to create a reaction mixture;
   (ii) conducting a first reaction cycle by evaporating the solvent from the SOMS;
   (iii) optionally conducting an additional reaction cycle by
      (a) reintroducing solvent to the SOMS; and then
      (b) evaporating the solvent from the SOMS;
   (iv) optionally repeating step (iii) one or more times;
   (v) washing the SOMS with solvent to recover the product in solution; and
   (vi) evaporating the solvent from the product solution of step (v) to isolate the product.

2. The method of claim 1, wherein combining reactants, solvent, and SOMS comprises:
   (i) dissolving the reactants in the solvent to create a reactant solution; and
   (ii) combining the reactant solution with the SOMS.

3. The method of claim 1, wherein additional reactant is optionally added with the solvent reintroduction in additional reaction cycles.

4. The method of claim 1, wherein the SOMS is a commerically available swellable organically modified silica.

5. The method of claim 1, wherein 1-15 reaction cycles are performed.

6. The method of claim 1, wherein steps (ii) and (iii) are conducted at 40° -60° C.

7. The method of claim 1, wherein the reaction proceeds to at least about 90% completion.

8. The method of claim 1, wherein the chemical reaction is selected from the group consisting of a nucleophilic alkyl substitution reaction, a nucleophilic alkyl substitution reaction, an electrophilic aromatic substitution reaction, a nucleophilic aromatic addition reaction, a cycloaddition reaction, a direct amidation reaction, an elimination reaction, an electrophilic alkene or alkyne addition reaction, a nucleophilic alkene or alkyne addition reaction, a one-pot reaction, a Wittig reaction, the synthesis of acetylsalicylic acid, the synthesis of acetaminophen, the synthesis of resveratrol, the synthesis of diazepam, the synthesis of amphetamine, the synthesis of kyotorphin, the synthesis of peptides, the synthesis of monastrol, and the synthesis of biodiesel fuel.

9. The method of claim 8, wherein the chemical reaction is the synthesis of biodiesel fuel.

10. The method of claim 1, wherein steps (ii) through (iv) are performed simultaneously.

11. The method of claim 10, wherein the simultaneous performance of steps (ii) through (iv) is conducted for 12-24 hours.

12. A method for conducting a multi-step chemical reaction comprising:
   (i) conducting a first reaction by
      (a) combining reactants, solvent, and swellable organically modified silica (SOMS) to create a reaction mixture;
      (b) conducting a first reaction cycle for the first reaction by evaporating the solvent from the SOMS;
      (c) optionally conducting an additional reaction cycle for the first reaction by
         (I) reintroducing solvent to the SOMS; and then
         (II) evaporating the solvent from the SOMS;
      (d) optionally repeating step (c) one or more times;
   (ii) conducting a subsequent reaction by
      (a) introducing solvent and one or more additional reactants to the SOMS;
      (b) conducting a first reaction cycle for the subsequent reaction by evaporating the solvent from the SOMS;
      (c) optionally conducting an additional reaction cycle for the subsequent reaction by
         (I) reintroducing solvent to the SOMS; and then
         (II) evaporating the solvent from the SOMS;
      (d) optionally repeating step (c) one or more times;
   (iii) optionally repeating step (ii) one or more times;
   (iv) washing the SOMS with solvent to recover the final product in solution; and
   (v) evaporating the solvent from the final product solution of step (iv) to isolate the final product.

13. The method of claim 12, wherein combining reactants, solvent, and SOMS comprises
   (i) dissolving the reactants in the solvent to create a reactant solution; and
   (ii) combining the reactant solution with the SOMS.

14. The method of claim 12, wherein additional reactant is optionally added with the solvent reintroduction in additional reaction cycles.

15. The method of claim 12, wherein the SOMS is a commercially available swellable organically modified silica.

16. The method of claim 12 wherein 1-15 reaction cycles are performed for the first reaction and for each of the subsequent reactions.

17. The method of claim 12, wherein the reaction cycles are conducted at 40°-60° C.

18. The method of claim 12, wherein the first reaction and each of the subsequent reaction(s) proceed to at least about 90% completion.

19. The method of claim 12, wherein the first reaction and each of the subsequent reactions are independently selected from the group consisting of a nucleophilic alkyl substitution reaction, a nucleophilic alkyl substitution reaction, an electrophilic aromatic substitution reaction, a nucleophilic aromatic addition reaction, a cycloaddition reaction, a direct amidation reaction, an elimination reaction, an electrophilic alkene or alkyne addition reaction, a nucleophilic alkene or alkyne addition reaction, a one- pot reaction, a wittig reaction, the synthesis of acetylsalicylic acid, the synthesis of acetaminophen, the synthesis of resveratrol, the synthesis of diazepam, the synthesis of amphetamine, the synthesis of kyotorphin, the synthesis of peptides, the synthesis of monastrol, and the synthesis of biodiesel fuel.

20. The method of claim 12, wherein
   a) steps (i)(b) through (i)(d) are performed simultaneously;
   b) steps (ii)(b) through (ii)(d) are performed simultaneously; or
   c) steps (i)(b) through (i)(d) and steps (ii)(b) through (ii)(d) are performed simultaneously.

21. The method of claim 20, wherein the simultaneous performance of steps (b) through (d) is conducted for 12-24 hours.

\* \* \* \* \*